United States Patent [19]
Peterson et al.

[11] Patent Number: 5,935,099
[45] Date of Patent: *Aug. 10, 1999

[54] DRUG PUMP SYSTEMS AND METHODS

[75] Inventors: Thomas L. Peterson, Shoreview; Michael L. Blomquist, Coon Rapids, both of Minn.

[73] Assignee: SIMS Deltec, Inc., St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/782,486

[22] Filed: Jan. 10, 1997

Related U.S. Application Data

[63] Continuation-in-part of application No. 08/555,304, Nov. 8, 1995, Pat. No. 5,658,250, application No. 08/206,737, Mar. 7, 1994, Pat. No. 5,669,877, application No. 08/586,952, Jan. 16, 1996, application No. 08/561,809, Nov. 22, 1995, application No. 08/540,960, Oct. 11, 1995, application No. 08/618,574, Mar. 20, 1996, Pat. No. 5,647,854, and application No. 08/281,179, Jul. 27, 1994, Pat. No. 5,695,473, which is a continuation of application No. 08/090,738, Jul. 13, 1993, abandoned

[60] Provisional application No. 60/010,090, Jan. 12, 1996.

[51] Int. Cl.⁶ ..................... A61M 31/00
[52] U.S. Cl. ............... 604/65; 604/67
[58] Field of Search .......... 604/65, 67; 417/18

[56] References Cited

U.S. PATENT DOCUMENTS

| | | |
|---|---|---|
| Re. 31,315 | 7/1983 | Jenkins et al. . |
| D. 294,733 | 3/1988 | Peterson et al. . |
| T961,004 | 8/1977 | Horton . |
| 2,968,804 | 1/1961 | Buffington . |
| 3,555,286 | 1/1971 | Cote . |
| 3,603,152 | 9/1971 | Alibert et al. . |
| 3,777,165 | 12/1973 | Bryant et al. . |
| 3,809,871 | 5/1974 | Howard et al. . |

(List continued on next page.)

FOREIGN PATENT DOCUMENTS

| | | |
|---|---|---|
| 2060151 | 8/1992 | Canada . |
| 0069350 | 1/1983 | European Pat. Off. . |
| 0078645A1 | 5/1983 | European Pat. Off. . |
| 0188288 | 7/1986 | European Pat. Off. . |
| 0233115 | 9/1987 | European Pat. Off. . |
| 0319272 | 6/1989 | European Pat. Off. . |
| 0384155 | 8/1990 | European Pat. Off. . |

(List continued on next page.)

OTHER PUBLICATIONS

Instruction Manual entitled "Quick Start for Speakerphone XT SVD", copyright 1996.
Bio Tek Instruments, Inc. Products Catalog, 32 pages, Apr. 1992.
Intel® document entitled, "28F001BX-T/28F001BX-B 1M(128Kx8) CMOS Flash Memory", dated Mar. 1991, 28 pages.
Intel® document entitled, "28F008SA8MBIT(1MBITx8) Flashtile™ Memory", dated Mar. 1992, 28 pages.
Lahti, W. et al., "Byte", pp. 311–318, Nov., 1990.

(List continued on next page.)

Primary Examiner—Michael Powell Buiz
Assistant Examiner—Julian W. Woo
Attorney, Agent, or Firm—Merchant, Gould, Smith, Edell, Welter & Schmidt, P.A.

[57] ABSTRACT

A menu driven reprogrammable drug pump is provided with a memory, such as flash memory, a display, a keyboard, and a communications port to allow a generic pump to be programmed with a desired pump application (therapy) program and patient specific settings. Programming and data transfer with another pump or a computer to and from the patient pump is by the communications port that allows local and/or remote communications with the pump. Flash memory stores the pump application program during use. Patient safety is provided by a cassette identification system, an occlusion detection system, and a latch/lock detection system. Automated testing of the pump is by a closed loop testing system.

35 Claims, 31 Drawing Sheets

U.S. PATENT DOCUMENTS

| | | |
|---|---|---|
| 3,923,060 | 12/1975 | Ellinwood, Jr. . |
| 3,942,526 | 3/1976 | Wilder et al. . |
| 3,985,133 | 10/1976 | Jenkins et al. . |
| 4,027,536 | 6/1977 | Heggie . |
| 4,080,967 | 3/1978 | O'Leary . |
| 4,091,550 | 5/1978 | Schrenk et al. . |
| 4,098,267 | 7/1978 | Stein et al. . |
| 4,137,913 | 2/1979 | Georgi . |
| 4,141,252 | 2/1979 | Lodge . |
| 4,146,029 | 3/1979 | Ellinwood, Jr. . |
| 4,174,637 | 11/1979 | Mulzet et al. . |
| 4,184,815 | 1/1980 | Casson et al. . |
| 4,191,184 | 3/1980 | Carlisle . |
| 4,210,138 | 7/1980 | Jess et al. . |
| 4,213,454 | 7/1980 | Shim . |
| 4,217,993 | 8/1980 | Jess et al. . |
| 4,236,880 | 12/1980 | Archibald . |
| 4,270,532 | 6/1981 | Franetzki et al. . |
| 4,279,188 | 7/1981 | Scott . |
| 4,280,136 | 7/1981 | Kashima et al. . |
| 4,299,218 | 11/1981 | Knigge et al. . |
| 4,299,541 | 11/1981 | Ohara et al. . |
| 4,308,866 | 1/1982 | Jelliffe et al. . |
| 4,309,993 | 1/1982 | Brown . |
| 4,311,377 | 1/1982 | Matteson . |
| 4,314,227 | 2/1982 | Eventoff . |
| 4,314,228 | 2/1982 | Eventoff . |
| 4,315,238 | 2/1982 | Eventoff . |
| 4,320,757 | 3/1982 | Whitney et al. . |
| 4,368,645 | 1/1983 | Glenn et al. . |
| 4,369,780 | 1/1983 | Sakai . |
| 4,370,983 | 2/1983 | Lichtenstein . |
| 4,373,525 | 2/1983 | Kobayashi . |
| 4,385,630 | 5/1983 | Gilcher et al. . |
| 4,385,958 | 5/1983 | Long . |
| 4,394,862 | 7/1983 | Shim . |
| 4,395,259 | 7/1983 | Prestele et al. . |
| 4,398,542 | 8/1983 | Cunningham et al. . |
| 4,410,322 | 10/1983 | Archibald . |
| 4,425,661 | 1/1984 | Moses et al. . |
| 4,431,425 | 2/1984 | Thompson et al. . |
| 4,446,344 | 5/1984 | Fiedler . |
| 4,460,355 | 7/1984 | Layman . |
| 4,484,479 | 11/1984 | Eckhardt . |
| 4,489,302 | 12/1984 | Eventoff . |
| 4,490,798 | 12/1984 | Franks et al. . |
| 4,493,704 | 1/1985 | Beard et al. . |
| 4,498,843 | 2/1985 | Schneider et al. ........................ 604/67 |
| 4,512,013 | 4/1985 | Nash et al. . |
| 4,520,706 | 6/1985 | Deforeit . |
| 4,526,574 | 7/1985 | Pekkarinen . |
| 4,529,401 | 7/1985 | Leslie et al. . |
| 4,530,696 | 7/1985 | Bisera et al. . |
| 4,534,756 | 8/1985 | Nelson . |
| 4,550,748 | 11/1985 | Nunez . |
| 4,557,725 | 12/1985 | Heyne et al. . |
| 4,559,038 | 12/1985 | Berg et al. . |
| 4,559,044 | 12/1985 | Robinson et al. . |
| 4,561,443 | 12/1985 | Hogrefe . |
| 4,563,179 | 1/1986 | Sakai . |
| 4,565,542 | 1/1986 | Berg . |
| 4,578,573 | 3/1986 | Flies et al. . |
| 4,597,754 | 7/1986 | Thill et al. . |
| 4,601,702 | 7/1986 | Hudson . |
| 4,606,353 | 8/1986 | Timm . |
| 4,617,014 | 10/1986 | Cannon et al. . |
| 4,623,331 | 11/1986 | Cewers et al. . |
| 4,624,661 | 11/1986 | Arimond . |
| 4,627,835 | 12/1986 | Fenton, Jr. . |
| 4,649,499 | 3/1987 | Sutton et al. . |
| 4,650,469 | 3/1987 | Berg et al. . |
| 4,652,260 | 3/1987 | Fenton, Jr. et al. . |
| 4,658,371 | 4/1987 | Walsh et al. . |
| 4,671,792 | 6/1987 | Borsanyi . |
| 4,676,776 | 6/1987 | Howson . |
| 4,681,563 | 7/1987 | Deckert et al. . |
| 4,685,903 | 8/1987 | Cable et al. . |
| 4,690,673 | 9/1987 | Bloomquist . |
| 4,696,671 | 9/1987 | Epstein et al. ........................... 604/67 |
| 4,710,163 | 12/1987 | Butterfield . |
| 4,714,462 | 12/1987 | DiDomenico . |
| 4,722,734 | 2/1988 | Kolln . |
| 4,731,051 | 3/1988 | Fischell . |
| 4,731,058 | 3/1988 | Doan . |
| 4,739,229 | 4/1988 | Heiler, Jr. . |
| 4,741,732 | 5/1988 | Crankshaw et al. . |
| 4,745,301 | 5/1988 | Michalchik . |
| 4,747,828 | 5/1988 | Tseo . |
| 4,754,401 | 6/1988 | Kaczynski et al. . |
| 4,756,706 | 7/1988 | Kerns et al. . |
| 4,774,029 | 9/1988 | Poulin . |
| 4,775,368 | 10/1988 | Iwatschenko . |
| 4,778,449 | 10/1988 | Weber et al. . |
| 4,785,799 | 11/1988 | Schoon et al. . |
| 4,790,816 | 12/1988 | Sundblom et al. . |
| 4,799,381 | 1/1989 | Tromp . |
| 4,808,161 | 2/1989 | Kamen . |
| 4,808,167 | 2/1989 | Mann et al. . |
| 4,810,992 | 3/1989 | Eventoff . |
| 4,816,019 | 3/1989 | Kamen . |
| 4,818,186 | 4/1989 | Pastrone et al. . |
| 4,832,033 | 5/1989 | Maher et al. . |
| 4,836,752 | 6/1989 | Burkett . |
| 4,838,856 | 6/1989 | Mulreany et al. . |
| 4,838,857 | 6/1989 | Strowe et al. . |
| 4,842,584 | 6/1989 | Pastrone . |
| 4,846,792 | 7/1989 | Bobo, Jr. et al. . |
| 4,847,990 | 7/1989 | Patrick . |
| 4,850,807 | 7/1989 | Frantz . |
| 4,852,581 | 8/1989 | Frank . |
| 4,856,339 | 8/1989 | Williams . |
| 4,863,425 | 9/1989 | Slate et al. . |
| 4,869,722 | 9/1989 | Heyman . |
| 4,878,896 | 11/1989 | Garrison et al. . |
| 4,882,575 | 11/1989 | Kawahara et al. . |
| 4,889,132 | 12/1989 | Hutcheson et al. . |
| 4,898,578 | 2/1990 | Rubalcaba, Jr. . |
| 4,908,017 | 3/1990 | Howson et al. . |
| 4,919,650 | 4/1990 | Feingold et al. ......................... 604/67 |
| 4,927,411 | 5/1990 | Pastrone et al. . |
| 4,933,873 | 6/1990 | Kaufman et al. . |
| 4,943,279 | 7/1990 | Samiotes et al. . |
| 4,950,235 | 8/1990 | Slate et al. . |
| 4,950,244 | 8/1990 | Fellingham et al. . |
| 4,961,533 | 10/1990 | Teller et al. . |
| 4,976,151 | 12/1990 | Morishita . |
| 4,978,335 | 12/1990 | Arthur, III .............................. 604/67 |
| 4,979,940 | 12/1990 | Bobo, Jr. et al. . |
| 4,994,035 | 2/1991 | Mokros . |
| 4,996,511 | 2/1991 | Ohkawa et al. . |
| 5,000,739 | 3/1991 | Kulisz et al. . |
| 5,006,997 | 4/1991 | Reich . |
| 5,010,473 | 4/1991 | Jacobs . |
| 5,017,059 | 5/1991 | Davis . |
| 5,034,004 | 7/1991 | Crankshaw . |
| 5,038,800 | 8/1991 | Oba . |
| 5,041,086 | 8/1991 | Koenig et al. . |
| 5,047,014 | 9/1991 | Mosebach et al. . |
| 5,053,585 | 10/1991 | Yaniger . |
| 5,053,990 | 10/1991 | Kreifels . |
| 5,062,774 | 11/1991 | Kramer et al. . |
| 5,074,756 | 12/1991 | Davis . |

| | | |
|---|---|---|
| 5,078,682 | 1/1992 | Miki et al. . |
| 5,078,683 | 1/1992 | Sancoff et al. . |
| 5,082,014 | 1/1992 | Olichney . |
| 5,084,828 | 1/1992 | Kaufman et al. . |
| 5,087,245 | 2/1992 | Doan . |
| 5,088,983 | 2/1992 | Burke . |
| 5,096,385 | 3/1992 | Georgi et al. . |
| 5,098,262 | 3/1992 | Wecker et al. . |
| 5,098,409 | 3/1992 | Stock . |
| 5,100,380 | 3/1992 | Epstein et al. . |
| 5,103,211 | 4/1992 | Daoud et al. . |
| 5,104,374 | 4/1992 | Bishko et al. . |
| 5,111,234 | 5/1992 | Taniguchi et al. . |
| 5,115,223 | 5/1992 | Moody . |
| 5,122,820 | 6/1992 | Pagano et al. . |
| 5,124,744 | 6/1992 | Ogura et al. . |
| 5,124,802 | 6/1992 | Ito et al. . |
| 5,131,816 | 7/1992 | Brown et al. . |
| 5,140,862 | 8/1992 | Pappalardo . |
| 5,153,827 | 10/1992 | Coutre et al. . |
| 5,154,700 | 10/1992 | Danby . |
| 5,172,698 | 12/1992 | Stanko . |
| 5,174,472 | 12/1992 | Raque et al. . |
| 5,176,004 | 1/1993 | Gaudet . |
| 5,181,910 | 1/1993 | Scanlon . |
| 5,190,522 | 3/1993 | Wojcicki et al. . |
| 5,207,642 | 5/1993 | Orkin et al. . |
| 5,211,626 | 5/1993 | Frank et al. . |
| 5,213,573 | 5/1993 | Sorich et al. . |
| 5,217,355 | 6/1993 | Hyman et al. . |
| 5,219,327 | 6/1993 | Okada . |
| 5,221,268 | 6/1993 | Barton et al. . |
| 5,224,051 | 6/1993 | Johnson . |
| 5,238,001 | 8/1993 | Gallant et al. . |
| 5,244,461 | 9/1993 | Derlien ........................................ 604/65 |
| 5,244,463 | 9/1993 | Cordner, Jr. et al. . |
| 5,256,157 | 10/1993 | Samiotes et al. . |
| 5,265,431 | 11/1993 | Gaudet et al. . |
| 5,317,506 | 5/1994 | Coutré et al. ............................ 604/65 |
| 5,338,157 | 8/1994 | Blomquist . |
| 5,354,273 | 10/1994 | Hagen . |
| 5,356,378 | 10/1994 | Doan . |
| 5,368,562 | 11/1994 | Blomquist et al. . |
| 5,376,070 | 12/1994 | Purvis et al. . |
| 5,383,855 | 1/1995 | Nicholson et al. . |
| 5,389,071 | 2/1995 | Kawahara et al. . |
| 5,389,078 | 2/1995 | Zalesky et al. . |
| 5,395,321 | 3/1995 | Kawahara et al. . |
| 5,431,627 | 7/1995 | Pastrone et al. . |
| 5,440,585 | 8/1995 | Partridge, III . |
| 5,456,691 | 10/1995 | Snell . |
| 5,485,408 | 1/1996 | Blomquist . |
| 5,531,697 | 7/1996 | Olsen et al. . |
| 5,531,698 | 7/1996 | Olsen . |
| 5,537,436 | 7/1996 | Bottoms et al. . |
| 5,594,786 | 1/1997 | Chaco et al. . |
| 5,616,121 | 4/1997 | McKay . |
| 5,647,854 | 7/1997 | Olsen et al. . |
| 5,658,250 | 8/1997 | Blomquist et al. ........................ 604/65 |
| 5,669,877 | 9/1997 | Blomquist . |
| 5,695,473 | 12/1997 | Olsen . |
| 5,717,603 | 2/1998 | McClendon et al. . |

FOREIGN PATENT DOCUMENTS

| | | |
|---|---|---|
| 0497041A1 | 8/1992 | European Pat. Off. . |
| 503670 | 9/1992 | European Pat. Off. . |
| 0371507B1 | 3/1993 | European Pat. Off. . |
| 551088 | 7/1993 | European Pat. Off. . |
| 0328162B1 | 12/1993 | European Pat. Off. . |
| 2603488 | 3/1988 | France . |
| 2675288 | 10/1992 | France . |
| 665 955 A5 | 6/1988 | Switzerland . |
| 2262452 | 6/1993 | United Kingdom . |
| WO87/07161 | 12/1987 | WIPO . |
| WO91/16609 | 10/1991 | WIPO . |
| 92/08647 | 9/1992 | WIPO . |
| 92/15439 | 9/1992 | WIPO . |
| 94/08647 | 4/1994 | WIPO . |
| WO95/25893 | 9/1995 | WIPO . |
| WO 97/25083 | 7/1997 | WIPO . |

OTHER PUBLICATIONS

Operator's manual for a CADD–Micro™ Ambulatory Infusion Pump Model 5900, front cover and pp. ii–vi and 1–84, copyright 1993.

Operator's manual for a CADD–PLUS® Ambulatory Infusion Pump Model 5400, two front cover pages, pp. iii–vi, pp. 1–55 and two back cover pages, copyright 1990.

Provider® One Instruction Manual, Pancretec, Inc. (undated).

"IV700 Service Manual." Valleylab, Inc., Boulder, Colorado; Sep. 1988.

Wilson, R., "Integrated Circuits" of Computer Design, pp. 26–27, Jun. 1, 1989.

Zales, S. et al., "Microprocessors and Microsystems", vol. 14, No. 8, pp. 543–549, Oct. 1990.

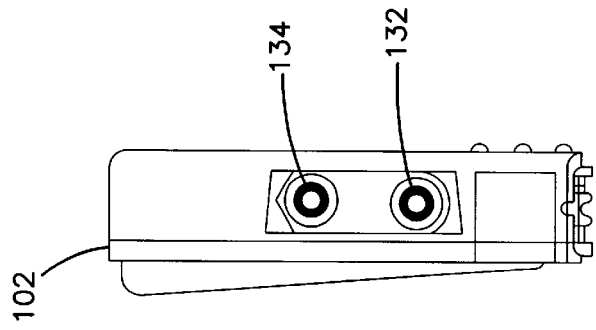
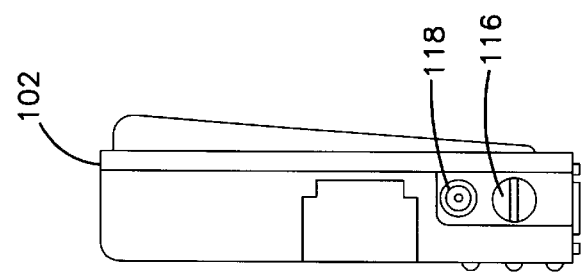
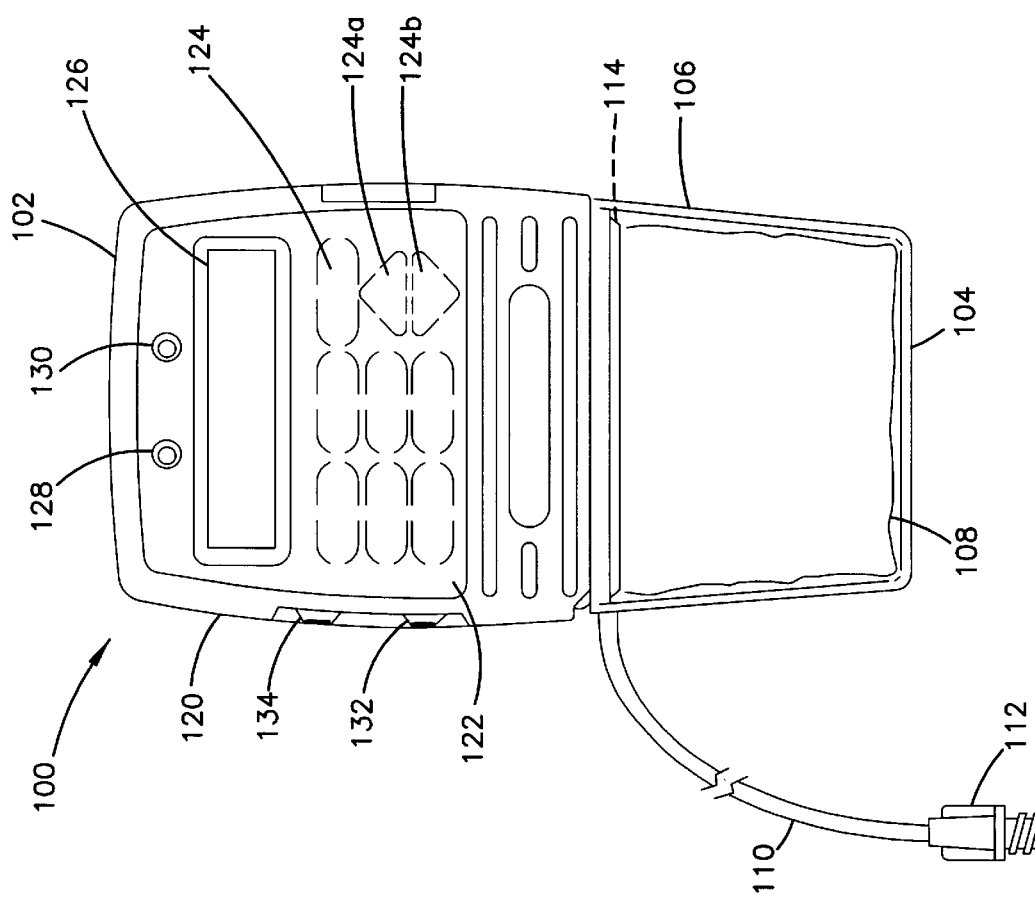

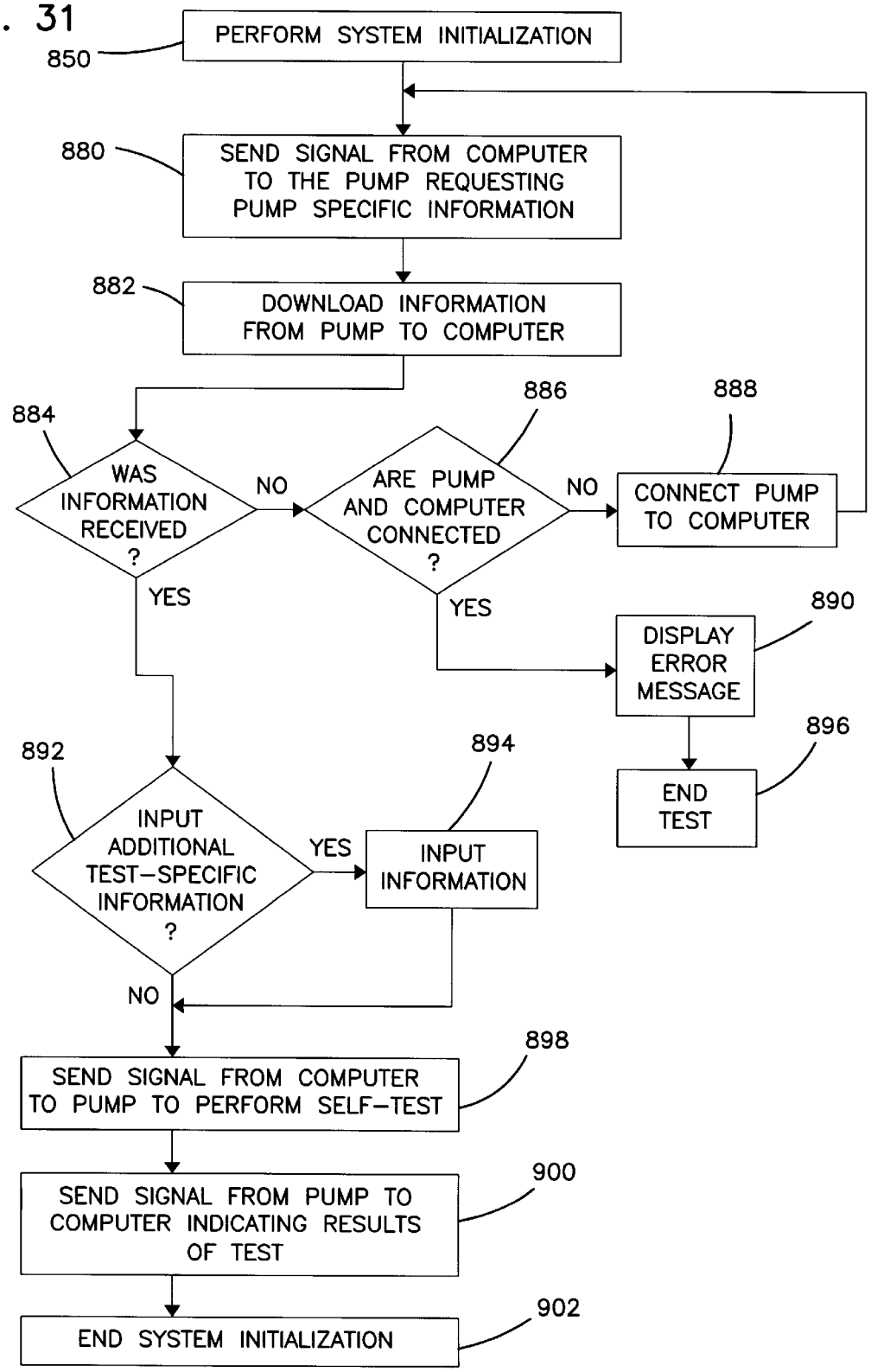

DRUG PUMP SYSTEMS AND METHODS

RELATED APPLICATIONS

The present application is a non-provisional of U.S. application Ser. No. 60/010,090 filed Jan. 12, 1996. The present application is also a continuation-in-part of U.S. application Ser. Nos.: 08/555,304 filed Nov. 8, 1995, now U.S. Pat. No. 5,658,250, which is a continuation of 08/090,738 filed Jul. 13, 1993, now abandoned; 08/206,737 filed Mar. 7, 1994 now U.S. Pat. No. 5,669,877; 08/586,952 filed Jan. 16, 1996, which is a continuation of 08/276,025, filed Jul. 15, 1994, now issued as U.S. Pat. No. 5,485,408, which is a continuation of 07/942,288 filed Sep. 9, 1992, now issued as U.S. Pat. No. 5,338,157; 08/561,809 filed Nov. 22, 1995; 08/540,960 filed Oct. 11, 1995; 08/618,574, filed Mar. 20, 1996, now U.S. Pat. No. 5,647,854, which is a continuation of 08/228,408, filed Apr. 15, 1994, now U.S. Pat. No. 5,531,697, and 08/281,179, filed Jul. 27, 1994, now U.S. Pat. No. 5,695,473.

FIELD OF THE INVENTION

The present invention relates to systems and methods for operating drug delivery devices, such as drug pumps.

BACKGROUND OF THE INVENTION

Various ambulatory medical devices are known for treating and/or monitoring patients at a remote site away from the caregiver's or clinician's office. One example of an ambulatory medical device is a drug delivery device, such as a drug pump, for providing periodic or continuous drug delivery to the patient when the patient is away from the caregiver's office.

Certain drugs rarely achieve their maximum therapeutic action through conventional injection techniques. Many drugs reach their full potential only through precise delivery over an extended period of time. With controlled drug infusion through a drug pump, the drug can be given at a precise rate that will keep the drug concentration within the therapeutic margin and out of the toxic range. Ambulatory drug pumps can provide appropriate drug delivery to the patient at a controllable rate which does not require frequent medical attention and which allows the patient to leave the hospital or caregiver's office.

A failure to adequately monitor the drug pump and the patient's usage of the drug pump can reduce or eliminate any benefits the patient may have received from a proper drug delivery therapy. In some cases, the drug therapies can have serious health consequences to the patient if the drugs are not administered properly.

Various concerns arise in connection with operation of the drug pumps. One concern arises in that the drug pump must be adequately monitored when the patient utilizes the drug pump at a remote site. Another concern relates to controlling the sophisticated therapies desired by the caregivers and the patients for the ambulatory drug pumps. Additional concerns relate to accurate pumping of an appropriate drug therapy. Still further concerns relate to the costs to manufacture and maintain the drug pump.

There is a need for drug pump operating systems and methods which address the above concerns and other concerns.

SUMMARY OF THE INVENTION

The present invention concerns a drug pump including a control module interconnectable to a cassette, the cassette being linked to a remote fluid reservoir or an enclosed fluid reservoir disposed within the cassette. The control module includes a pump mechanism for pumping fluid from the fluid reservoir to the patient. The control module includes a control system including a pump application program for providing a desired therapy, and patient specific settings accessed by the pump application program to deliver the particular therapy desired to the patient. The control system further includes a display and a keyboard. Preferably, a communications port is provided to transfer information to and from the drug pump. The drug pump is programmable to allow for different pump application programs for pumping different therapies to a patient, such as an antibiotic therapy, a chemotherapy, a pain control therapy, and a nutritional therapy.

Systems and methods are provided for communication between two drug pumps or between a drug pump and a computer. Further systems and methods are provided for simulating a pump, such as for training purposes. Systems and methods are further provided for reprogramming the pump application program including a flash memory resident within the control module. Systems and methods are also provided for identifying a cassette mounted to the control module. Systems and methods are further provided for automated testing of the pump systems, such as operation of the pumping mechanism.

BRIEF DESCRIPTION OF THE DRAWINGS

FIG. 1 is a first preferred embodiment of a drug pump including a control module and a drug cassette according to the present invention.

FIG. 1A is a right side view of the control module of FIG. 1 showing the latch and the lock for use in attaching the drug cassette to the control module.

FIG. 1B is a left side view of the control module of FIG. 1 showing the external power port and the communications port.

FIGS. 19–21, 24, 25 and 27 show portions of the control module and a first cassette. FIGS. 22 and 23 show a second cassette. FIG. 26 shows a third cassette.

FIG. 31 is a flow chart representation of the preferred steps taken during system initialization as identified in the flow chart of FIG. 30.

DESCRIPTION OF THE PREFERRED EMBODIMENTS

GENERAL OVERVIEW

Figure 2:
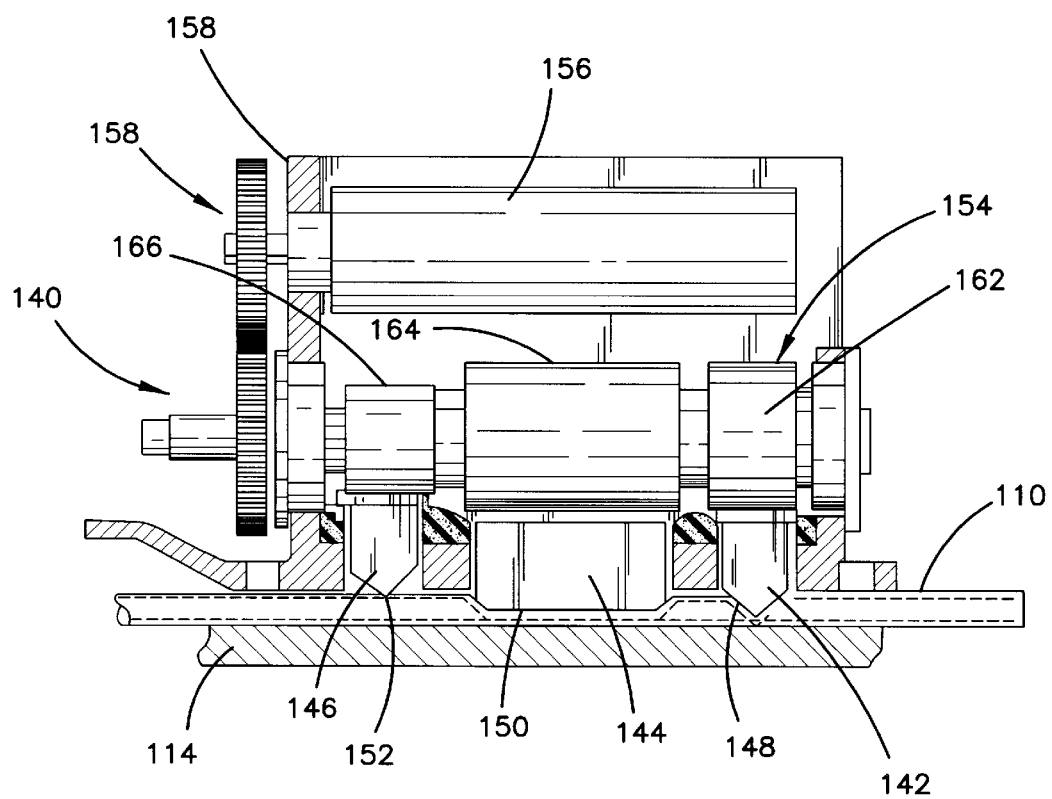
FIG. 2 is a side view of the pump mechanism of the control module of the drug pump of FIG. 1.

Referring now to FIG. 1, a drug pump 100 includes a control module 102 which is selectively mounted to a cassette or cartridge 104. Cassette 104 is shown as including an outer housing 106 with a fluid reservoir 108 disposed within outer housing 106. Extending from fluid reservoir 108 and positioned adjacent control module 102 is a tubing 110 which is connectable to a patient, such as by a Luer lock 112. Cassette 104 includes a pressure plate 114 which cooperates with a pump mechanism 140 (see FIG. 2) of control module 102 to pump fluid from fluid reservoir 108 through tubing 110 to the patient. In FIG. 1, fluid reservoir 108 is configured as a flexible fluid bag or pouch. Other fluid containers are possible. In addition, fluid reservoir 108 is shown contained within cassette 104. A remote fluid reservoir 108 separate from cassette 104 is possible.

In FIG. 1A, latch 116 of control module 102 is rotatably operated to securely latch cassette 104 to control module 102. Lock 118 is operable to prevent latch 116 from being unlatched, such as by an unauthorized person. In some drug therapies, a locking of cassette 104 to control module 102 is required.

Control module 102 includes an outer housing 120 containing within the control system and pump mechanism 140. Control module 102 includes a keyboard 122 with a plurality of keys 124 including up and down arrow keys 124a, 124b for scrolling. Tactile structures can be provided to assist a user in distinguishing the keys 124 by feel. Keyboard 122 permits entry of information to pump 100. Control module 120 further includes a display 126 for displaying information concerning operation of pump 100. Visual indicators 128, 130, such as amber and green LED indicators are provided with control module 120 to indicate various conditions of pump 100 to the patient or caregiver.

Referring now to FIG. 1B, a communications port 132 allows for communication with pump 100 from an external device located either locally or remotely relative to pump 100. An external power supply port 134 allows for connection of an external power supply to operate pump 100.

Pump 100 is an expulsor or peristaltic infusion pump which includes pump mechanism 140 as shown in FIGS. 2A–D. Pump mechanism 140 squeezes tubing 110 in a particular manner to achieve pumping of fluid from the reservoir to the patient. Pump mechanism 140 includes a reciprocally mounted inlet valve 142, a reciprocally mounted expulsor 144 downstream of inlet valve 142, and a reciprocally mounted outlet valve 146 downstream of expulsor 144. End 148 of inlet valve 142 is moved by pump mechanism 142 to alternately open and close tubing 110. End 150 of expulsor 144 is moved by pump mechanism 140 to compress tubing 110 to pump fluid and to allow expansion of tubing 110 following compression. End 152 of outlet valve 146 is moved to compress tubing 110 to alternately open and close tubing 110. A rotatable cam shaft 154 is rotated by motor 156 through gearing 158. The various components of pump mechanism 140 are supported by chassis 160 disposed within housing 120 of control module 102. Cam shaft 154 preferably includes three rotatable cams 162, 164, 166 configured as shown in FIG. 2.

Preferably, cam shaft 154 is constructed and arranged with double lobes (180° activation cycle) for each cam 162, 164, 166 for optimized energy consumption, such as described in U.S. Pat. No. 5,364,242, issued Nov. 15, 1994, the disclosure of which is incorporated herein by reference. Preferably, pump mechanism 140 is made in accordance with the methods described in U.S. Pat. No. 5,364,242. Other pump mechanisms are anticipated including finger style pump mechanisms, roller pump mechanisms, and other fluid pumping arrangements. Examples of further expulsor style infusion pumps are shown in U.S. Pat. Nos. 4,559,038; 4,565,542; 4,650,469; and 5,181,910, the disclosures of which are incorporated herein by reference.

Figure 3:
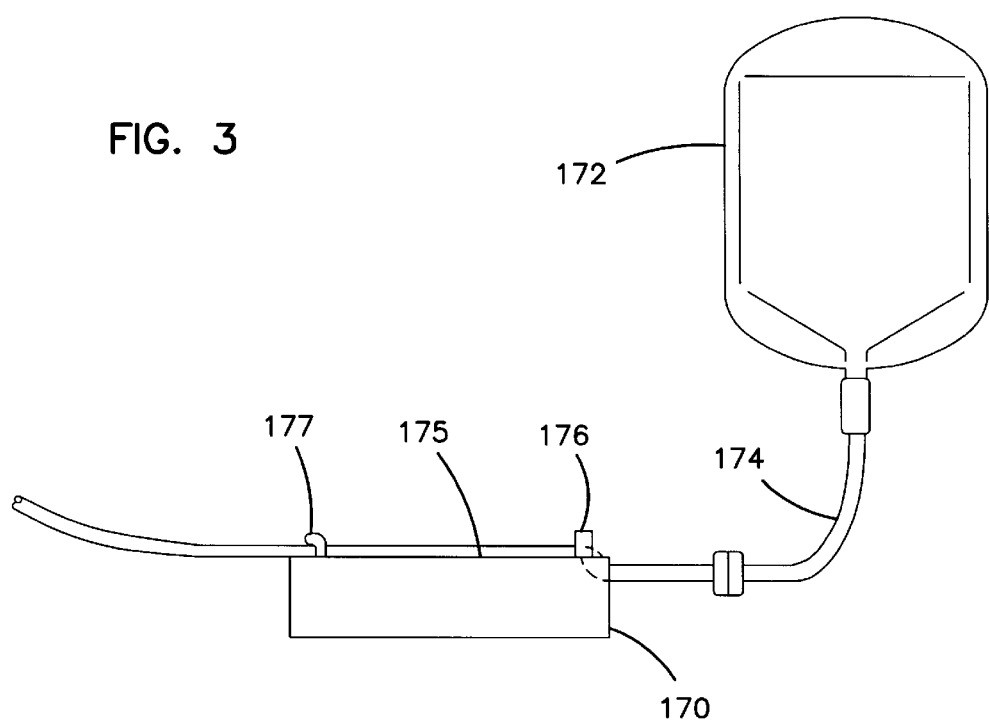
FIG. 3 is an alternative cassette (remote reservoir adapter) to the cassette shown in FIG. 1.

Referring now to FIG. 3, a remote reservoir adaptor 170 is shown which is mountable to control module 102 in a similar manner as cassette 104. However, instead of including a self-contained fluid reservoir 108, adaptor 170 is separate from remote fluid reservoir 172. Tubing 174 links remote fluid reservoir 172 to adaptor 170.

Both adaptor 170 and cassette 104 include an upper surface 175 with two extending hooks 177 and a loop 176 which permit releasable mounting to control module 102. See for example U.S. Pat. No. 4,565,542 previously incorporated by reference. Adapter 170 and cassette 104 may be both referred to as "cassettes." Hooks 177 engage a suspended pin assembly on control module 102 and loop 176 is engaged by latch 116 to mount the cassette to control module 102. Latch 116 in the latched state holds loop 176 so that the cassette cannot be pivoted away from control module 102 about an axis defined by hooks 177 and the suspended pin assembly.

Figure 4:
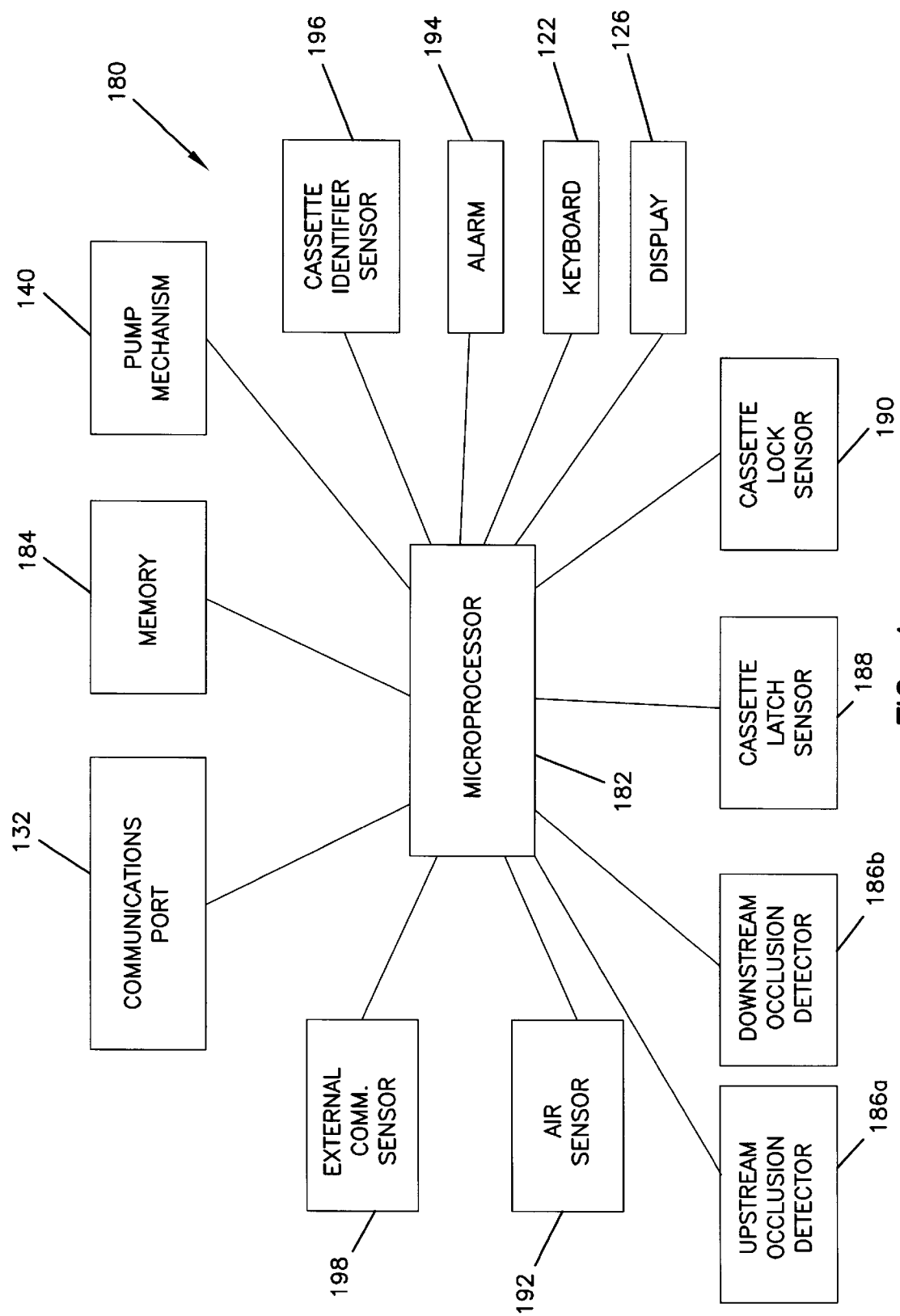
FIG. 4 is a schematic drawing of the control system of the drug pump of FIG. 1.

Referring now to FIG. 4, a schematic of a control system 180 of control module 102 is shown. Control system 180 controls the operation of pump 100. Control system includes a microprocessor 182 and a memory 184 programmable with selected functions for controlling operation of pump mechanism 140 and the other features of pump 100. Memory 184 can be a single memory internal to control module 102, or it can be a plurality of memory locations within control module 102. Control module 102 may also be designed and configured to accept one of a plurality of separate memory modules or memory cassettes containing information defining specific operational characteristics.

Specifically, memory 184 stores various programs and data related to the operation of pump 100. Memory 184 is coupled to microprocessor 182, which in turn runs the desired operating programs which control operation of pump mechanism 140. Stored in memory 184 is the program to permit communication with devices external to pump 100.

Access to microprocessor 182 is provided through communications port 132. Communications port 132 is preferably a standard RS232 communications port, although other communication links are possible (e.g., infrared telemetry). Information programmed into memory 184 instructs information to be transmitted or received via communications port 132. This feature allows information being received via communications port 132 from an external device to control pump 100. This feature also allows for the downloading of any or all information from memory 184 to an external device. An example of one type of device with which the pump 100 might communicate is described in U.S. patent application Ser. No. 08/561,809, which is entitled Pump Tracking System and was filed on Nov. 22, 1995, the disclosure of which is hereby incorporated by reference.

Control system 180 also includes keyboard 122 or other operator input structure for providing information to microprocessor 182. When a key 124 is pressed on keyboard 122, the key sends a signal to microprocessor 182 indicative of the key being pressed. Microprocessor 182 responds to the signal received in the desired manner. Other such input structures may include knobs, buttons, or other like structures for performing pump functions, such as starting, stopping, and priming pump 100.

Display 126 of control system 180 includes structure for displaying information to the patient or caregiver. A liquid crystal display ("LCD") may be provided. A 4-line×21 character alpha/numeric display capable of creating 5×7 pixel characters may be used. Display signals sent from microprocessor 182 permit display of information related to the operation of pump 100.

Pump 100 may also be provided with a variety of sensors, switches, or other devices (hereinafter "sensors"). The type of sensors provided depends on the type of pump and its intended usage. An example of such sensors include occlusion detectors 186a, 186b for detecting occlusions in tubing 110. Preferably, at least a downstream occlusion sensor 186b, such as a pressure or force sensitive sensor for sensing pressure in tubing 110 is provided, along with an associated CPU or hardwired circuitry. A silicon piezo resistive sensor is an example of occlusion detector 186b. Further examples of desirable sensors for pump 100 include a cassette latch sensor 188 for indicating whether the control module's latch is open or closed, a cassette lock sensor 190 for indicating whether the latch is locked, an air sensor 192 for detecting air in tubing 110, a cassette identification sensor 196, and an external communications cable sensor 198. The sensors typically send a suitable electrical signal to microprocessor 182 indicative of the condition sensed. Microprocessor 182 and memory 184 is appropriately programmed to receive and process such signals. In addition, pump 100 may also be equipped with alarm 194, such as a visual alarm (e.g., lights 128, 130 of FIG. 1) and/or an audible alarm (e.g. beeper) which is activated by the sensing of one of the conditions mentioned above, or other conditions. Alarm 194 may be activated as a result of other triggering events, such as error conditions with respect to the power supply or pump hardware. Alarm signals sent from microprocessor 182 permit activation of alarm 194.

Figure 5:
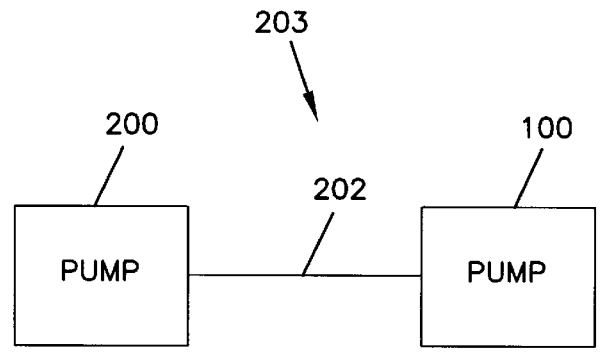
FIG. 5 is a schematic drawing showing pump to pump communication via a local or a remote link.
Figure 6:
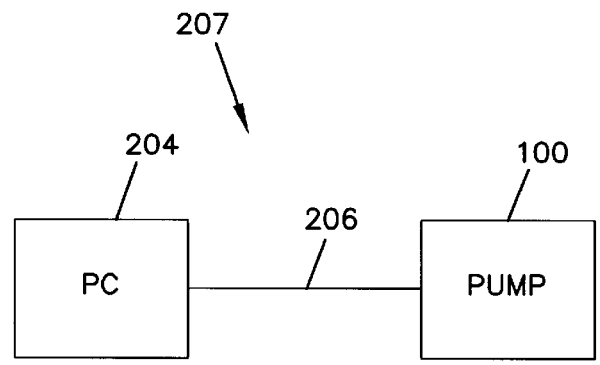
FIG. 6 is a schematic drawing showing communication between a pump and a computer system, such as a personal computer, over a local or a remote link.
Figure 7:
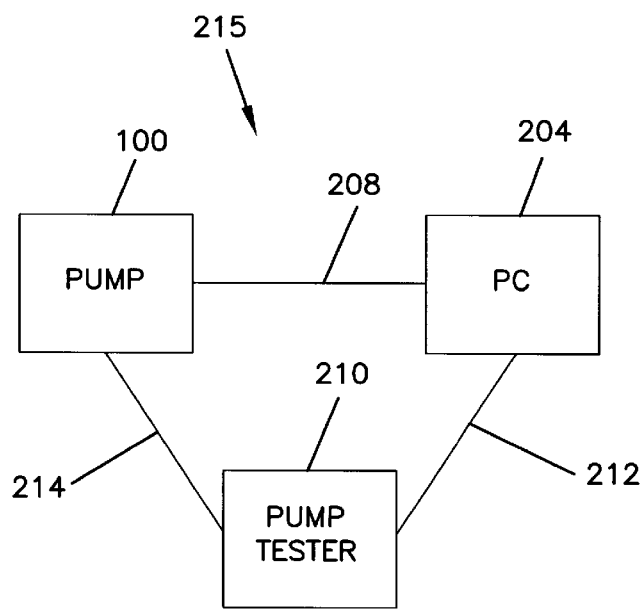
FIG. 7 is a schematic drawing showing a drug pump in a closed loop system for automated testing of the pump functions.

Referring now to FIGS. 5–7, various schematic drawings are shown illustrating possible uses of pump 100 in accordance with the present invention. In FIG. 5, pump 100 is shown linked to a second pump 200 via a communications link 202. Communications link 202 can be either a local link, or a remote link. Communication between pump 100, and second pump 200 is for a variety of purposes, including information transferred between a patient pump and a caregiver pump, such as in the event of an error condition, or a programming update, or a status update. The pump to pump communication system 203 of FIG. 5 is useful to allow convenient communication with a functional patient pump 100.

Referring now to FIG. 6, pump 100 is linked to a computer system 204, such as a personal computer, via communications link 206, either locally or remotely. Pump to computer system communication system 207 of FIG. 6 is useful for transferring information between a functioning patient pump 100 and the computer system 204.

Referring now to FIG. 7, pump 100 is shown linked to computer system 204 and also to pump tester 210. An information transfer link is provided by communications link 208 between pump 100 and computer system 204. An information transfer link between pump tester 210 and computer system 204 is provided via communications link 212. A fluid line 214 between pump 100 and pump tester 210 provides a closed loop system 215 for automated testing of a functioning patient pump 100.

Figure 8A:
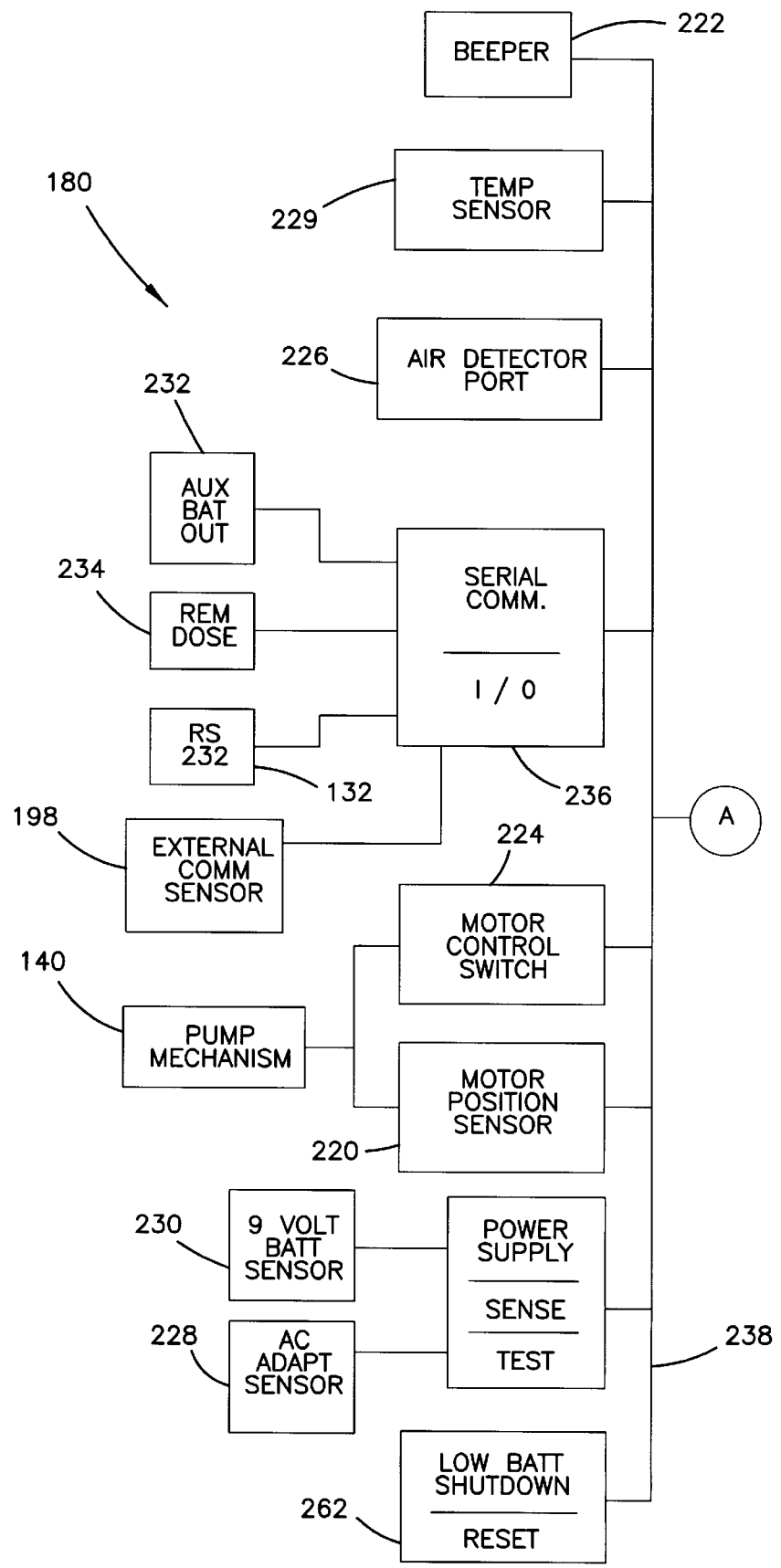
FIGS. 8A and 8B together show a more detailed block diagram of the control system of FIG. 4 for the pump shown in FIG. 1.

Referring now to FIGS. 8A and B, a more detailed block diagram for control system 180 of pump 100 is shown. In addition to the features of control system 180 described above, see for example FIG. 4, control system 180 also includes various other sensors, switches, or devices needed or useful in operating the various features of pump 100.

A motor position sensor 220 is provided for monitoring the position of the motor of the pumping mechanism. An appropriate signal is generated by sensor 220 and communicated to microprocessor 182.

Beeper 222 provides an audible signal at the desired time to the user of pump 100. An appropriate signal from microprocessor 182 activates beeper 222 at the appropriate time.

External communication sensor 198 senses when a communications cable connection or powered external serial device connection is made with respect to pump 100 at communications port 132. An appropriate signal is generated by external communication sensor 198 and sent to processor 182 indicative of the connection and/or the lack of connection with the communications cable or other connection device. Such connection can automatically trigger events in pump 100, such as initiation of pump to pump communications operation. Optionally, external communication sensor 198 can sense when a remote dose cord is attached, or when a remote data gathering device (e.g., temperature sensor, blood pressure monitor, EKG monitor, or respiratory monitor) is attached. The remote dose cord can also be used by the patient as an event marker for storage in pump memory 184. For example, the patient can note with the remote dose cord a nauseous condition.

Motor control switch 224 turns on and off the motor of pump mechanism 140 at the desired time based upon signals sent from microprocessor 182. Pump 100 can be intermittently operated a predetermined number of times at predetermined intervals according to the pump operations program provided to control system 180. These intervals can range from once every couple of seconds or less to as long as a couple of times an hour or more.

Air detector port 226 allows the plug in of an appropriate external sensor to sense air in the fluid conduit between the reservoir and the patient. A sensor may be provided to sense when the air sensor is attached, or when the door to the port is removed.

AC adapter sensor 228 senses when an AC adapter has been plugged into pump 100 such that the pump is then powered by the alternating current power supply or a battery pack.

Temperature sensor 229 senses the temperature to provide an input to the pump operating program to increase the accuracy of the pressure sensor. Tube compression properties can be affected by the ambient air temperature.

Battery sensor 230 senses the presence of a battery supply, such as a nine volt battery. Battery sensor 230 also senses when the battery supply is low.

Auxiliary battery output port 232 is provided for supplying a source of power to an external accessory of pump 100 from the power supply of pump 100.

Remote dose cord port 234 permits interconnection of a remote dose cord arrangement to pump 100. The remote dose cord arrangement permits the patient to remotely press or simulate pressing a key on keyboard 122, such as the key which manually operates the pumping mechanism, via a signal from a remote switch sent through remote dose cord port 234 to processor 182. A signal generated by an appropriate sensor at port 234 is sent to microprocessor 182 to indicate to microprocessor 182 that the remote dose cord is connected to pump 100.

A serial communication device 236 is provided for controlling communications access with auxiliary battery output port 232, remote dose cord port 234, communications port 132, and sensor 198 in a serial manner.

Pump mechanism 140 is illustrated as being controlled by motor control switch 224 and monitored by motor position sensor 220. Pump mechanism 140 is responsible for pumping fluid from the reservoir to the patient. As noted above, one possible pumping mechanism includes a rotatable cam shaft with tube engaging followers reciprocally mounted to move as the cam shaft rotates.

The various sensors, switches, and devices in control system 180 generate and/or receive an appropriate signal or signals during communication with microprocessor 182 during operation of pump 100. Microprocessor 182 is electrically interconnected through an appropriate interface bus 238 with all of the various sensors, switches, and other devices of pump 100. Microprocessor 182 responds to input signals by generating appropriate control output signals in accordance with the program control logic stored in memory. One preferred microprocessor 182 that may be used in connection with pump 100 is an MC68HC11E9 high-density complimentary metal-oxide semiconductor (HCMOS) high performance microcontroller unit (MCU) by Motorola. Such processor includes 512 bytes of electrically erasable programmable read only memory (EEPROM), and 512 bytes of random access memory (RAM).

Microprocessor 182 is further electrically interconnected to a flash memory 240, an electrically erasable programmable read only memory (EEPROM) 242 and a static random access memory (RAM) 244. A real time clock 246 is also provided. Battery 248, such as a lithium cell, provides a power supply to the real time clock 246 and the static RAM 244.

Microprocessor 182, flash memory 240, EEPROM 242, static RAM 244, gate array 257, real-time clock 246, and parallel input/output means 258 comprise at least a part of the processor control circuitry of control system 180.

Figure 8B:
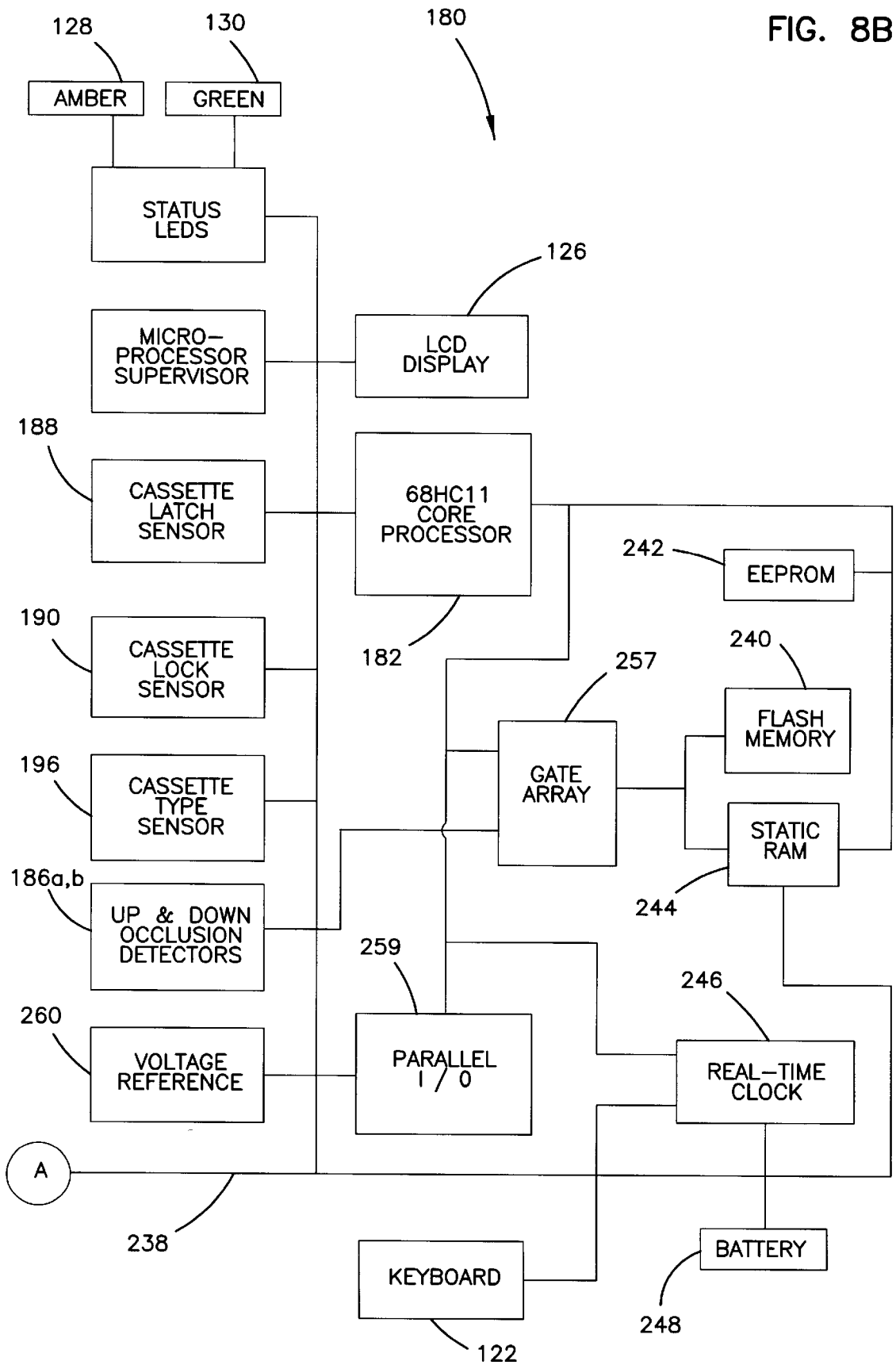

As shown in FIG. 8B, a voltage reference 260 is provided as part of control system 180 in the preferred embodiment. As shown in FIG. 8A, a low battery shutdown and reset device 262 is provided in control system 180 in the preferred embodiment.

The pump system software includes software designed to reside inside the pump as well as software designed to run on a personal computer (PC). The pump is a hardware platform designed to support a variety of software which implements different infusion modes, as well as other utility features. In addition, the pump can communicate with accessory PC programs, either via a direct serial connection, over phone lines using a modem, or other communication methods. The system software includes executable programs such as pump software programs which implement an infusion mode (also called "applications"); pump software programs which implement something other than an infusion mode (also called "utilities"); and pump software which handles power-up control (also called "the boot system").

The pump applications also can provide different infusion modes including, but not limited to:

1) An infusion mode consisting of a basal-rate delivery superimposed with patient demand doses (suitable for Patient Controlled Analgesia (PCA) pain control therapy, etc.).

2) An infusion mode consisting of a large volume delivered over a period of time during which the delivery rate first linearly increases, then stays constant, and finally linearly decreases (suitable for Total Parenteral Nutrition (TPN) intravenous nutritional therapy, hydration therapy, etc.).

3) An infusion mode consisting of constant-amount automatic doses repeated at regular intervals (suitable for intermittent delivery therapies such as antibiotic therapy, etc.).

4) An infusion mode consisting of a constant rate (suitable for a wide variety of continuous delivery therapies such as chemotherapy, etc.).

The pump applications/utilities and boot system also can provide features in addition to infusion modes including, but not limited to:

1) A feature to switch from one infusion mode to another, and to load new pump software programs under external control via a direct serial connection or other communication methods.

2) A feature to run diagnostic functions which can be used to test the operation of the pump hardware under external control via a direct serial connection or other communication methods.

3) A feature to allow an application running in the pump to be externally controlled via a remote serial connection or other connection, in order to troubleshoot the pump or monitor and adjust a patient's therapy.

4) A feature to control an application running in another pump via a remote serial connection or other connection, in order to troubleshoot the pump or monitor and adjust a patient's therapy.

The PC software programs can interface to a pump via a serial connection or other connection, and provide features including, but not limited to:

1) A feature to load pump software programs into a pump, via a direct serial connection or other connection to software running in the pump.

2) A feature to test a pump's hardware, via a direct serial connection or other connection to software running in the pump.

3) A feature to troubleshoot a pump or monitor and adjust a patient's therapy, via a remote serial connection or other connection to an application running in the pump.

SOFTWARE OVERVIEW

Desirable software of one preferred pump operating system and method includes software: for controlling pump power up; for implementing the pump application necessary to pump fluid to the patient; for implementing a master mode communication sequence between two pumps; for implementing a communication sequence between a PC and a patient pump; for testing the pump hardware; for controlling the pump hardware testing; and for changing resident pump applications and utilities using a PC.

The pump software controls the pump after a power-up or power-on reset. Various inputs, processing features, and outputs are provided:

Inputs
1) Motor position sensor signals
2) Serial cable connect signal
3) Serial messages
4) Watchdog signal
5) Latch and lock sensor signals
6) Real-time clock data and signals
7) Manufacturing parameters
8) Program look-up table data
9) Launch program data Processing Features
1) Initialize the microprocessor and configure the system.
2) Perform power-up and run-time hardware self-tests necessary for its own safe operation.
3) Keep the hardware watchdog circuit from timing out.
4) Display an error code on the LCD upon detecting an error in a hardware self-test, store the error code, and halt further execution with the device in a safe-state.
5) Give visual notification that the software is executing (i.e. alive) within 5 seconds after hardware reset.
6) Display status messages on the LCD, including but not limited to the following indications:
   The pump model
   The hardware ID and the last error code which was logged.

The program ID of the current launch program.
The program IDs of all installed applications.

7) Operate in one of two modes: launch mode, in which an application or utility is automatically executed; and command mode, in which it shall receive command messages via the serial port and send status messages.
8) In launch mode, begin execution of the launch program or the hardware testing software within 35 seconds.
9) In command mode, determine if it is connected serially to a PC testing station, and if so, launch the pump testing utility.
10) In command mode, display status messages on the LCD, including but not limited to indications that:
    No applications or utilities exist in memory
    The pump has established communications with a PC
    A program download is in progress
    A program download has been completed
    A program download has failed or been interrupted
11) In command mode, provide means to report which application or utility is currently the launch program via the serial port.
12) In command mode, provide means to report which programs exist in memory and to verify the integrity of any program via the serial port.
13) In command mode, provide means to retrieve the manufacturing parameters via the serial port.
14) In command mode, provide means to receive an application or utility program via the serial port and load it into memory.
15) In command mode, provide means to receive the manufacturing parameters via the serial port and program them into memory. Also provide means to receive the time and date via the serial port and store it into the real-time clock.
16) In command mode, provide means to enable or disable an application or utility which exists in memory via the serial port. It is preferred not to be able to launch a disabled program.

Outputs
1) Audible indicator control signals
2) Visual indicator control signals
3) Display text
4) Watchdog strobe signal
5) Latch and lock sensor power control signals
6) Disposable type sensor power control signals
7) Serial messages
8) History log data
9) Error log data
10) Manufacturing parameters
11) Program look-up table data
12) Launch program data
13) Flash ROM program slots
14) Motor spike flag The pump software implements different infusion modes or applications. Various inputs, processing features, and outputs are provided:

Inputs
1) Key presses
2) Auxiliary input signals/remote dose signals
3) Power source sensor signals
4) Motor position sensor signals
5) Serial cable connect signal 6) Serial messages 7) Latch and lock sensor signals 8) Disposable type sensor signals 9) Air-in-line sensor signals 10) Pressure sensor signals 11) Voltage reference signal 12) Real-time clock data and signals 13) Delivery, status, and configuration parameters.

Processing Features

1) Perform power-up and run-time hardware self-tests necessary for its own safe operation.

2) Keep the hardware watchdog circuit from timing out.

3) Display an error code on the LCD upon detecting an error in a hardware self-test, store the error code, and halt further execution with the device in a safe-state.

4) Provide means to input delivery parameters appropriate for the infusion mode.

5) Keep status parameters appropriate for the infusion mode.

6) Provide means to input configuration parameters appropriate for the infusion mode.

7) Control the pumping mechanism to implement the infusion mode.

8) Monitor hardware sensor input signals.

9) Issue audible and/or visual alarms to indicate certain conditions or occurrences to the user.

10) Provide means to determine which other programs exist in memory, and to switch to another program.

11) Send and receive messages through the serial port.

12) Include a slave mode of operation during which it is controlled via a remote serial connection, by processing received keypress messages and sending display update messages.

13) In slave mode, receive serial command messages, and send serial status messages for the following data: event history, error history, current delivery, status, and configuration parameters, automatic odometers, and manufacturing parameters. Allow for random access to the delivery, status, and configuration parameters, send serial paging messages to another remote pump, and respond to serial paging messages from the remote pump.

Outputs

1) Audible indicator control signals

2) Visual indicator control signals

3) Display text

4) Motor control signals

5) Watchdog strobe signal

6) Latch and lock sensor power control signals

7) Disposable type sensor power control signals

8) Air-in-line sensor test signal

9) Serial messages

10) Real-time clock data

11) Delivery, status, and configuration parameters

12) History data

13) Error log data

14) Automatic odometer data

15) Manufacturing parameters

Pump software is provided to implement a master mode of operation, during which one pump controls a pump application in another pump via a remote serial connection by sending keypress messages and receiving display update messages. Various inputs, processing features, and outputs are provided:

Inputs

1) Key presses

2) Power source sensor signals

3) Serial cable connect signal

4) Serial messages

5) Watchdog signal

6) Real-time clock data and signals

Processing Features

1) Perform power-up and run-time hardware self-tests necessary for its own safe operation.

2) Keep the hardware watchdog circuit from timing out.

3) Display an error code on the LCD upon detecting an error in a hardware self-test, store the error code, and halt further execution with the device in a safe-state.

4) Send serial keypress messages to another remote pump, and process received serial display update messages.

5) Send command messages to an external modem to initialize it and control its operation.

6) Provide means to send serial paging messages to another remote pump, and respond to serial paging messages from the remote pump.

Outputs

1) Audible indicator control signals

2) Visual indicator control signals

3) Display text

4) Watchdog strobe signal

5) Serial messages

6) Error log data

7) History log data

PC software is provided which controls a pump application via a remote serial connection. Various inputs, processing features and outputs are provided:

Inputs

1) Keyboard input

2) Mouse input

3) Serial messages

4) Real-time clock

5) Automatic Odometer data

6) Manufacturing parameters

Processing Features

1) Provide a graphical representation of a pump on the PC screen which has keys that can be activated using a mouse.

2) Send serial keypress messages to a remote pump, and process received serial display update messages by updating the pump displayed on the PC screen.

3) Provide means to send serial command messages to a remote pump, and store received status messages to disk for the following data: history log, error log, current delivery, status, and configuration parameters, program ID, program name, program description, serial number, and hardware ID.

4) Provide means to send serial messages which allow random access to a remote pump's delivery and status parameters. Provide means to send serial paging messages to another remote pump, and respond to serial paging messages from the remote pump.

5) Provide means to display a representation of event history status messages.

6) Provide means to print data retrieved from the pump, and retrieve and print data stored on disk.
7) Operate without requiring knowledge about the application running on the remote pump.

Outputs
1) Audible indicator control signals
2) Display information
3) Serial messages
4) Real-time clock data
5) Disk files Pump software is provided which allows the pump hardware to be tested via a direct serial connection. Various inputs, processing features and outputs are provided:

Inputs
1) Keyboard input
2) Auxiliary input signals
3) Power source sensor signals
4) Motor position sensor signals
5) Serial cable connect signal
6) Serial messages
7) Latch and lock sensor signals
8) Disposable type sensor signals
9) Air-in-line sensor signals
10) Pressure sensor signals
11) Voltage reference signal
12) Real-time clock data and signals
13) History log data
14) Error log data Processing Features
1) Perform power-up and run-time hardware self-tests necessary for its own safe operation.
2) Keep the hardware watchdog circuit from timing out.
3) Process received serial command messages, and send serial status messages.
4) Provide means to pump at a specified rate or deliver a bolus of a specified volume.
5) Provide means to detect a high pressure condition.
6) Provide means to perform hardware self-tests, and report the results on the display or via serial messages.
7) Provide means to perform additional interactive diagnostic hardware tests. (e.g. for the keypad, display, beeper, disposable sensors, and air-detector).
8) Provide means to perform an interactive, non-recoverable motor safety circuit check.

Outputs
1) Audible indicator control signals
2) Visual indicator control signals
3) Display text
4) Motor control signals
5) Watchdog strobe signal
6) Latch and lock sensor power control signals
7) Disposable type sensor power control signals
8) Air-in-line sensor test signal
9) Serial messages
10) Real-time clock data
11) Delivery, status, and configuration parameters
12) History log data
13) Error log data PC software is provided which controls pump hardware testing via a direct serial connection. Various inputs, processing features, and outputs are provided:

Inputs
1) Key presses
2) Mouse presses
3) Serial messages

Processing Features
1) Communicate with a pump via a serial link.
2) Provide means to query a pump for diagnostic information.
3) Provide means to instruct a pump to perform hardware and functional tests.
4) Control an infusion pump analyzer.
5) Provide means to print and store to disk the results of pump hardware tests.

Outputs
1) Audible indicator control signals
2) Display text
3) Serial messages
4) Disk files PC software is provided which changes resident pump applications and utilities via a direct serial connection. Various inputs, processing features, and outputs are provided:

Inputs
1) Keyboard input
2) Mouse input
3) Serial messages
4) Disk files
5) Manual or electronic order-entry information Processing Features
1) Send command messages to a pump through the serial port and receive status messages back.
2) Query a pump to determine its serial number and which applications and utilities reside in the pump by program ID.
3) Provide means to read application or utility software from a disk file, instruct a pump to load the program into a certain program slot, and send it to the pump.
4) Provide means to instruct a pump to enable/disable a certain application or utility.
5) Maintain pump-tracking information disk files which list all application-changing activities by pump serial number.
6) Display status messages when communicating with a pump and loading a program.
7) Provide means to input the manufacturing parameters, instruct the pump to store the data, and send it to the pump.
8) Provide means to load pump programs corresponding to order-entry information.

Outputs
1) Audible indicator control signals
2) Display text
3) Serial messages
4) Disk files
5) Manual or electronic pump-tracking information

PUMP TO PUMP COMMUNICATION SYSTEMS AND METHODS

Figure 9:
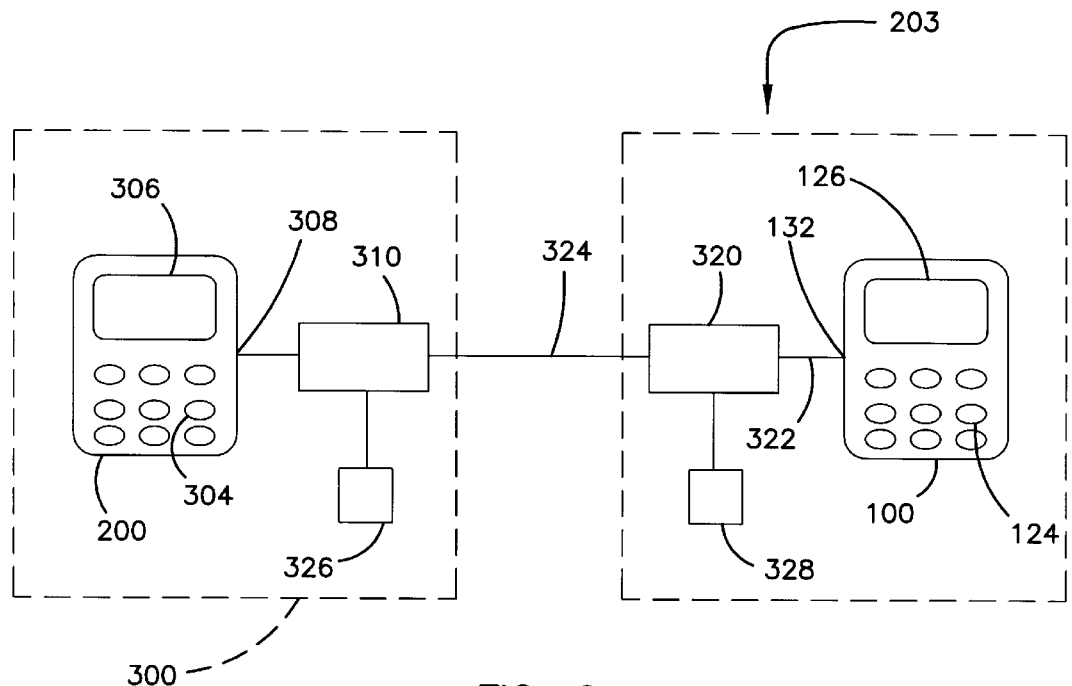
FIG. 9 is a schematic drawing illustrating the pump to pump communication system of FIG. 5 in greater detail.

Referring now to FIG. 5 generally, and to FIG. 9 specifically, a system 203 of communication between a local drug pump 200 (or caregiver pump) and a remote drug pump 100 (or patient pump) is shown. In system 203, local pump 200 is functioning as a caregiver pump for use by the caregiver at the site 300 where the caregiver is located, such as the caregiver's office. Site 300 may be the caregiver's home, during on call periods, or even the caregiver's automobile, if the automobile is provided with some communications capability for sending and receiving signals with respect to another site. In system 203, the caregiver operating pump 200 is typically a nurse, physician, therapist, or other medical personnel.

In system 203, remote pump 100 is functioning as an ambulatory patient pump for pumping drugs to the patient and is located with the patient at a site remote from caregiver pump 200, such as at the patient's home 302. Also, site 302 may be the patient's workplace.

Pumps 100, 200 each include a pumping mechanism which is capable of pumping fluid from a fluid reservoir to a patient. Specific components of patient pump 100 are shown in greater detail in FIGS. 1–4 and 8. Caregiver pump 100 is preferably identical to patient pump 200 with respect to the features shown in FIGS. 1–4 and 8.

Both caregiver pump 200 and patient pump 100 can be utilized for pumping or delivering a drug to a patient when the respective pump is interconnected to the patient. Pumps 100, 200 are preferably identical with respect to the electrical and the mechanical fluid pumping functions. One advantage of this is that caregiver pump 200 can be an unused spare patient pump 100. As will be discussed below, the respective control systems of pumps 100, 200 may be programmed differently to operate in the appropriate desired manner during pump to pump communications. As will also be discussed, this programming can be done locally or remotely. Preferably, pumps 100, 200 include appropriate programs to operate either as a master pump or as a slave pump during pump to pump communications. In some cases, the programs in each pump that control operation of the pumping mechanism will be different. This will also be discussed in more detail below.

Pumps 100, 200 each include operator input structure for permitting an operator of the respective pump to communicate with the control system of the pump, specifically the internal processor of the pump and the information in the internal memory. In the preferred embodiment, a plurality of operator keys 304 on caregiver pump 200 are provided for pressing by the caregiver. Preferably, each key has at least one function. Keys 304 send a signal to the control system of caregiver pump 200 indicative of the key pressed by the caregiver. The control system of pump 200 responds in the desired manner if an acceptable key press is made by the caregiver.

Patient pump 100 has keys 124 preferably identical to keys 304. Keys 124 send a signal to the control system of patient pump 100 indicative of the key pressed. The control system of patient pump 100 responds in the desired manner if an acceptable key press is made by the patient.

Caregiver pump 200 includes a display 306 for displaying selected information stored in the control system. In one preferred embodiment, display 306 includes an LCD dot matrix display. LCD dot matrix display 306 is interconnected to the control system of caregiver pump 200. Display signals sent from the control system of caregiver pump 200 permit display of information related to operation of pump 200 on display 306.

Patient pump 100 has a display 126 preferably identical to display 306 of caregiver pump 200. Display signals sent from the control system of patient pump 100 display information related to operation of pump 100 on display 126.

Communication port 308 of caregiver pump 200 permits interconnection of the control system of caregiver pump 200 to a modem 310 located locally with respect to caregiver pump 200. Caregiver pump 200 is interconnected to modem 310 through connection structure 312, such as an RS232 serial cable. Caregiver pump 200 and modem 310 may be located at the caregiver's office 300, at the caregiver's home during on-call periods, or even at a mobile site, such as the caregiver's automobile.

Communication port 132 permits interconnection of the control system of patient pump 100 to modem 320 with connection structure 322, such as an RS232 serial cable. Patient pump 100 and modem 320 are both located remotely to caregiver pump 200 and modem 310, such as at the patient's home or workplace 302, or other location remote from caregiver pump 200.

Communication between pump 200 and pump 100 through modems 310, 320 is over communications medium 324 such as conventional telephone lines, cellular phones, fiber optics links, satellite links, microwave links, or other links. Modems 310, 320 preferably communicate at 9600 bps and include error correction and data compression features over conventional telephone lines.

One advantage of the present invention is that the caregiver can communicate with the patient pump 100 using a similar pump, the caregiver's pump 200. The caregiver presumably has knowledge of operation of patient pump 100. This knowledge is useful in utilizing caregiver pump 200 to communicate with patient pump 100 to access the processor of patient pump 100 from a remote location.

Communication between the control system of the remote patient pump 100 and the control system of the local caregiver pump 200 permits remote data gathering from the remote patient pump by the local caregiver pump. Such data gathering may be useful for periodic monitoring of the patient pump 100 during use of the patient pump at the remote site. Data gathering may also be useful at the end of the patient use.

Communication between the remote patient pump 100 and the local caregiver pump 200 permits troubleshooting with respect to the remote patient pump, without the caregiver being located at the same location as the patient's pump. Remote troubleshooting is useful in the case where patients are unfamiliar with the some of the more sophisticated operations of their pump. Also, remote troubleshooting using the pump to pump communication system is useful for patients who have difficulty orally communicating with the caregiver over the telephone.

Communication with the remote patient pump 40 is also useful for accessing the pump operations programs for changing or adjusting the operation of the remote patient pump from the local site, thereby saving the caregiver and the patient time from not having to make an in-person visit.

Information programmed into the control system of the caregiver pump 200 permits the caregiver pump 200 to be put into a master mode from the normal pumping mode at the appropriate time. In the master mode, caregiver pump 200 sends a keyboard input signal indicative of a key 304 pressed by the caregiver over port 308 to patient pump 100. In the master mode, caregiver pump 200 receives its display signals primarily from patient pump 100 via communication port 308. In the master mode, the key presses on keys 124 of caregiver pump 200 do not access the memory of caregiver pump 200 for the purposes of programming the memory of caregiver pump 200 or selecting information for display relating to caregiver pump 200. The master mode is primarily for permitting caregiver pump 200 to communicate with the controller of patient pump 100 for the purposes of programming the memory of patient pump 100 or selecting information for display relating to patient pump 100 from the memory of patient pump 100. The master mode is carried out by a terminal application program in pump 200.

With respect to patient pump 100, information programmed into its control system permits patient pump 100 be put into a slave mode from the normal pumping mode at the appropriate time. In the slave mode, patient pump 100 receives keyboard input signals primarily from caregiver pump 200 via communication port 132. Patient pump 100 sends its display signals from communication port 132 to caregiver pump 200.

To communicate between caregiver pump 200 and patient pump 100 over modems 310, 320, caregiver pump 200 is out of the normal pumping mode and in the master mode. Similarly, patient pump 100 is out of the normal pumping mode and in the slave mode. In some cases, control systems with sufficient capacity may be provided where the pumps 200, 100 operate simultaneously in the normal pumping mode and in the master or slave modes.

In system 203, patient pump 100 is at least programmed to be operable in two modes, the normal pumping mode and the slave mode. There typically is not a need for patient pump 100 to operate in the master mode when the patient possesses the patient pump. Further, in system 203, caregiver pump 20 is at least operable in the master mode. However, situations are anticipated where it is desirable to have one or both pumps 100, 200 include programs for operation in the normal pumping mode, the slave mode, and the master mode. In some cases, caregiver pump 200 may be an unused patient spare. At a later date, the unused patient spare may be needed as a patient pump. This would require the slave mode operating program, and a particular normal operation mode program suitable for the patient. It may be more efficient for the caregiver if the controller of each pump 100, 200 is preprogrammed to include both the master mode program and the slave mode program. The selection of master or slave mode may be made by the caregiver by preconfiguring the patient's pump 100 to enter the slave mode during pump to pump communication, and not enter the master mode. The caregiver would have the capability to preconfigure the caregiver pump 200 to only enter the master mode during pump to pump communication, and not the slave mode if the caregiver desired. At some point later in time, the caregiver could reconfigure the caregiver pump 200 to only enter the slave mode during pump to pump communications if the caregiver pump 200 was needed as a patient pump.

In system 203 of FIG. 9 which shows linking caregiver pump 200 to patient pump 100, the caregiver is able to access the control system of patient pump 100, make various inputs using the caregiver's pump 200, and receive back display inputs from patient pump 100 such that the caregiver can see the display inputs on the display 306 of caregiver pump 200. Such communication can occur when the patient pump 100 is located at a remote site from caregiver pump 200. This is particularly advantageous in saving resources by reducing the number of in-person visits between the caregiver and the patient.

In one embodiment, disabling structure is provided with respect to caregiver pump 200 for disabling the pumping mechanism of caregiver pump 200 such that during pump to pump communications, the pumping mechanism and pumping protocol is suspended. Similarly, for patient pump 100, disabling structure is provided to suspend the pumping mechanism and the pumping protocol of patient pump 100 during pump to pump communications. This may be necessary due to processor capability limitations. This may also be a safety feature to prevent a caregiver from starting operation of the patient's pump from the remote site. However, in some situations it may be desirable for caregiver pump 200 to begin operation of the pumping mechanism of patient pump 100 at a site remote from the location of the caregiver during pump to pump communications. If a suitable controller is provided, it may be possible to operate the pumping mechanism of patient pump 100 while patient pump 100 is communicating with caregiver pump 200. Suspension of operation allows the caregiver to see how the pump is configured. The pump is restarted after the pump is disconnected from pump to pump communications set up.

Figure 12A:
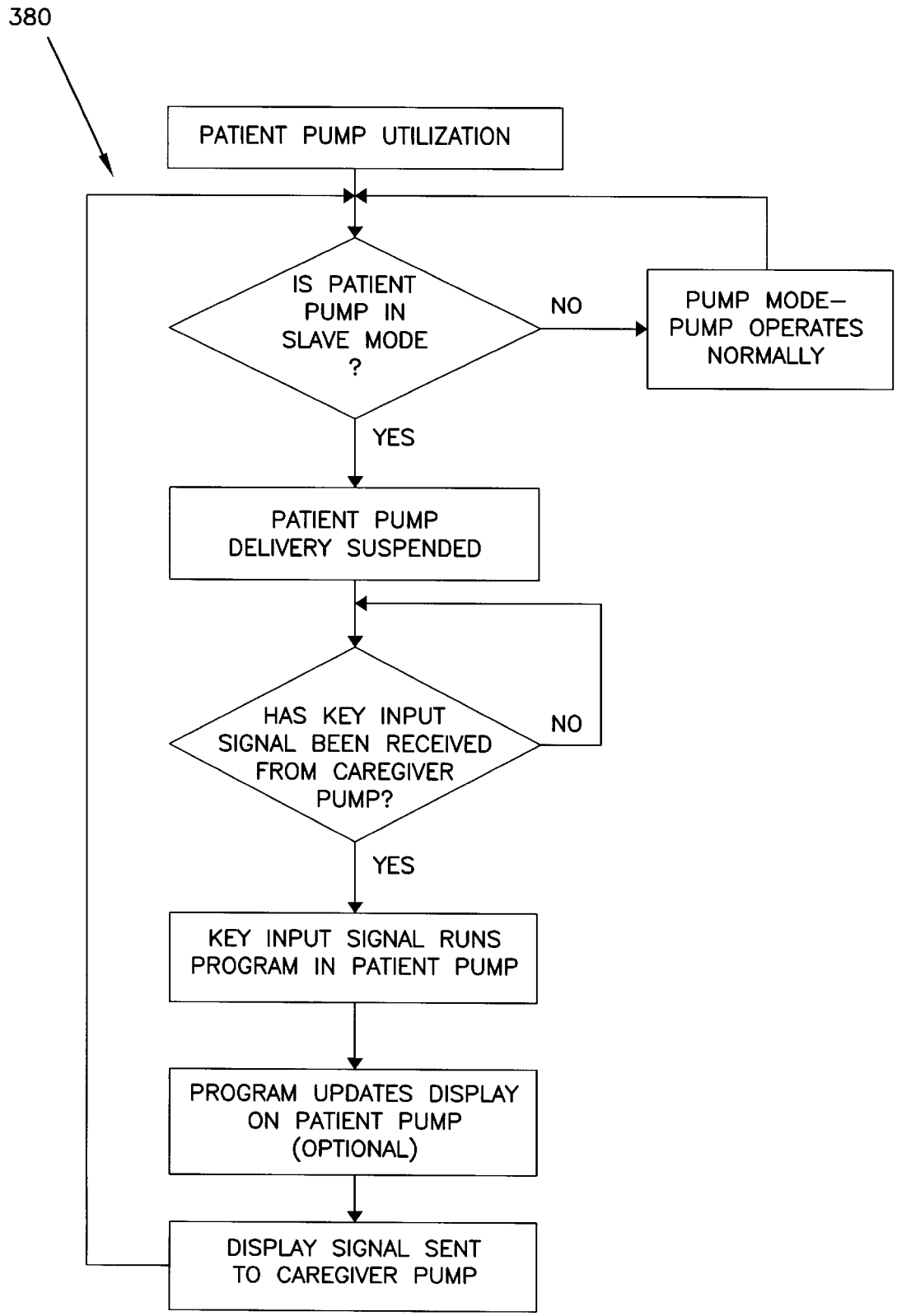
FIG. 12A is a flow chart of an operational sequence of the patient pump with respect to the normal pumping mode for pumping fluid and the slave mode for pump to pump communication.
Figure 12B:
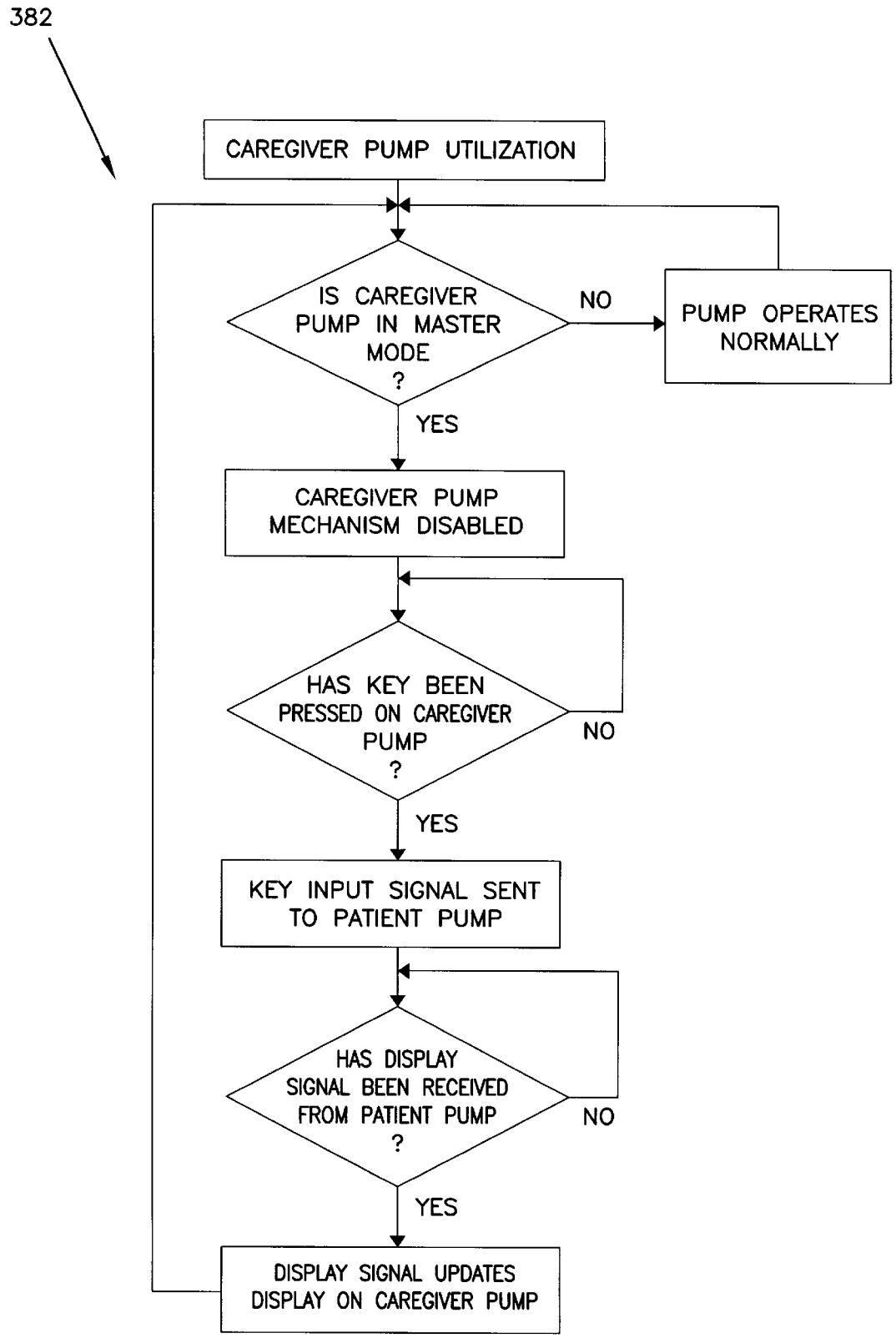
FIG. 12B is a flow chart of an operational sequence of the caregiver pump with respect to the normal pumping mode for pumping fluid and the master mode for pump to pump communication.

Referring now to FIG. 12A, a flow chart 380 is shown illustrating one preferred operational sequence of patient pump 100 with respect to the normal pumping mode and the slave mode. FIG. 12B is a flow chart 382 illustrating one preferred operational sequence of caregiver pump 200 with respect to the normal pumping mode and the master mode. FIGS. 12A and B illustrate the operational sequences for each pump with respect to normal pumping operations mode, or pump to pump communications operations mode (slave and master modes). FIGS. 12A and B specifically show the sequences with respect to communicating the key input signals and the display signals between the pumps. If a caregiver wanted to monitor or program a patient's pump 100 over the phone line 324, the caregiver and the patient would first contact each other, such as by voice communication over the telephone 326, 328, as shown in FIG. 9, to begin initiation of pump to pump communication. Telephones 326, 328 may be conventional telephones including means for dialing another phone, and a handpiece or other device for permitting voice communication with the party on the other end. Prior to initiation of pump to pump communication, both pumps 100, 200 are in the normal pumping mode.

Figure 13:
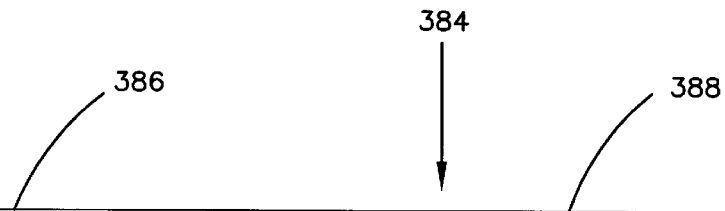
FIG. 13 is a flow chart of two preferred operational sequences for communication between the caregiver pump and the patient pump.

FIG. 13 is a preferred operational sequence shown as flow chart 384 for pump to pump communication. Caregiver pump 200 is operated in the master mode or terminal application in accordance with sequence 386. This program can be resident on memory 184 of pump 200. Once the cable is attached to caregiver pump 200, the pump 200 is ready for pump to pump communication. The caregiver instructs the patient on the upcoming procedures. Both the caregiver telephone and the patient telephone are linked to the local modems 310, 320. Patient pump 100 is operated in accordance with sequence 388. After the cable 322 is connected to patient pump 100, a message is displayed on patient pump 100 "CONNECT TO PHONE." The patient is asked to verify the screen display, wait for a tone, and then hang up. The patient selects the "CONNECT TO PHONE" option, listens for tone and then hangs up. Once the caregiver hears the tone from patient pump 100, the caregiver presses a key 304 on caregiver pump 200. A communication link has been established. The caregiver can review or modify patient pump 100. Patient pump 100 displays a standard message and all key beeps are suppressed. When the caregiver has completed the desired communication with patient pump 100, the caregiver logs off. Patient pump 100 activates an alarm. The display 126 instructs the patient to remove the communications cable 322. The "suspended" status of patient pump 100 is removed, and the pump resumes normal pumping operation. The caregiver can call the patient back, if desired.

The terminal application program shall be written such that it can stand alone in caregiver pump 200 which does not contain any patient pumping application program. The caregiver has the option of running a printing program on the terminal application program which prints the terminal application communications record consisting of the history of at least one pump to pump communication session with patient pump 100. This data can be saved immediately after logging on to patient pump 100. Such data may include: the time and date of log on and the serial number of the pump running the terminal application program; information concerning patient pump 100 including the model number, the serial number, and the identifier of the pump application program running in patient pump 100; information concerning the specific application program running in patient pump 100 including the type of cassette attached to the pump, the status of the latch, the status of the lock, the status of the external power source, the status of the air detector, and the run/stop status of the application program. A terminal application communications record can be generated at the time of logging off including the same type of data noted above. The terminal application communications record can also include the last error code of patient pump 100. Also, the terminal application communications record may include the pump's current time, the pump's current date, the pump's event log, the pump's error history, the pump's hardware I.D., and the pump's 9-volt battery state. In the case of a patient controlled analgesic therapy, additional reports can be generated including any demand dose or clinician lock level.

When the software of caregiver pump 200 detects the communication cable has been connected, the caregiver shall be presented with two connection choices, a communications mode, and a printer mode. The communications mode allows communication with a pump. The printing option allows the caregiver to print an event log including a descriptive name of the report, the name, model and serial number of the pump, the time and date the report was printed, the active application program, a label placed to write the patient's name, the patient's identification number, and the name of the drug being infused.

Automatic selection of the slave mode and stoppage of the normal pumping mode in patient pump 100 is provided using suitable logic circuitry and sensor structure, such as sensor 198 in FIG. 4A, to sense the presence of cable 322. Automatic selection of the slave mode and stoppage of normal pumping mode by inserting cable 322 into patient pump 100 is useful since it eliminates one or more keyboard entries that might otherwise be necessary by the patient or caregiver to place patient pump 100 in the slave mode from the normal pumping mode. Alternatively, the patient may have to hit a predetermined key 124 or flip a suitable switch to exit the normal pumping mode and enter the slave mode if no automatic selection of the slave mode and automatic stoppage of the normal pumping mode is provided.

Sensor 198 may include two spaced apart pins which engage the communication cable 322 to activate sensor 198 when the cable 322 is operatively positioned in communications port 132. Closure of the loop sends a suitable signal to microprocessor 182 that the cable 322 is present and pump to pump communications is desired, i.e. the slave mode operations program.

The operating system of caregiver pump 200 shall allow the pump to be placed in the caregiver mode of remote programming from the normal pumping mode of operation. Automatic selection of the master mode and automatic suspension of the normal pumping mode in caregiver pump 200 is provided using suitable logic circuitry and sensor structure to sense the presence of cable 320, such as with a similar sensor to sensor 198 of patient pump 100. Alternatively, the caregiver may have to hit a predetermined key 304 or flip a suitable switch to exit the normal pumping mode and enter the master mode if no automatic selection linked to insertion of cable 30 is provided.

Patient pump 100 sends its current display to caregiver pump 200 once the pumps are first linked together. In pump to pump communications, the control systems are preferably menu driven and the current display lets the caregiver see the current status of the patient pump 100 before the caregiver begins to send key input signals to patient pump 100 to obtain the desired information from the patient pump. Following the display on display 306 of the current information on display 126, caregiver pump 200 receives its displays sent to caregiver pump 200 in response to the key inputs to caregiver pump 200 which are sent to patient pump 100.

Instead of an automatic initiation of the modem link to patient pump 100 operating in the slave mode, the caregiver and the patient could both hang up their respective phones after the modem cables were connected. Patient pump 100 is programmed to instruct modem 320 installed at the patient's home to answer the phone the next time it rings. The patient would then wait for the caregiver to call back. Caregiver pump 200 is programmed to instruct modem 310 to call the patient back. Once modem 310 is connected with modem 320, communication between the respective controllers is provided with respect to key input signals and display signals.

In one embodiment, display 126 of patient pump 100 displays everything that is sent to display 306 of caregiver pump 200. In another embodiment, the control system of patient pump 100 is programmed to include a blocking program to block some or all of the information that is sent to the control system of caregiver pump 200 from the controller of patient pump 100 from being displayed on display 126 of patient pump 100 during pump to pump communication. This may be advantageous in keeping some information from the patient, such as controller access codes used to access the processor of patient pump 100 via the keys 124, or keys 304 during pump to pump communications.

If the communication session were interrupted by a bad phone line, patient pump 100 might remain unchanged or partially programmed. During programming of patient pump 100, caregiver pump 200 could get a continuously updated status report from patient pump 100 through appropriate programming in caregiver pump 200 and patient pump 100. The caregiver could review the status report after disconnecting the pump from the modem to verify that patient pump 100 had been programmed as desired by the caregiver.

The control system of each pump 100, 200 controls operation of the respective modem 310, 320 attached as a peripheral device. The control system of each pump 100, 200 instructs its respective modem to go off-hook and disconnect the phone at the initiation of pump to pump communications.

The control system of each pump 100, 200 may be provided with masking programs to mask the keys 124, 304 which are inactive during pump to pump communication.

Attempting to start the caregiver pump 200 is one method of signalling to the control system to terminate the pump to pump communication. The control system of caregiver pump 200 begins the disconnection sequence with respect to modem 310. The control system of caregiver pump 200 further requests that patient pump 100 begin the disconnection sequence with respect to modem 320. Alternatively, pressing another key such as a HELP key can begin a disconnection sequence.

In some applications, the control system of patient pump 100 is locked, at least partially, via an access code program to prevent the patient from altering the pump operations program or from accessing other information in the memory. In one preferred embodiment, the caregiver can unlock the pump lock of patient pump 100 from a remote location via the pump to pump communication system. Preferably, the caregiver can then relock the pump lock of patient pump 100 after the caregiver has adjusted or changed the pump operations program. Automatic relock program means may be provided to automatically relock the control system at the conclusion of the caregiver's access of the control system to change the operating programs.

In one possible embodiment, locking the pump 100 is accomplished through various lock levels that are used to limit patient access to certain programming and operating functions. Each lock level provides a different level at which the user can interact with the pump 100. Each programming and operating function is executed by predetermined key strokes. If a function is not available at the lock level that is set, the microprocessor will ignore the predetermined key strokes if pressed.

One embodiment of the pump 100 has three lock levels - - - LL0, LL1, and LL2. When the pump 100 is in LL0, the user can access all programming and operating functions of the pump 100. LL1 permits limited control of the programming and operating functions. LL2 permits only minimal access of programming and operating functions. When the pump 100 is running, it is usually in a predetermined lock level that offers some security against an unauthorized person from reprogramming the pump 100, either LL1 or LL2.

Figure 14:
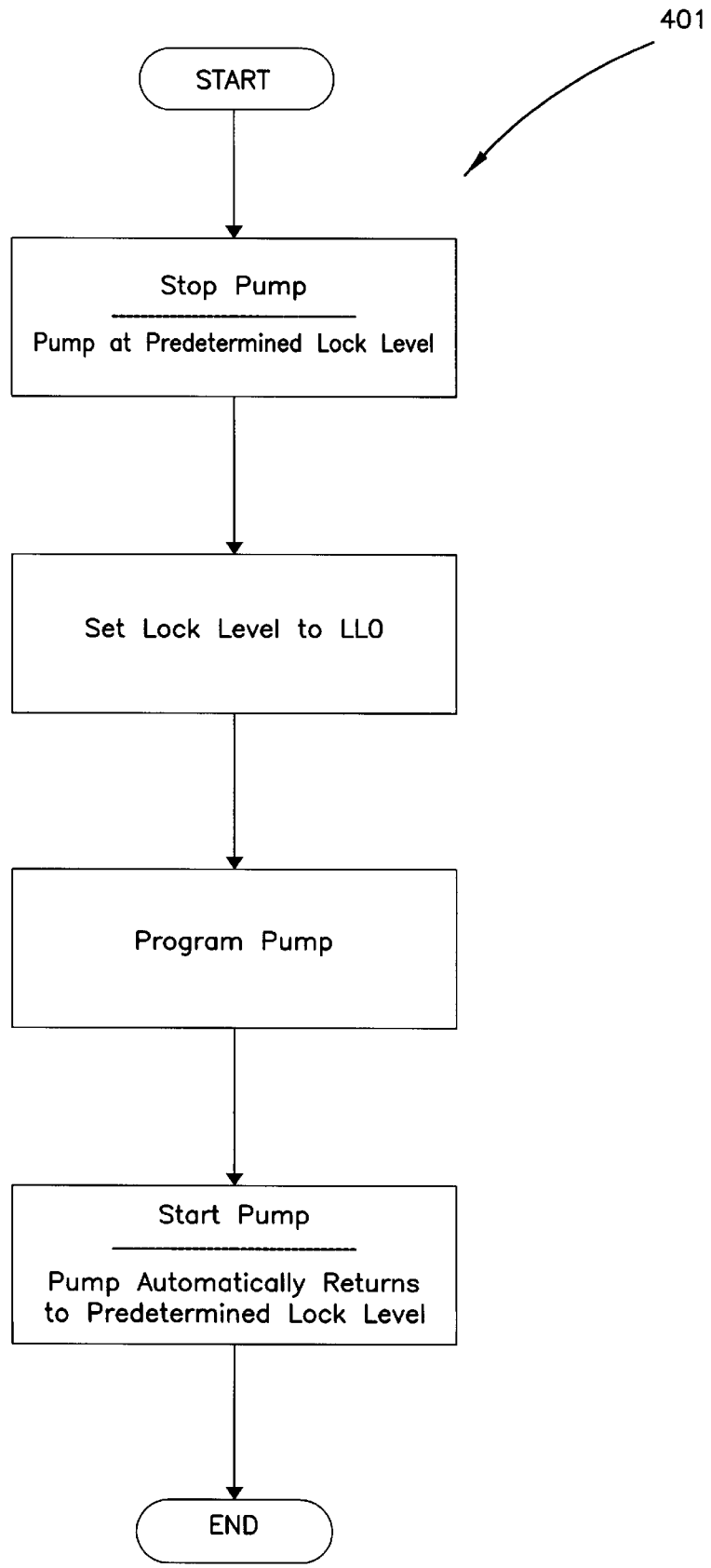
FIG. 14 is a flow chart showing operation of an automatic lock level feature.

FIG. 14 is a flow chart 401 that shows the operation of the autolock feature of the pump 100. When programming the pump 100, the user must stop the pump 100 from operating. At this point, the pump 100 is typically in the predetermined lock level, usually LL1 or LL2. The user must then change the lock level to LL0 in order to gain access to programming functions. When changing the lock level to LL0, the user must execute a predetermined sequence of key strokes including entering a password and indexing the lock level until it reaches LL0.

The user can then reprogram the pump 100. Programming in this sense is not changing the actual programming code loaded in the pump 100, but is rather launching a new application program from the flash memory or changing operating parameters such as dosages and delivery rates. After programming is complete, the user can press the START/STOP key, one of the keys of the pump 100, which will restart the pump 100. When the START/STOP key is pressed, the pump 100 will automatically return to the predetermined lock level.

In the past, the user had to manually reset the lock level to its predetermined level. Otherwise, the lock level would stay at LL0 when the pump 100 was restarted and given to the patient. In this situation, an unauthorized person could access programming and operating functions in the pump 100 and change parameters such as delivery dosage and delivery rates. Thus, the present invention is advantageous because it eliminates this risk by automatically returning the pump 100 to the predetermined lock level when it is restarted.

In an alternative embodiment of the present invention, the pump 100 will not automatically enter the predetermined lock level if the caregiver manually sets the lock level prior to pressing the start button to restart the pump 100. Rather, the pump 100 will remain at the manually set lock level. This feature is advantageous because it allows flexibility in resetting the lock level after the pump 100 is reprogrammed.

Another alternative embodiment of the present invention permits the caregiver to turn the automatic lock level feature on and off.

Figure 10:
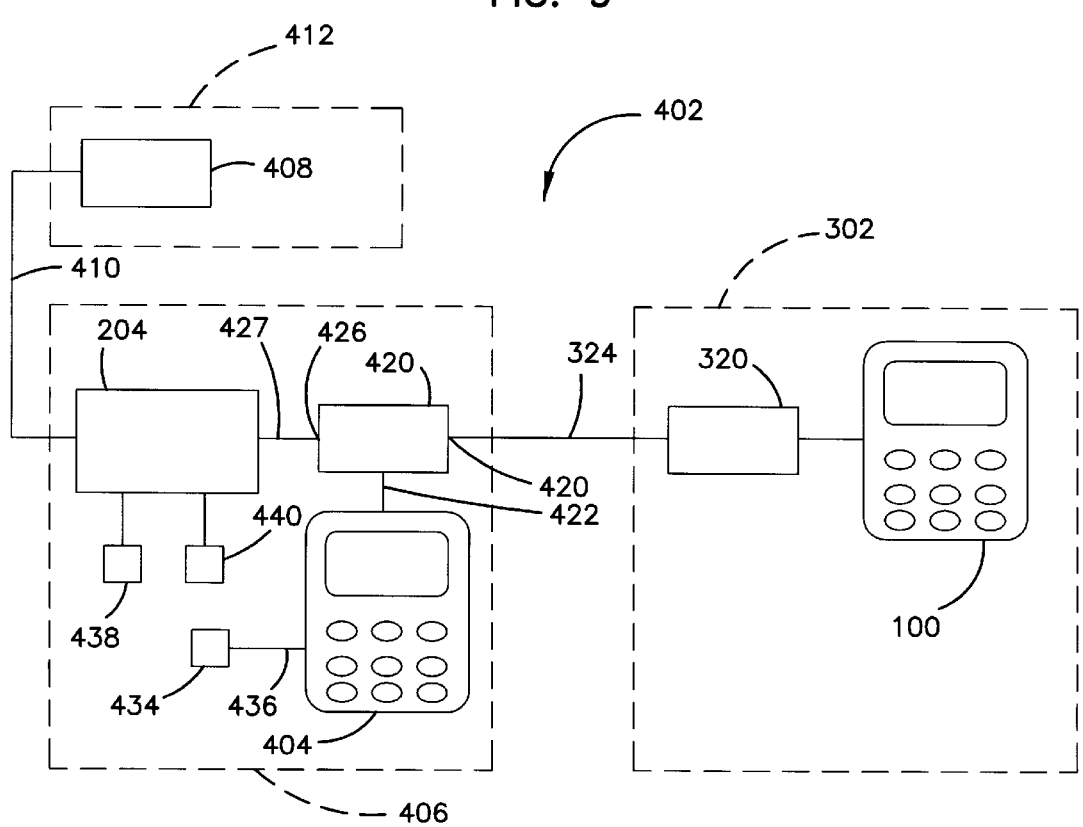
FIG. 10 is a schematic drawing illustrating a second system using a personal computer to communicate with a local pump and/or a remote pump. Local pump and remote pump communications capability is also shown.

Referring now to FIG. 10 specifically and FIG. 6 generally where an alternative embodiment is shown, the schematic diagram of FIG. 10 illustrates a communication system 402 for communication between pump 404 and computer 204, both located at caregiver's office 406. Pump 404 may be a caregiver pump, like caregiver pump 200, or a patient pump, like patient pump 100.

FIG. 10 also illustrates communication between a patient pump 100, located at the patient's home 302, and both computer 204 and pump 404. It is to be appreciated that in some applications, pump 404 may not be present. Also, it is to be appreciated that in some applications pump 100 may not be present. In either of those applications, computer 204 would be communicating only with the remaining pump.

An example of computer 204 includes an 80386 INTEL microprocessor, with 2 megabytes of RAM and operated by commercially available operations software such as DOS, UNIX, and others and further programmed with application specific program functions to communicate with pumps 100, 404 and carry out the specified tasks desired by the caregiver. A suitable keyboard may be provided with computer 204 to make operator inputs to the microprocessor.

As shown in FIG. 10, computer 204 may further communicate with a second computer 408 to transfer data and or programs to and from computer 204 over communications medium 410, such as conventional telephone lines. For example, computer 204 may be located at the caregiver's office 406, such as a hospital. The second computer 408 may be located at the pump manufacturer's/servicer's facilities 412. The second computer may receive and transmit information to a plurality of computers 204. This arrangement may be useful for maintaining a plurality of patient pumps 100, through a plurality of caregiver's offices 406. Also, improved drug therapies may result if the pump manufacturer/servicer has ready access to patient pump usage data.

Pump 404 is preferably identical mechanically and electrically to pumps 100, 200 described previously. In some situations, the control system of pump 404 may be programmed differently, depending on how the pump is to be used. Pump 100 is typically used as a patient pump. As a patient pump, pump 100 requires the normal pumping mode operating program and the slave mode operating program at minimum.

In system 402, pump 404 may be a patient pump or a caregiver pump. As a patient pump, pump 404 requires the normal pumping mode operating program and the slave mode operating program at a minimum. Pump 404 as a patient pump is present at the same site as computer 204 such as when pump 404 is brought in by the patient. In some situations, pump 404 may be a patient pump that is in the caregiver's office 406 for data gathering, trouble shooting, and/or program changes or modifications. Also, before the patient leaves the caregiver's office 406, pump 404 is present in caregiver's office 406 for use as a patient pump in the caregiver's office. As a caregiver pump, pump 404 requires the master mode operating program at a minimum. Pump 404 operating as a caregiver pump may also include the normal pumping mode operating program and the slave mode operating program.

To permit communication between pump 404, computer 204, and pump 100, a modem 420 is provided. Preferably modem 420 is a conventional modem for remote communication over telephone lines.

Figure 11:
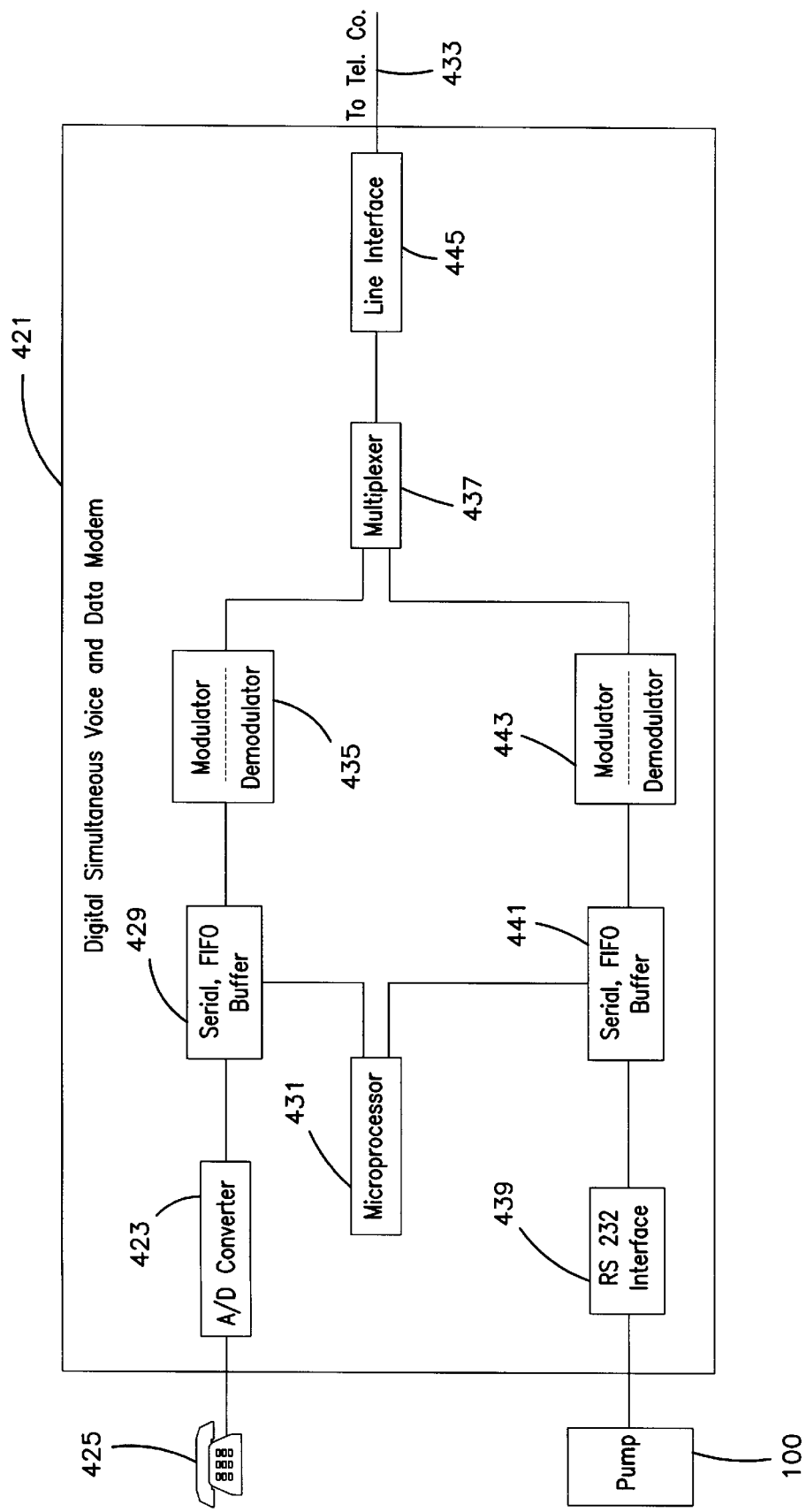
FIG. 11 is a schematic drawing of a preferred modum useful in the communication systems shown in FIGS. 9 and 10 to allow simultaneous voice and data transmission during pump-to-pump communication.

In another preferred embodiment, modems 310, 320, and 420 can be replaced with a digital simultaneous voice and data modem 421 that has the capability of simultaneously transmitting voice information between the patient and caregiver, and data information between the master pump and the slave pump. As shown in FIG. 11, such a modem 421 includes circuitry, i.e. an A/D converter 423, for digitizing the signal containing the voice information. The voice information is received from a telephone 425. The digitized voice signal is then placed in a serial FIFO buffer 429 at which point a microprocessor 431 will process the data to prepare it for transmission over the telephone line 433. Such processing is well known in the art and may include adding information for an error detection scheme such as checksum. In another embodiment, the microprocessor 431 might add information for packet identification. The digital signal is then passed through a modulator 435 and communicated to a multiplexer 437.

Data from the pump 100 is simultaneously communicated through an RS232 interface 439 and then to a second serial FIFO buffer 441 at which point the microprocessor 431 will process the data for communication. The information is then passed through a second modulator 443 and communicated to the multiplexer 437. The multiplexer 437 then transmits packets of information from the pump 100 and the telephone 425 to a line interface 445, which communicates it over the telephone line.

One skilled in the art will realize that the digital simultaneous voice and data modem 421 at the receiving end will essentially operate in the opposite manner. One skilled in the art will further realize that FIG. 11 merely illustrates one possible embodiment of the digital simultaneous voice and data modem. Other embodiments of the digital simultaneous voice and data modem 421 are possible. One type of digital simultaneous voice and data modem that can be used in the present invention is the Sportster Vi 28.8 fax modem with digital simultaneous voice and data. This modem is manufactured by U.S. Robotics of Skokie, Ill.

One advantage of using a digital simultaneous voice data modem 421 during pump to pump communications is that oral communication between the patient and caregiver is not interrupted. As a result, the caregiver can answer questions and give instructions during pump to pump communications.

FIG. 10 also shows pump 404 interconnected to its own stand alone printer 434 interconnected with connection structure 436, such as an RS232 serial cable. Parallel communication may be used, instead of serial communication. Printer 434 produces a hard copy of information stored in the control system of pump 404. In some cases, printer 434 would be useable only through the communications port which connects pump 404 to modem 420, as shown in FIG. 10. In other words, pump 404 may not be useable simultaneously with printer 434 and modem 420. An appropriately sized control system and two communications ports would permit such usage.

Communication between computer 204 and a pump, whether remotely (with pump 100) or locally (with pump 404) is useful for several reasons. First, computer 204 may be provided with greater memory and data processing capabilities than exist with the individual pumps 100, 404. Printing capabilities may be greater with a printer 438 electrically interconnected to computer 204. Display capabilities may be greater with a monitor 440 electrically interconnected to computer 204. Also, computer 204 may be useful in the recertifying operations of the pumps periodically, as required to verify operability and accuracy of the pumps.

Computer 204 also may be useful for making program adjustments or application changes in the pumps 100, 404, such as described in application Ser. No. 08/561,809, previously incorporated by reference. For example, drug delivery devices may be used in a variety of normal pumping modes, or applications, such as 1) pain control; 2) nutrition; 3) chemotherapy; and 4) antibiotic therapy. Other applications are possible.

Each of the applications may involve different operations of the pumping mechanism. Each application may have one or more patient specific variations on operation of the pumping mechanism and other pump control functions. Also, some of the applications may involve some patient input, such as is sometimes the case in pain control applications. For example, if the patient is experiencing pain at a particular time, the caregiver may provide for increased dosages as needed by the patient, within specified parameters such as time and amount. In this application, the pumping mechanism needs to be operable automatically, and at the discretion of the patient, within the specified parameters. The operating program contains the appropriate pump control commands for controlling the pumping mechanism and the functions of the keys which permit patient control of the pumping mechanism. The other applications may include different pump control commands and different functions of the keys. Within each of the four applications listed above, various different pump operations programs may exist. The control system of the patient pump 100 may be appropriately programmed by the caregiver for the specific patient usage.

It is to be appreciated that the caregiver pump 200 and the patient pump 100 do not need to include the same application program for operating the pumping mechanism. A significant advantage of the present invention is that the caregiver can communicate successively with different patients, with each patient involving a different pump application, or each patient involving the same pump application with different patient specific functions. At a minimum, it is preferred that caregiver pump 200 includes the master mode operations program, and that patient pump 100 includes the slave mode operations program and one application or normal pumping mode operations program for operating the pumping mechanism to pump fluid to the patient. Preferably, it is more convenient for the caregiver if caregiver pump 200 and patient pump 100 include both the slave mode operations program and the master mode operations program, and also at least one normal pumping mode operations program.

It is anticipated that the caregiver can locally or remotely program the control systems of pumps 100, 200, 404 such that the pump operates either in 1) the normal pumping mode or slave mode, or 2) the normal pumping mode or the master mode at the initiation of the pump to pump communications sequences.

Various pump related data may be stored in the control systems of pumps 100, 200. Information which may be gathered during use of patient pump 100 includes date and time of:

1) Pump Error Conditions, for example, where the pumping mechanism has stopped and a suitable sensor sends a pump stoppage signal to the processor.

2) High Pressure Alarm for Downstream Blockages, where a suitable pressure sensor sends a high pressure signal to the processor.

3) Upstream Occlusion Alarm, where a suitable pressure sensor sends an occlusion signal to the processor.

4) Any Fluid Reservoir Removal Event, where a suitable sensor sends a reservoir removed signal to the processor.

5) Any Fluid Reservoir Attached Event, where a suitable signal is sent to the processor by a suitable sensor, possibly the same sensor as the sensor for sensing a reservoir removed event.

6) Any Internal Battery Event, where a suitable sensor senses whether the battery has been changed, is low, or is depleted.

7) Any AC Adaptor Event, where a suitable sensor senses whether the adapter is connected, disconnected, or unplugged from the wall outlet.

8) Any portable Power Pack Event, where a suitable sensor senses whether the power pack is connected, disconnected, or depleted.

9) Any Remote Dose Cord Event (which permits patient to remotely press a key, such as the DOSE key on the keypad), where a suitable sensor senses whether the dose cord is connected or disconnected.

10) Any Communications Cable Event (to permit the pump to communicate with a printer, another pump or a computer), where a suitable sensor senses whether the cable is connected or disconnected.

11) Anytime the Device is Successfully Stopped or Started with START/STOP key, where a suitable sensor senses whether the pump is successfully stopped or started after the key is pressed.

12) Any Lock Level Change and the New Lock Level, in situations where the amount of access to the processor by the patient is changed, i.e. full access, some access, no access.

13) Any Patient Pump Operational Program Change or Status Reset/Clear in the New Program.

14) Anytime the PRIME key is used and how much fluid is primed to get air out of the tubing, such as during pump start up.

15) Any Patient Dose Delivered and the Amount Delivered by the patient hitting the DOSE key to manually give the patient an additional amount of fluid.

16) Any Change in Other Features (units, time or date set, auto lock change, application change) and the New Data or State.

17) Anytime the Pump is Successfully Recertified.

18) Number of Activations of Pumping Mechanism and Duration of Use.

19) The status of the various other sensors of pump 100 including latch sensor 188, lock sensor 190, AC adaptor sensor 228, and an air detector sensor for detecting when an air detector is attached.

Various functions are anticipated for each of the keys on each pump 100, 200. Each key has at least one function. Examples of potential functions of the different keys include:

1) A NEXT SCREEN key to move through the various screens by running a next screen program;
2) An ENTER/CLEAR key;
3) AN UP ARROW key and a DOWN ARROW key for paging through what is displayed on the screen with a highlight bar, responding to YES/NO questions, or to page through numeric values to highlight and/or display the desired value;
4) A PRIME key to run a pump prime program to prime the pump;
5) A START/STOP key for operating a pump start program and a pump stop program;
6) A LOCK key for providing access control to the processor through an access program;
7) A DOSE key to run a patient pump control program for permitting patient control of the pumping mechanism;
8) A HELP key for providing help information on the display.

PUMP SIMULATION SYSTEMS AND METHODS

Figure 15:
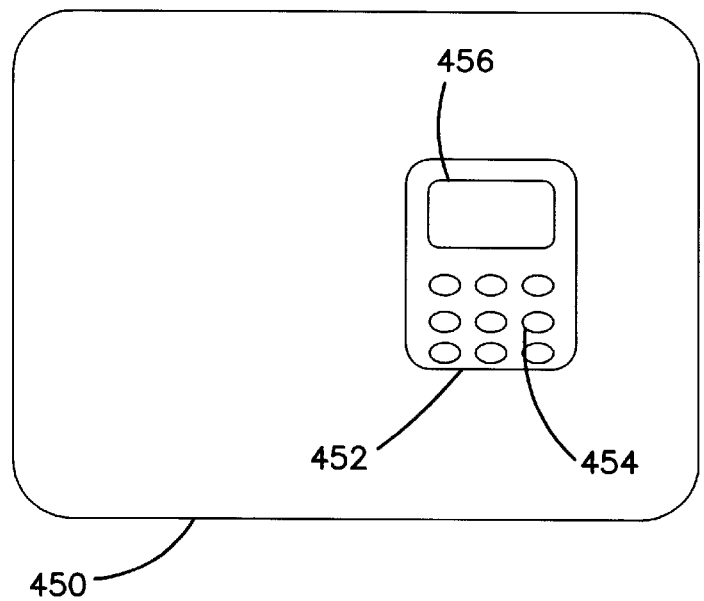
FIG. 15 is a schematic drawing showing a computer screen displaying an image of a pump, as part of a computer system used for communicating with a pump.

Referring now to FIG. 15, a monitor or computer screen 450 is shown, as another embodiment of the invention. An image of pump 100 (front view) is displayed on screen 450 through suitable graphics capability. Screen 450 is operatively interconnected with a processor of computer system, such as the processor of computer 204. The image 452 on screen 450 is able to be manipulated as if it were a pump through the use of a screen interactive program utilizing a mouse or a touch screen. Computer 204 is programmed to run various programs depending on how the various keys 454 of pump image 452 are pressed through the use of the mouse or the touch screen. This permits simulation of the pump 100 with the use of a computer 204. Display area 456 may then display information like display 126 of pump 100.

Computer screen 450 and computer 204 are utilized to communicate with a pump located at a remote site, like pump 100 of FIG. 10. If the pump is located locally, like pump 404 of FIG. 10, then communication is direct with a straight through pass as shown in FIGS. 10 and 11.

The arrangement involving the computer screen of FIG. 15 is useful when the caregiver is communicating with a patient pump at a remote location or at a local location. The caregiver can more easily use the computer system since the caregiver is already familiar with the operation of a pump through the use of the keys and the display. Activating the keys 454 of the image 452 and using the display 456 of the pump image simulates for the caregiver the presence of an actual pump. This facilitates reductions in training time for training the caregiver to communicate with the patient's pump, since the caregiver is most likely already familiar with operation of the patient's pump.

The computer system with the pump image program may also be used as a simulator for training the caregiver and/or the patient how to use the pump. The simulator includes various programs for simulating operation of a patient's pump to pump fluid. The simulator also includes various programs for simulating various communication situations with a patient's pump.

Figure 16:
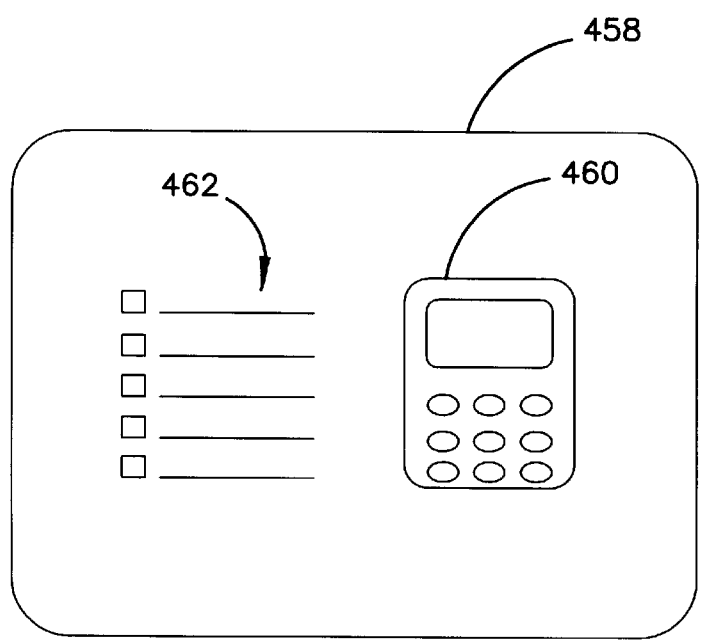
FIG. 16 is a schematic drawing showing a second computer screen displaying an image of a pump, as part of a computer system, and including information displayed on the screen relating to simulation sequences for use in training.

As shown in FIG. 16, a computer screen 458 of a training simulator system is shown. On computer screen 458, pump image 460 and simulator information 462 are displayed. Simulator information is used to select various conditions through simulator programs for simulating a operation of a patient pump. Pump image 460 could function as a caregiver pump to permit training of a caregiver on how to use the caregiver pump to communicate with a patient pump. For example, if the caregiver trainee wanted to simulate a communications session with a remote patient pump that had a low battery, for example, the caregiver trainee would select the program in simulator information 462 that would simulate a pump to pump communications situation where the caregiver would trouble shoot the patient pump to determine that a low battery situation existed. The simulator also has a simulator program for simulating at least some of the sequences to connect and disconnect the pumps according to the flow chart of FIG. 14.

The simulator system also includes simulation programs in simulator information 462 for simulating operation of the pump on the screen 458 as a patient pump to pump fluid to a patient. This would be useful for training a patient and a caregiver how to operate the pump in the normal pumping mode.

The present invention relates specifically to a pump communication simulator for training a pump operator comprising: a computer system including processor means, and display means electrically interconnected to the processor means of the computer system; first program means for displaying an image of the pump on the display means, the image having an input region and a display region; second program means for permitting manipulation of the input region of the image of the pump on the display means by the pump operator such that access to the processor means of the computer system is achieved; and third program means for sending a predetermined message to the display region of the image of the pump in response to manipulations of the input region of the image by the pump operator.

FLASH MEMORY SYSTEMS AND METHODS

Flash memory 240 is electrically interconnected to the processor 182 for storing pump operation information (See FIGS. 8A and 8B). The flash memory 240 is electrically interconnected to the communications port 132 to permit transfer of pump operation information to the flash memory 240 from external of the pump.

Figure 17:
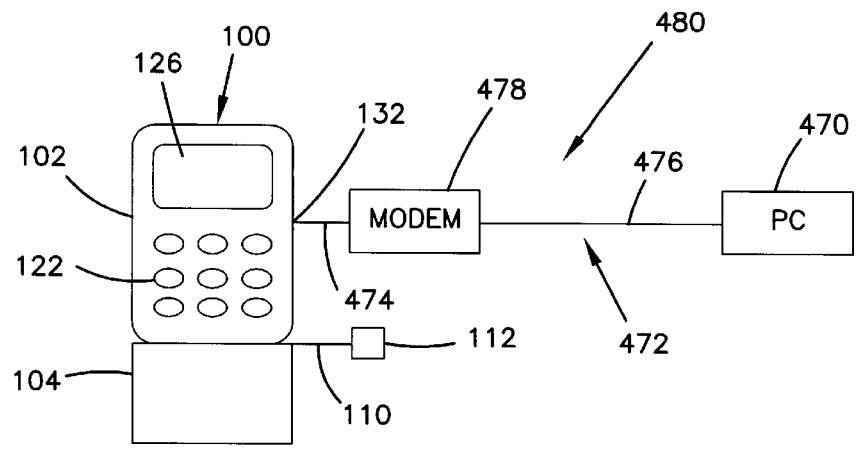
FIG. 17 is a schematic drawing of the drug pump of FIG. 1 shown linked to a personal computer for communication with the personal computer for programming of the flash memory of the pump.

Referring now to FIG. 17, communications port 132 permits the downloading of pump operation information from a computer system 470, such as a personal computer. The computer system 470 typically includes a processor, memory, an operator input means such as a keyboard for inputting data, a data input means such as disk, tape, or card reader, and a display means such as a monitor for displaying appropriate information to the operator of computer system 470. Computer system 470 can also be utilized to view the pump operation information including any patient specific settings previously input to the memory in pump 100 to speed the reprogramming of pump 100.

Communication means 472 links computer system 470 and pump 100. Included in communication means 472 is a cable 474 or other communication structure interconnecting communications port 132 of pump 100 to a device 478. Cable 476 or other communications structure interconnects device 478 to computer system 470. Pump 100 is preferably not linked directly to computer system 470, since pump 100 may be provided with one or more power supplies other than conventional 110 volt power supplies used to power computer system 470. Device 478 performs an isolation function in FIG. 17. It is desirable to electrically protect pump 100 from computer system 470 to protect pump 100 and the patient from any hazards, such as electrical shock, associated with the electrical source power for computer system 470. In FIG. 17, device 478 may communicate with computer system 470 through an RS232 serial cable. Similarly, device 478 may communicate with pump 100 through an RS232 serial cable. Device 478 is to be appreciated as an optional device if it is not desired to electrically isolate pump 100 from computer system 470. In that case, an RS232 serial cable can connect pump 100 and computer system 470 directly. Alternatively, communication with pump 100 via communications port 132 can be by non-mechanical connections, such as by infrared signals transmitted to pump 100 and receivable by an appropriately configured infrared signal receiver associated with communications port 132. Device 478 is also configured as a modem for use in transmitting data to and receiving data from a remote location, in addition to the structure for local communication with computer system 470 in an isolation function, as shown in FIG. 17.

The operations system 480 of FIG. 17 is useful for downloading pump operation information from computer system 470 to pump 100. The information can be downloaded to one or more memory locations in pump 100 for storage. Once the information downloading operation is complete, pump 100 can be disconnected from device 478 and cable 474. This permits pump 100 to be conveniently carried about by the patient wherever the patient desires, such as around the home or around the patient's work place. Pump 100 is preferred to have a disabling function for disabling the fluid delivery system until device 478 and cable 474 are disconnected from pump 100. However, such operation of the pump is preferred but not mandatory.

Figure 18:
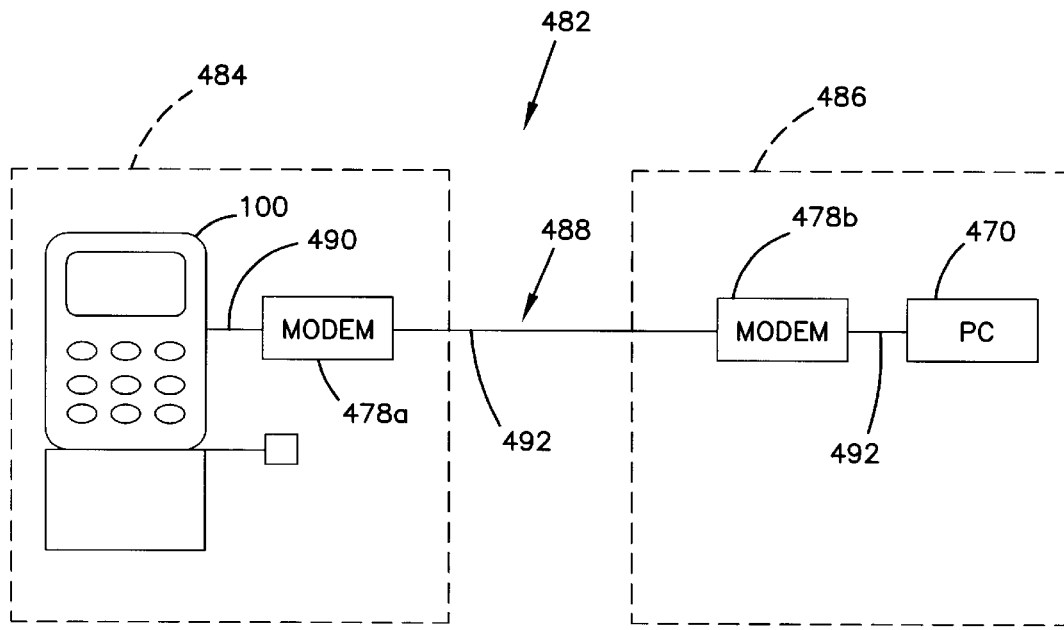
FIG. 18 is a schematic drawing illustrating the pump of FIG. 17 linked to a personal computer located at a remote site.

Referring now to FIG. 18, a second system 482 for operation of pump 100 is shown. In FIG. 18, pump 100 is located at a first site 484. Computer system 470 in FIG. 18 is located at a second site 486 which is remote from site 484. Remote communication means 488 permits communication between the pump 100 and computer system 470. Remote communication means 488 includes a first cable 490 or other communication structure linking pump 100 with a first modem 478a. A second cable 492 or other communications structure links computer system 470 to a second modem 478b. First cable 490 and second cable 492 may be RS232 serial communication cables. First and second modems 478a,478b may be identical to device 478. However, modems 478a,478b are not operated in the pass through configuration as is device 478 in system 480 of FIG. 19. First and second modems 478a,478b permit communication between remote sites over a communications medium 492 such as conventional telephone lines, cellular phone systems, fiber optics links, satellite links, microwave links, or other remote links. First and second modems 478a,478b may communicate at 9600 bps over conventional phone lines and include error correction and data compression features.

The second operations system 482 in FIG. 18 is useful to download pump operation information to pump 100 located at site 484 from a remote site 486. Remote downloading of pump operation information is useful since pump 100 does not have to be handled by the party who is downloading the pump operation information to pump 100 from the remote site. Site 484 may be the patient's home or work place and site 486 may be the caregiver's office or home. Alternatively, site 484 may be the caregiver's office, and site 486 may be the pump maintenance site or the pump manufacturing site.

Device 478 of FIG. 18 permits information to be transmitted to and from computer system 470 located either locally with pump 100 or remotely to pump 100. If one mode of communications is not desired, then it is not necessary for device 478 to include apparatus for permitting both local and remote communications capability. For example, modems 478a,478b may not need local communications capability in the pass through configuration if the modems will not be used to link a local computer system with a local pump. Also, for the system of FIG. 17, if the only communication anticipated with pump 100 is local, then device 478 need only be constructed with the local communications apparatus to permit the pass through communications with electrical protection of the pump. Finally, if electrical protection is not needed, then only an electrical connection between pump 100 and computer system 470 needs to be provided in general and a direct cable download can be utilized.

Flash memory 240 is utilized to store pump operation information which is accessed by the processor 182 for operating pumping mechanism 140 and the other sensors, switches, and devices of pump 100. Flash memory 240 permits pump operation information to be initially electrically written to flash memory 240 and subsequently stored in flash memory 240. Storage of the pump operation information in flash memory 240 is nonvolatile in that is does not require a continuous power supply to flash memory 150 to maintain the information stored in the memory. At a later time, flash memory 240 can be electrically erased, and rewritten with different pump operation information.

In one preferred embodiment, the program or programs needed to run pump 100 is stored in the flash memory 240. Patient specific settings for pump 100 can be input via keyboard 122 or communications port 132 and stored in flash memory 240, memory associated with microprocessor 182 or EEPROM 242. Examples of patient specific settings include rate of infusion, length of infusion, bolus information, security codes, and patient weight and sex. It is preferred to store such patient specific pump operation information in EEPROM 242 or other memory location other than flash memory 240 due to limitations of flash memory 240 with respect to the number of times the memory can be erased and rewritten. Since the patient specific information is typically frequently changed in many of the anticipated uses of pump 100, it is not desirable to store this type of information in flash memory 240. Port sensor 198 can be used to appropriately direct incoming data to the proper location by sensing when a cable is present. If not present, pump 100 will look to its internal memory 184 for the information needed to run the pump and keyboard 122 for patient settings if not already entered.

Static RAM 244 can be utilized to store some information relating to operation of the pump. Typically, intermediate information concerning pump operations is stored in the static RAM 244. Intermediate information may include calculation results from the pump operations program performed by microprocessor 182. Pump usage information regarding pump operation events may be stored in static RAM 244, such as the number of start and stop events, the number of cassettes attached, and the total dosage pumped. An additional location for storage of pump operation information is the memory associated with the real time clock 246.

Flash memory 240 preferably includes a boot program which is preferably non-erasable. The boot program permits initialization and loading of pump operation information to the pump 100 via communications port 132. Further, gate array 257 and/or flash memory 240 includes appropriate programming to handle incoming data from communications port 132 or keyboard 122 wherein the information is directed to the proper storage location if the information is not to be stored in flash memory 240. For example, remote programming may be utilized to enter the patient specific information into control system 180. The patient specific information may be entered initially or when changes occur over time due to changes in the specific therapy needed. For example, if the patients condition improves or worsens, changes may need to be made in the specific patient settings. The flash memory 240 may include the appropriate program or programs to direct storage of the patient specific settings to the appropriate memory device in control system 180.

Flash memory 240 is an embedded memory associated with control module 102. Once installed in control module 102, flash memory 240 is not removed from pump 100. Flash memory 240 is electrically erasable and reprogrammable and does not require power to maintain the contents of its memory. A variety of flash memories may be used for flash memory 240. An example of one preferred flash memory which is usable in pump 100 is by Intel Corporation, and identified as 28F008SA 8MBIT (1MBIT× 8) Flashfile™ memory. Such memory is useful in pump 100 for handling pump operations information associated with the various features provided on pump 100. The Intel product is useful in that it includes separately erasable and reprogrammable blocks of memory, at least one of which can be blocked from erasure once programmed with the desired information.

Pump 100 may be utilized for a variety of different therapy types or applications. For example, pump 100 may be used as a pump in: 1) a pain control therapy, or patient controlled analgesia; 2) a nutrition therapy, or total parenteral nutrition therapy; 3) a chemotherapy program or therapy; or 4) an antibiotic therapy. Other applications are possible. All of these can be resident on pump 100, or they can be uploaded to pump 100 on an as needed basis. The different applications may involve different operations of pump mechanism 140 and the other switches, sensors, and other devices in pump 100. For example, the volume of fluid per unit time pumped by the pumping mechanism 140 may be continuous or it may be changed over time. A bolus amount (increased dosage) pumped by the pumping mechanism 140 may be provided once or at periodic intervals. The bolus amounts and/or the bolus intervals may be varied over time. The patient may be given limited ability to increase the dosage when the patient desires by causing extra activations of the pumping mechanism 140 through a dose key.

As another example, there may be lock out access to the patient wherein various keys of keyboard 122 are inoperative such that the patient cannot change the therapy prescribed by the caregiver unless the caregiver removes the lock out feature. Each application may have different lock out features.

Calculations by the processor may be needed to achieve a certain total dosage over a certain time even though the patient may be able to increase the dosages at one or more times during the therapy. Inputs to pump 100 may include reservoir size, activation amount, and/or drug concentration. In some cases, it is desirable for pump 100 to calculate the desired number of activations and intervals to achieve a certain drug level in a patient having a certain sex and weight. Each application may involve different calculations performed by pump 100.

Other sensors, switches, and devices of pump 100 may be operated differently in different therapies. The pump control program stored in the memory of pump 100 including flash memory 240 includes information relating to the various aspects of pump 100 needed to deliver the appropriate therapy. In one preferred pump 100, flash memory 240 contains the general application or operating program (such as pain, nutrition, antibiotic, or chemotherapy) which is accessed by processor 182 during usage of pump 100. Only one application be stored in flash memory 240 as a safety precaution against the caregiver or the patient inadvertently running the wrong program. Alternatively, a plurality of different applications can be stored in flash memory 240 to allow selection of the desired application for the patient's needed therapy. Also, the other pump function programs can be stored in flash memory 240, such as the programs necessary for pump to pump communication or other administrative functions. Also, variations in the display language can be stored in flash memory 240 so as to display messages in a desired foreign language.

The patient specific information needed to operate pump 100 for the specific application is stored in the memory associated with microprocessor 182 and is utilized by the processor 182 when needed with respect to the pump applications program. Any intermediate calculation information or other pump information, including specific pump usage information, may be stored in any of the various memories. Static RAM 244 provides a useful memory location for storage of the intermediate information.

Pump 100 can be programmed from computer system 470 in a variety of different ways. In one method, computer system 204 can include a single pump application program stored in its memory. The caregiver or pump supplier would load the pump application program from computer system 204 to flash memory 240 of pump 100. Alternatively, computer system 204 can include a plurality of different pump application programs. The caregiver or pump supplier can select the desired program to be loaded to flash memory 240 of pump 100. Alternatively, computer system 204 can include one or more pump application programs that each include options for selection by the caregiver or pump supplier for each pump application program. Once the options are selected, the caregiver can load the pump application program generated by the caregiver to flash memory 240 of pump 100. In the above methods, it is anticipated that the caregiver would not generate the code for the pump application program. The code would be supplied by the pump supplier or other programming specialist. This is a safety feature as well as convenience to the caregiver.. The caregiver need only be familiar enough with computer system 204 to set up the link to pump 100 and then select and download the appropriate pump application program. It is to be appreciated that, in some cases, the caregiver will have sufficient expertise to generate the code for the pump application program. Similar safety and convenience features are present with respect to any programming of the patient specific parameters downloaded from computer system 204. User prompts are preferably provided for requesting the caregiver to enter the particular settings when entered via computer system 204.

Flash memory 240 is used to advantage in pump 100. Unlike removable memory devices, there is no large opening in the pump housing associated with the memory which needs to be protected from tampering, contaminants or moisture. No fragile parts are accessible via communications port 132 from a mechanical protrusion as they would in the case of card readers having relatively large openings to receive the card. The communications port 132 is relatively easy to protect from contaminants and moisture. There is also no loose cartridge or card that could be dislodged, tampered with, damaged or lost. The patient or the caregiver does not need to be concerned that the removable memory device, such as the card or cartridge, is properly positioned in the opening in the pump as in the case of pumps utilizing the separate memory cards or cartridges. This is especially important when the patient is using the pump in an unsupervised location. Should a card or cartridge become dislodged from the pump, there is a concern that the pump would cease operation and the patient would be unable to restart the pump. The use of flash memory 240 eliminates these problems.

Another advantage of flash memory 240 is that neither the caregiver nor the patient needs to maintain any separate memory cartridges or cards for different therapies. There is no need for the caregiver to keep track of any cards, cartridges or other pieces separate from the pump. Disposal or destruction of outdated cards is no longer a problem. Since no card or cartridge reader needs to be provided, there is a reduction in the size of pump 100.

Another advantage of providing flash memory 240 is that there is no need to open up the housing and remove a chip or other wired-in-memory device in order to reprogram the pump. Changes to the applications stored on flash memory 240 are done electronically via the input/output communications port 132. Virtually any programmed function of pump 100 can be electrically changed if desired. As yet undeveloped improvements can be added as they are completed. Caregivers do not need to worry about their pumps becoming obsolete as long as new operating programs are developed. There are no mechanical changes needed for the memory connections to the rest of the pump control system when the flash memory is reprogrammed. Handling of the new chips prior to and during installation is no longer a concern. Disposal or destruction of the old chips is no longer a problem. Applications updates needed by the caregiver can be handled via a floppy disk mailed to the caregiver whereby the caregiver can download the updated program to the pump or the inventory of pumps maintained by the caregiver. Alternatively, the applications updates can be transmitted over the telephone lines via modems to the caregiver. No special expertise is needed to reprogram as is the case of pumps where chips must be removed and replaced to change the memory.

Pump 100 provides system of pumping fluid to a patient where pump 100 is very flexible in how the control system 180 operates. Unlike pumps using EPROM memory for storing the pump operating program, pump 100 with control system 180 is easily changeable as needs and circumstances change. No chips need to be removed or specially handled to reprogram. At the same time, pump 100 is tamper resistant, contamination resistant, and reliable during operation, unlike pumps with replaceable cards.

A further advantage of flash memory 240 is the ability to remotely program flash memory 240. Such remote programming is not possible with cards or cartridges which need to be changed, or replaceable EPROMs which need to be physically handled and reprogrammed. Remote programming can be done initially prior to the first use of the pump or at a later date after initial operation of the pump. The applications can be easily reprogrammed if a bug is identified or if improvements are made in the application program. Applications updates needed by the caregiver can be handled via the telephone lines. Also, changes can be made to the operating program midway through the therapy to address changes in the patient's condition.

Another advantage of the present invention is that custom programs for caregivers who desire particular operating programs for their inventory of pumps are possible through the use of flash memory 240. Individual patients may require a custom program. Flash memory 240 permits the custom program to be quickly downloaded to the patient either locally or remotely via communications port 132. Once the patient no longer needs the custom program, the pump is easily electrically reprogrammed via communications port 132.

Flash memory 240 has sufficiently large memory capability to store the operating program needed to run pump 100, including all of the sensors, switches, and devices.

Since a caregiver can reprogram the pump 100 when the pump is needed for a different application, less inventory of pumps is required by the caregiver. Flash memory 240 permits each pump to be utilized in more than one application over time depending on the immediate needs of the patients. Also, pump 100 may be simpler to operate if only one application is stored in the memory of pump 100. With only one application program stored in the memory, it is not possible for the wrong application program to be selected, once pump 100 is properly programmed. This is a safety feature for protecting the patient from inadvertently receiving the wrong therapy even though a correct drug cartridge is attached. Blocks of flash memory 240 can be used to store different applications for selection by the caregiver or patient.

In some illnesses or treatments, a patient may desire successive different uses of pump 100. For example, some chemotherapy programs are preceded by a nutrition therapy to build up the patient's reserves of fluids or other nutrients. In that case, the memory of pump 100 does not need to simultaneously store both a nutrition therapy application and a chemotherapy application. In that case, the patient would utilize pump 100 with a nutrition therapy application programmed into flash memory 240. At the appropriate time, flash memory 240 could be reprogrammed with the chemotherapy application. Alternatively, flash memory 240 can include all the necessary programs, and the caregiver or patient can select the desired program at the appropriate time.

Keyboard 122 can intentionally be provided with a limited number of keys to keep operation of pump 100 through keyboard 122 simple. However, some applications and even some patient specific settings may involve numerous inputs such that the use of a standard keyboard, through computer system 204 may be advantageous. Downloading of this information from a computer system 204 is useful since all of the inputs of information can be made through a standard keyboard of computer system 204. The present invention provides the caregiver with the ability to download just applications to flash memory 240, or applications to flash memory 240 and patient specific settings to the other memory locations without entering information through keyboard 122.

Since reprogramming of flash memory 240 can only take place with a computer system 204, electronically monitoring the status of the pumps is easier. An updated status check, using appropriate status check program means stored in computer system 204 and/or in pump 100 (for example stored in flash memory 240), can be made of the pump each time there is an application download to the flash memory 240 or each time the pumps 100 are returned to the caregiver after use. The status program means for tracking pump status can help monitor the pumps which are configured for specific types of therapies. The status program means can also include patient name, address and telephone number, and pump location. There are advantages for caregivers and/or pump suppliers to have quick access to status reports on the configuration of the inventory of pumps maintained by the caregiver or supplier. The caregiver or supplier may need to quickly identify particular pumps in case a problem develops where the pumps must be recalled or reprogrammed. Use of computer system 204 to reprogram pump 100 provides a useful way to tie in status tracking software for automatic tracking of each pump 100. The status program means can include recertification tracking program means which automatically flags pumps needed for recertification of the operating systems.

The status program means can be general to only track pump configuration and/or time since recertification. The status program means can also download specific detailed pump operation information from pump 100 to computer system 204 pertaining to the therapy given. Examples of pump operation information that may be sent to computer system 204 from pump 100 include: drug type used, amount of drug used, type of pump operating program used, any changes to pump operating program, dates of pump usage, and a record of all pump start and stop events, number of cassettes used, occurrence of alarms, and other pump usage events. Such information is useful to the caregiver and to the pump supplier/manufacturer. Some of the relevant status information can be entered via the keyboard of computer system 204, instead of from pump 100, at the time of programming before the therapy or at the time of reprogramming after the therapy, such as date information.

Another advantage due to the presence of flash memory 240 having to be reprogrammed with a computer system 204 is that appropriate diagnostic program means for checking pump control system 180 and other features can be downloaded to flash memory 240 each time a programming operation occurs. The diagnostic program means need only be temporarily downloaded to flash memory 240. The diagnostic program means runs through various checks of control system 180 to verify that pump 100 and the associated switches, sensors, and devices are functioning properly. The diagnostic program means is then removed or erased from flash memory 240 and the new application program is downloaded onto flash memory 240. In this manner, any errors in pump 100 can be identified each time a pump 100 is programmed. Such diagnostic program can be downloaded to pump 100 initially before pump 100 is ever programmed to operate as a pump, or at a later date when pump 100 is reprogrammed.

Flash memory 240 allows for convenient reprogramming of pump 100 such that message on display 126 will be in an appropriate language that can be comprehended by the caregiver or patient. For example, messages in Spanish, Japanese or Korean may be displayed to facilitate easy use by the caregiver or patient. Reprogramming of generic pumps in this regard saves on inventory or excessively large pump memory while allowing versatility in use of pump 100. Flash memory 240 also allows for convenient manufacture of pump 100 by permitting a manufacturing program to be stored in flash memory 240. The manufacturing program can be erased once it is no longer needed. The program allows for the various components of pump 100 to be tested during installation.

Figure 8C:
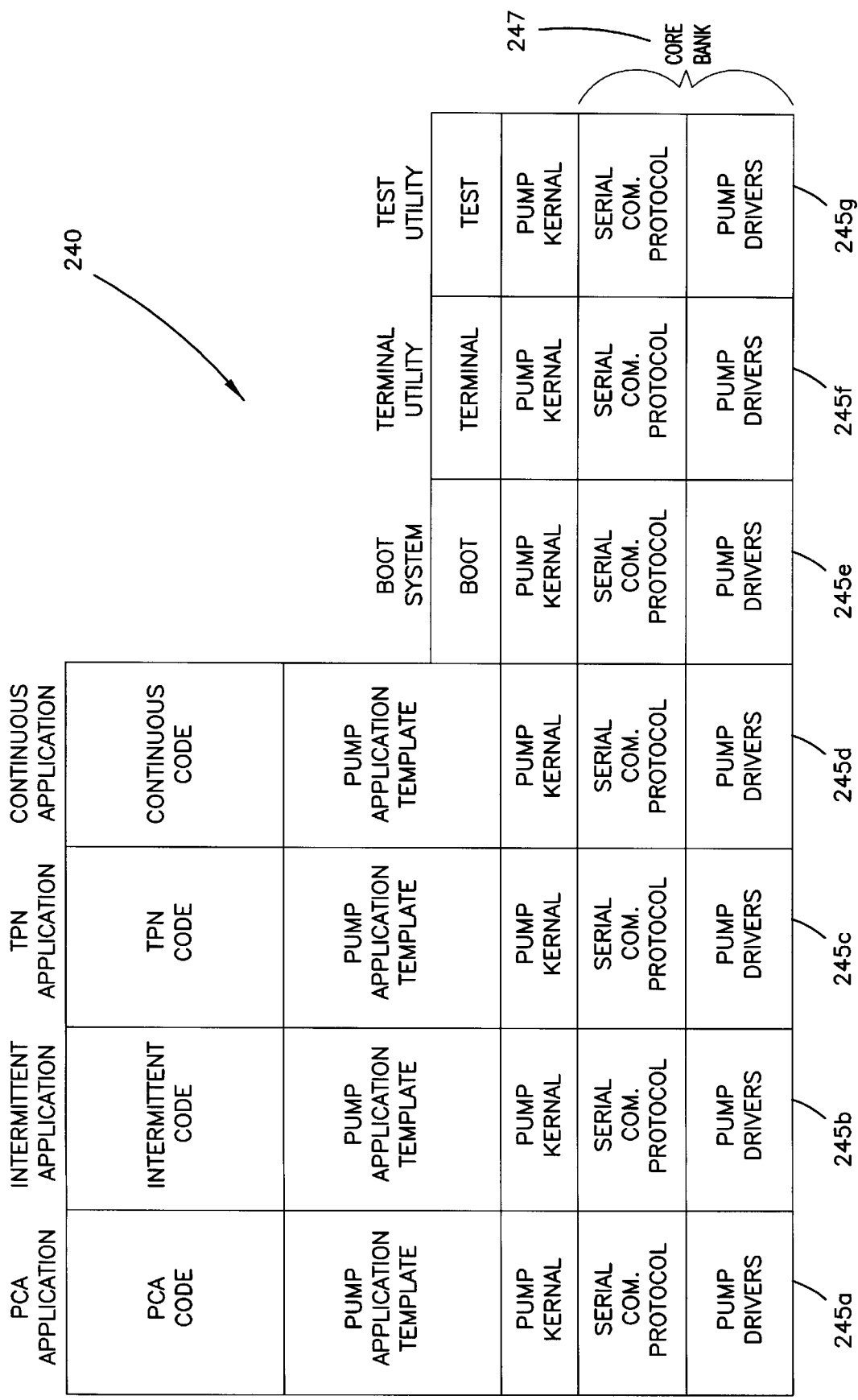
FIGS. 8C–8E lay out the memory configuration of memory devices shown in FIG. 8B.

FIG. 8C illustrates how the flash memory 240 is partitioned. Specifically, the flash memory 240 includes seven program slots 245a–245g for storing a boot system program, four application programs, a terminal utility program, and a testing utility program. The application programs include a PCA application, which is for delivering drugs such as pain relief medication; an intermittent application, which is for intermittent delivery of drugs such as antibiotics; TPN application program, which is for administering fluids such as nutrients; and a continuous application program, which is for continuous administration of drugs such as chemotherapy medication. An example of intermittent delivery is described in U.S. application Ser. No. 08/540,960, which is entitled Intermittent Fluid Delivery Apparatus and Method and filed on Oct. 11, 1995, the disclosure of which is hereby incorporated by reference.

Physically, the flash memory 240 is divided into sixteen banks. Each application program occupies three banks, each utility slot occupies one bank and the boot system occupies one bank. Additionally, the flash memory 240 includes a core bank 247. Although the programs stored in the flash memory are separate entities, they all share the core bank 247. The core bank 247 is used to store pump drivers, a serial communication protocol, and a portion of the pump kernel. The code stored in the core bank is shared by all of the programs.

The boot system is formed from the boot code, the pump kernel, the pump drivers, and the serial communication protocol. The boot system controls the pump 100 at power up. In one possible embodiment, tasks orchestrated by the boot system include self tests or diagnostics. The boot system also generates several screens of information while performing the diagnostics and determines if the pump 100 is in a launch mode or a command mode. The basic tasks performed by the boot software include:

1. performing time critical initializations;
2. performing power up self tests necessary for its own safe operation;
3. keeping hardware watchdogs circuitry from timing out via the drivers;
4. upon detecting an error in the hardware self test, displaying an error code, storing the error code, and halting further execution;
5. displaying various screens of information in the display 126; and
6. determining whether to launch an application, launch a utility, or entering the command mode.

Additionally, if no peripheral device is connected to the communications port 132, the pump 100 will enter the launch mode and the boot system will pass control to the designated or launch application program. A user can change the launch application program, which will cause the pump 100 to go through a warm boot. Once the launch application program is changed, the pump 100 will automatically launch the new application program upon subsequent power ups. If a peripheral device is connected to the communications port 132, the pump 100 will enter command mode and the boot system will send and receive signals via the communication port 132.

Each application program, such as the PCA application, includes an application template, application-specific code, a pump kernel, a serial communication protocol, and pump drivers. The application program controls the pump 100 after being launched by the boot system and performs additional self tests. The pump application program then begins a review sequence during which various screens are generated and displayed showing the current values of selected application parameters.

Upon launching an application program, the pump 100 will automatically stop the pump 100 so that it is not in the normal pumping mode. The caregiver can then program delivery parameters that control how the pump 100 delivers fluid after it is restarted by pressing the START/STOP key. While the pump 100 is running, it is in the normal pumping mode. The pump 100 will deliver fluid and keep track of delivery with status parameters while in the normal pumping mode. It is preferred that none of the application parameters be changeable while the pump 100 is in the normal pumping mode.

The pump application template is a portion of the application program that provides consistency among the various pump application programs. It defines all standard application items, and the user interface structure that each application must follow to create custom application items. Standard application items define the characteristics of each application, which are added to or supplanted by the specific application. The basic tasks performed by the pump application template include:

1. providing all standard menus and help screens, which are available for any specific pump application to use;
2. providing all standard application features, which are available for any specific pump application to use;
3. providing all standard application delivery, status, and configuration parameters, which are available for any specific pump application to use; and
4. providing all standard application alarms, which are available for any specific pump application to use.

The application-specific code is a portion of application program that provides custom application items that are particular to the specific application. The application-specific code is used to customize the pump's 100 behavior and can be programmed only while the pump 100 is stopped. Custom application items may either replace or supplement the standard items provided by the pump application template. Basic tasks performed by a specific pump application include:

1. providing all custom menus and help screens to the kernel, including a start up menu to the kernel that lists the name and/or number of the specific pump applications;
2. providing all custom application features;
3. providing all custom application delivery, status, and configuration parameters to the kernel; and
4. providing all custom application alarms.

Additionally, each application program is an event driven system. The pump drivers provide all hardware interface, and the pump kernel provides support services that include an event scheduling and a dispatching system. The serial communication protocol provides serial communication services with peripherals that are connected to the communications port 132.

Each application program also includes code for communication with a remote pump during pump to pump communications. The pump to pump communication code included in the application program interfaces with the serial communication protocol and is used when the pump 100 is in the slave mode as described above.

The terminal utility is formed from the terminal code, the drivers, the kernel, and the serial communication protocol. The terminal controls the external modem and one of the applications running in the pump 100 via the remote serial connection during pump to pump communication. The pump 100 is in the master mode when the terminal utility is providing serial communication with a remote pump that is in the slave mode.

The testing utility is formed from the testing code, the drivers, the kernel, and the serial communication protocol. The testing utility is a stand alone program that performs various tests on the pump hardware during closed-loop testing.

Figure 8D:
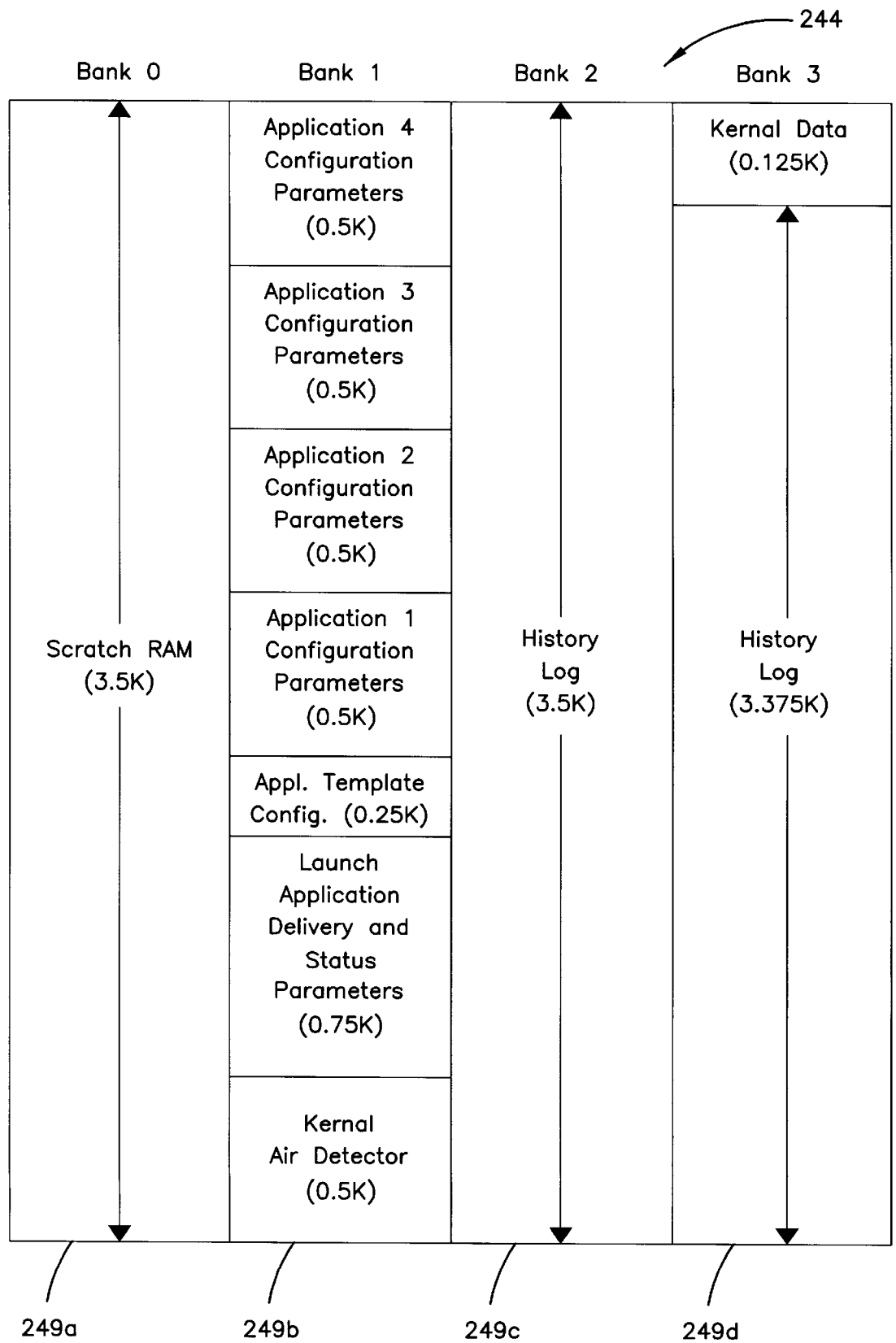

FIG. 8D illustrates the basic configuration of the RAM 244, which has four memory banks, Banks 0–4 249a–249d. Bank 0 249a is dedicated to a scratch memory. Bank 1 249b has four sets of addresses dedicated to configuration parameters for one of the application programs, a set of addresses dedicated to configuration of the application template, a set of addresses dedicated to the delivery status and parameters of the launch application, and a set of addresses dedicated to kernel data. Bank 2 249c is dedicated to a history log. Bank 3 249d is primarily dedicated to the history log. However, a set of addresses in Bank 3 249d are dedicated to kernel data.

The scratch memory serves as a second layer of buffer that provides protection if there is a power failure while data is being written to the RAM 244. During the write process, destination addresses will be designated to receive the data. However, data is first saved in the scratch memory. After the data is saved in the scratch memory, it will be saved to the destination addresses. In one embodiment, data is written to and read from the scratch memory in blocks using an error checking scheme or algorithm such as cyclic redundancy code ("CRC").

A first flag will be set while data is being written to the scratch memory. A second flag is set after the write process is complete at which time it is written from the scratch memory to the destination addresses. Because the RAM 244 is a static RAM, either the first or second flag will be saved of the pump 100 has a power failure.

When power is returned to the pump 100, the flag will be read. If the first flag is set, the pump 100 either can disregard the data in the scratch memory or can complete the process of saving data to the scratch memory. If the second flag is set when power is returned to the pump 100, the pump 100 either can rewrite all of the data from the scratch memory to the destination address or can merely complete the write process from the scratch memory to the destination addresses.

An advantage of using the scratch memory in this manner is that the integrity of the data is maintained while being written to the RAM, which will help minimize the risk of a pump failure or faulty information stored in the history log.

The scratch memory is also used for system diagnostics during power up. The boot program will initially test the scratch memory, which is Bank 0 249*a*. Data from Bank 1 249*b* is then transferred to the scratch memory so that the pump 100 can run diagnostics on that bank. A similar procedure is followed with banks 2 and 3 249*c* and 249*d*.

The four sets of addresses in Bank 1 249*b* for application configuration parameters are used to store persistent data, i.e., parameters that typically remain constant when a particular application program is being used. An example of such data might include the maximum and minimum flow rates or the maximum or minimum concentration settings.

A set of addresses for the application template configuration includes the data that is common between application programs. An application might include the lock level setting or a flag that activates the automatic lock level feature. Addresses for the delivery status and parameter of the launch program are used to store data that is not persistent, including various settings for the launch program. Examples of such data include the delivery rate and dosage. The history log is used to track various historical events such as a change in the delivery rate or when a pump 100 is powered up with time and date stamps.

Figure 8E:
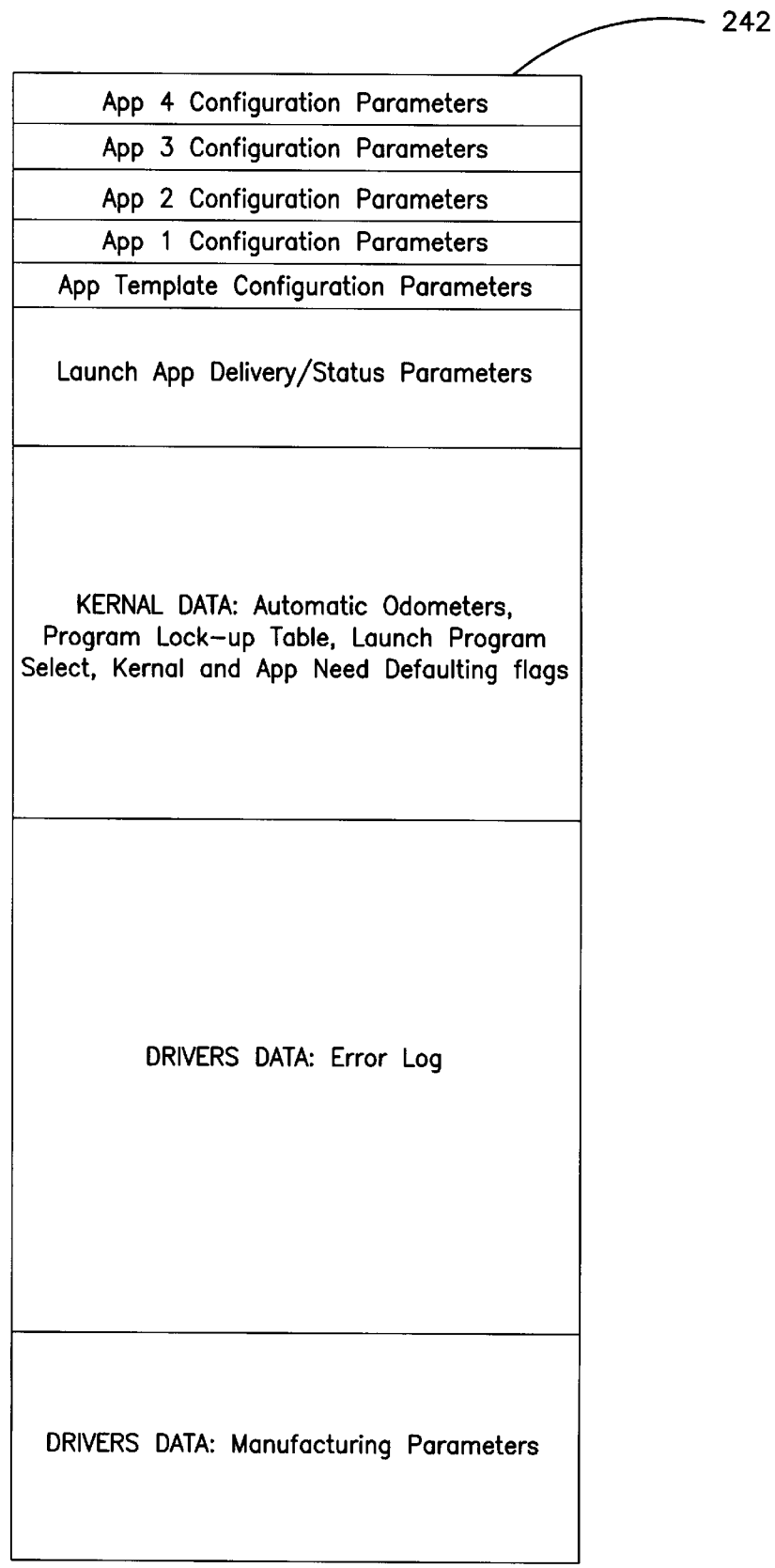

FIG. 8E illustrates the configuration of the EEPROM 242, which is less volatile than the RAM 244. Thus, the EEPROM 242 is used to store data that is more sensitive than the data stored in the RAM 244. Examples of such data include various look-up tables, manufacturer parameters such as the pump serial number, odometers that record data such as hours of use and amount of drug delivered, and an error log to record system faults and nonrecoverable errors. The EEPROM has sets of addresses dedicated to application configuration parameters, application template configuration parameters, launch application delivery and status parameters, kernel data, error log, and manufacturing parameters.

CASSETTE IDENTIFICATION SYSTEMS AND METHODS

This aspect of the present invention relates to systems and methods for automatically identifying a cassette 104 mounted to control module 102 of pump 100. The identification system can identify indicia on the cassette relating to the type of drug, the concentration of the drug, the volume of the fluid reservoir, or the amount of drug pumped per activation of the pump, i.e., tube size. Such information is important to safe and effective drug therapy. When the information is entered automatically to the control module, such as with the indicia identifying system, a safer and more effective system results. There is less chance for human error, as would be the case if such information were entered manually. Also, the indicia identifying system can be used to prevent operation of the pump if an unauthorized cassette is attached.

Various cassettes are provided to be identified by the control module. The control module identifies the cassettes in one of a variety of manners, including engagement with a projection on the cassette or sensing optical signals or the absence of optical signals due to the presence of the cassette. Other structures and methods are provided to identify the cassettes such as described in U.S. Pat. No. 5,531,697 issued Jul. 2, 1996, the disclosure of which is incorporated by reference.

FIG. 4 also shows a lock sensor 190 and a latch sensor 188 interconnected to processor 182. Latch sensor 188 senses when cassette 104 has been latched to control module 102 through the operator activated latch structure 174, 176 which holds cassette 104 adjacent control module 102. FIG. 4 further shows occlusion sensors 186*a,b* interconnected to processor 182. Occlusion sensors 186*a,b* are utilized to sense pressure in tubing 110. Occlusion sensors 186*a,b* and latch sensor 188 are optional with respect to cassette identification. However, these sensors are used to advantage during cassette identification. These sensors can be utilized by microprocessor 182 to identify if there happens to be a malfunction of the cassette identification system. Microprocessor 182 will know when cassette 104 has been mounted to control module 102 by receipt of a latch signal and an appropriate pressure signal (i.e., a pressure sensed within an acceptable operating range). If both upstream and downstream sensing is provided, then an appropriate pressure sensed in each location is determined before pumping can begin. At that point, microprocessor 182 can begin looking for an appropriate signal from cassette identification sensor 196 for identifying indicia on cassette 104. If no identification signal is present, microprocessor 182 does not permit initiation or continuation of the pumping operation by pump mechanism 140. Microprocessor 182 may also send an appropriate error signal to display 126, or alarm 194. Microprocessor 182 checks for a cassette identification signal periodically or continuously. Periodic is preferred as a manner of reducing energy consumption of pump 100.

While the preferred system for identifying cassettes is by identifying a single indicia on each cassette, it is to be understood that the identification system could look for two indicia, such as two projections, for each cassette. A redundant system could still be provided in that case since the control module would request that two signals be received. Less than two or more than two would indicate an error condition. Moreover, the invention is not to be limited to three sensors. More than three, or less than three, are possible whether the systems sense the presence of one indicia, the absence of one indicia, or variations in the number of indicia sensed, such as zero, one, two, three, etc. corresponding to the number of sensors provided and the possible combinations thereof.

Figure 19:
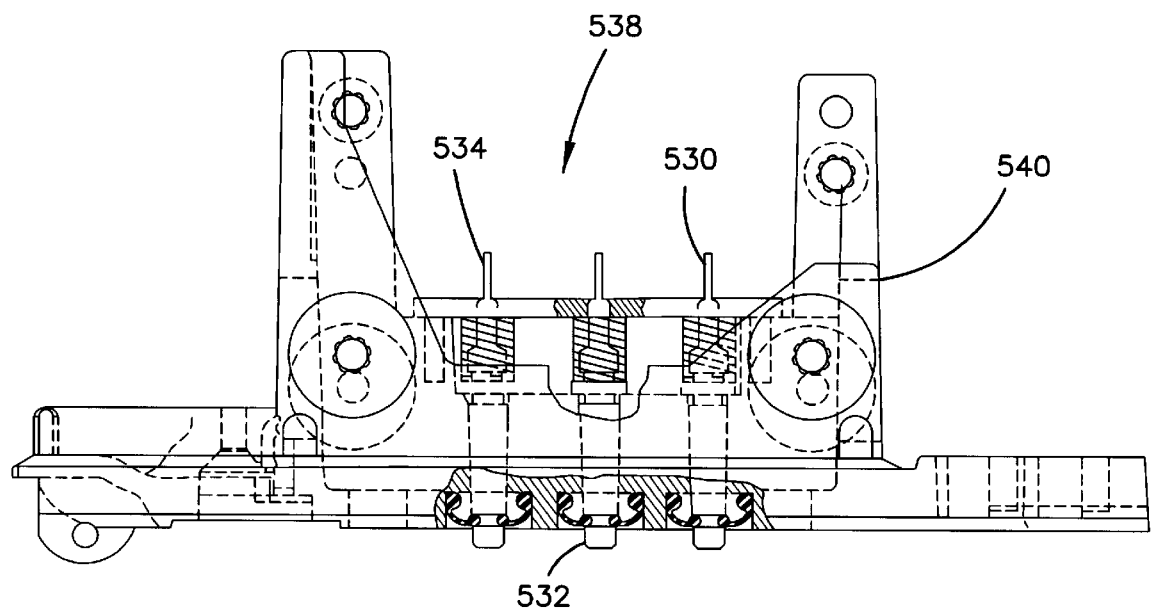
FIGS. 19–27 illustrate one preferred cassette identification system for the pump of FIG. 1.
Figure 20:
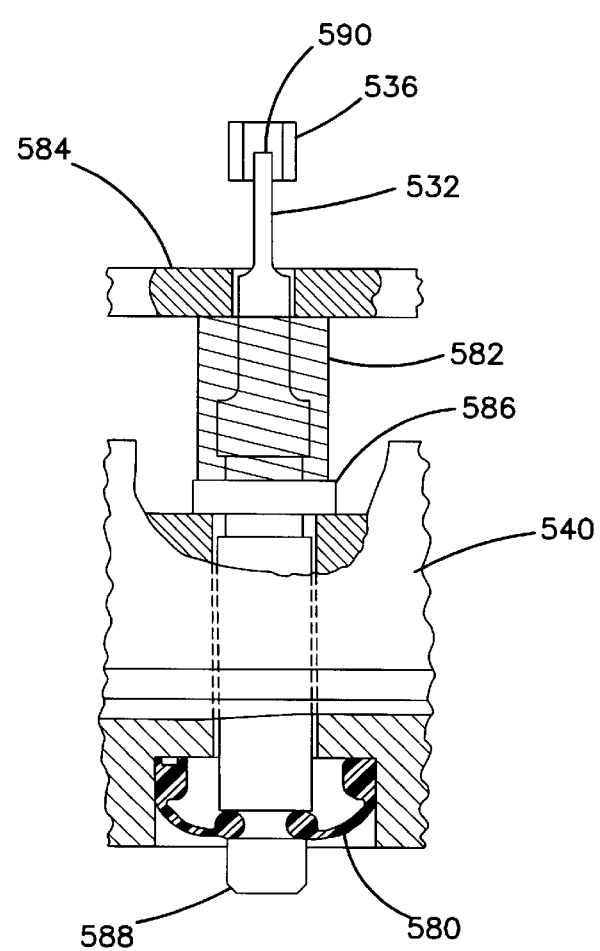
Figure 21:
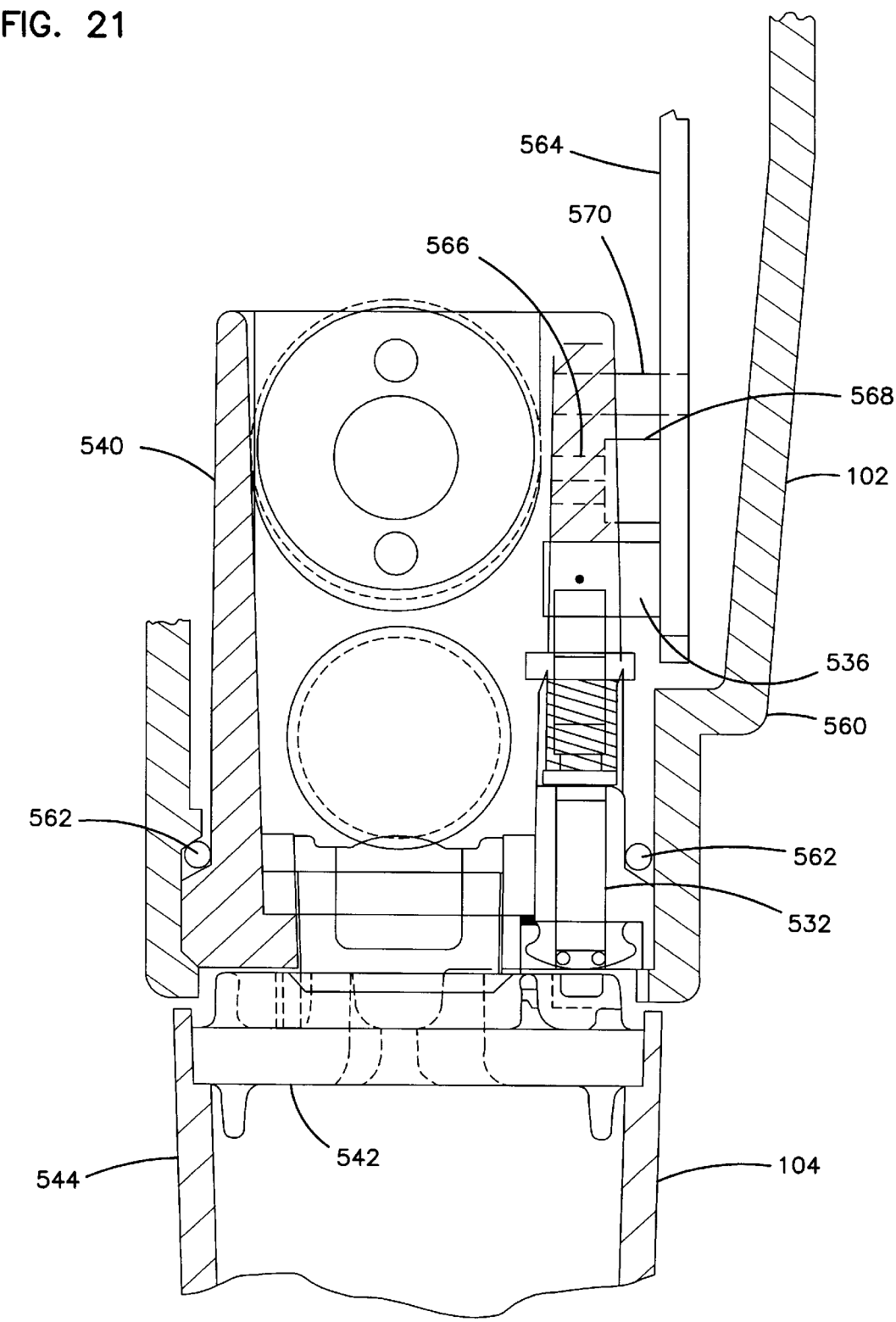
Figure 22:
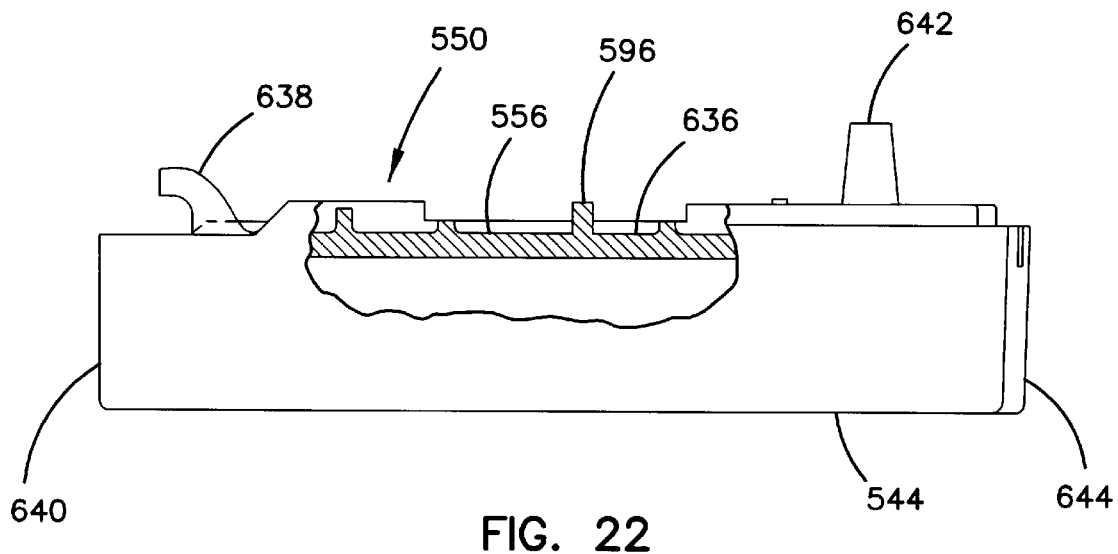
Figure 23:
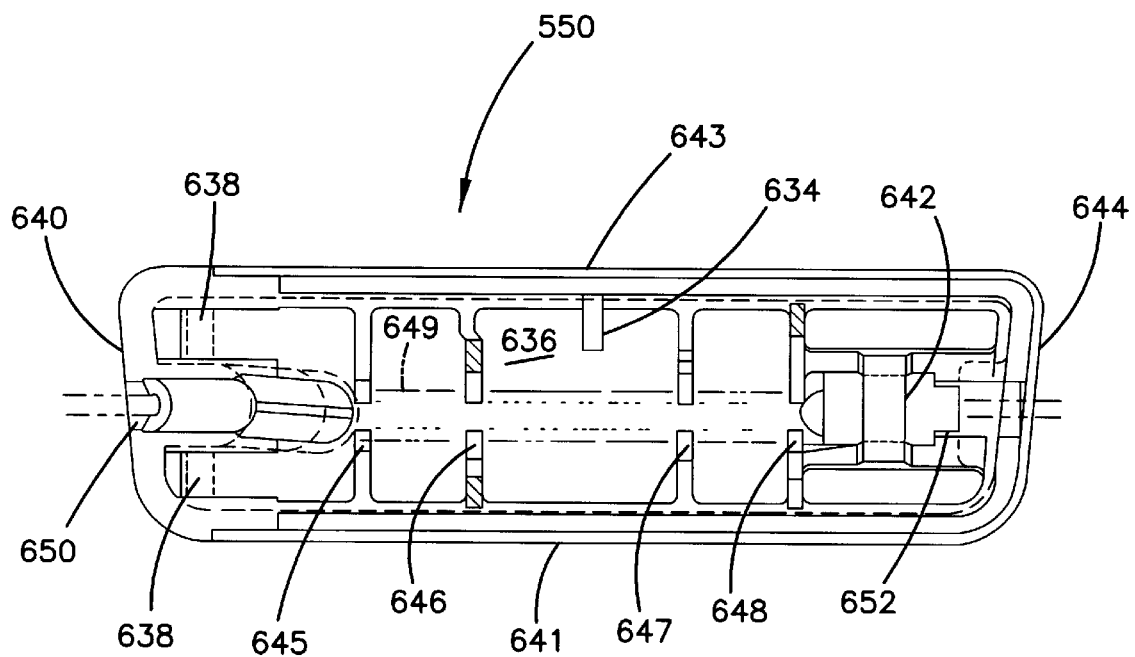
Figure 24:
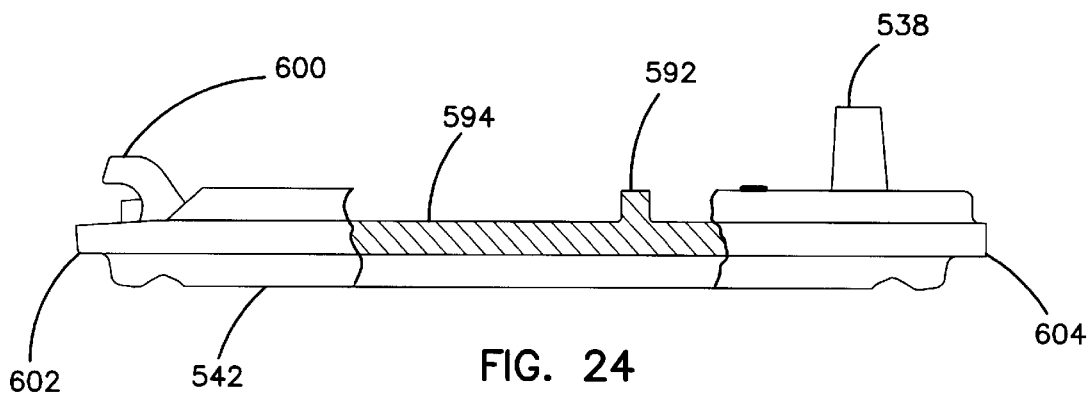
Figure 25:
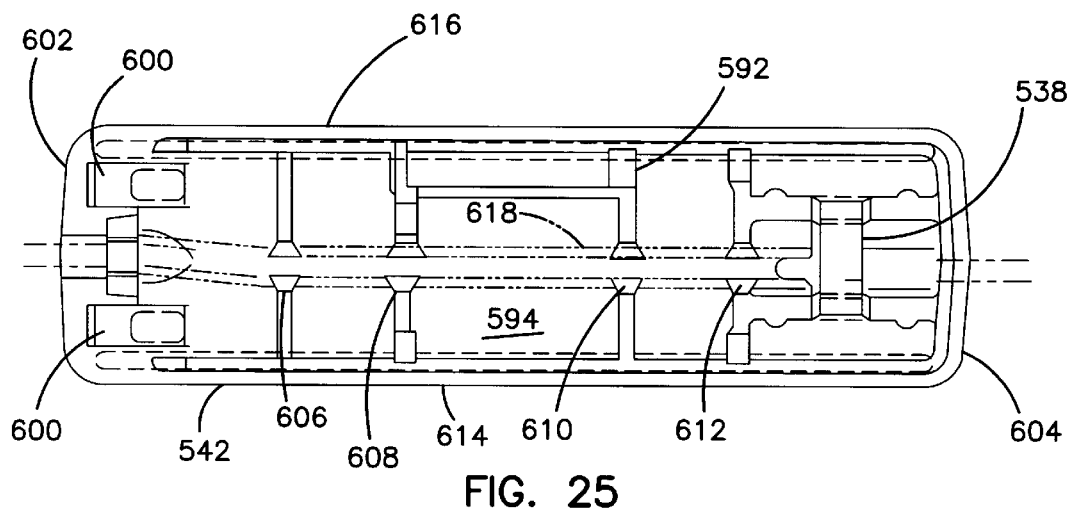
Figure 26:
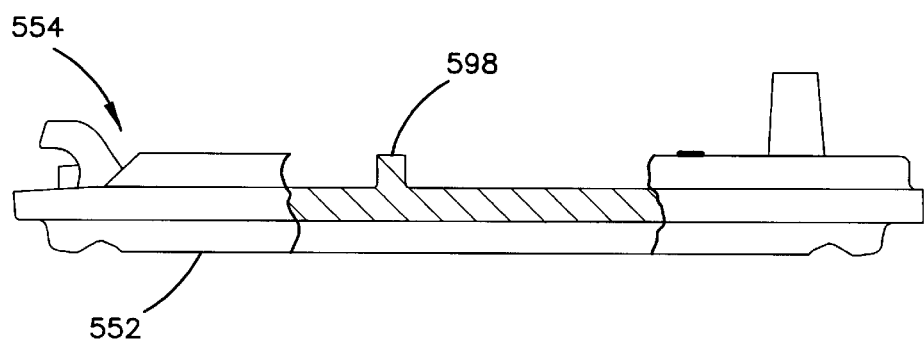
Figure 27:
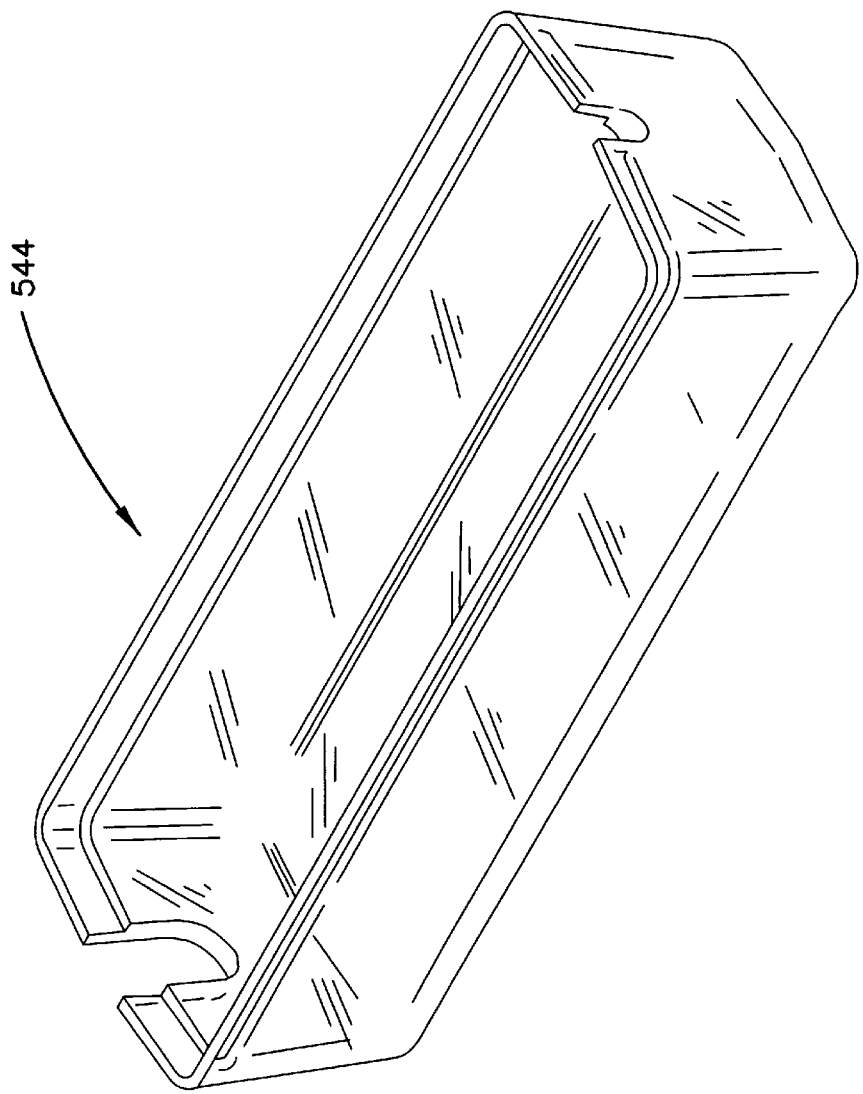

Referring now to FIGS. 19–27, a preferred cassette identification system is shown. Cassette identifier sensor 196 includes three reciprocally mounted plungers 530, 532, 534 and slotted optical sensors like sensor 536 of FIG. 20. The preferred indicia on cassette 104 is one or more projections to engage plungers 530, 532, 534. FIGS. 1, 21, and 22 show a preferred control module 102, a preferred cassette sensing mechanism 538, and a first preferred cassette 104. FIG. 1 shows first cassette 104 assembled and mounted to control module 102. FIGS. 24, 25 and 27 show various side and top views of a base plate 542 of cassette 104, and a perspective view of a base 544 of cassette 104. FIG. 19 shows only chassis 540 with the various plungers mounted thereto. FIG. 21 is an enlarged view of a portion of chassis 540 with a slotted optical sensor 536 shown in its relative position to plunger 532. FIGS. 22 and 23 show a second cassette 550 in side and top views, respectively. FIG. 26 shows a third cassette portion, base plate 552, useable with base 544 of FIG. 27 to form a third cassette 554 in a similar manner as first cassette 104. These second and third cassettes are also part of the preferred cassette identification system. Cassette sensing mechanism 538 can distinguish between cassettes 104, 550, 554. For example, first cassette 104 can have a first pumping volume per activation, i.e., 50 ml. Second cassette 550 can have a second pumping volume per activation, different from the first pumping volume, i.e., 100 ml. It is critical for control module 102 to know how much fluid is pumped per activation of the pumping mechanism to deliver the desired drug therapy. In an improper drug therapy, either too much or too little drug can be harmful, and in some cases, fatal.

As shown in FIG. 21, first cassette 104 includes base plate 542 and base 544 mounted thereto. Base plate 542 is shown in greater detail in FIGS. 24 and 25. Base 544 is shown in greater detail in FIG. 27. Base plate 542 is adhesively or ultrasonically attachable to base 544. Alternatively, a snap arrangement can be provided. In a further alternative, a snap arrangement and adhesive can be utilized. In a further alternative, base plate 542 and base 544 can be integrally formed as a single unit, such as by molding in the case of plastics.

Control module 102 includes a chassis 540 and an outer housing 560. A seal 562 seals between chassis 540 and housing 560. A component board 564 is mounted to chassis 540 via screws 566, spacers 568, and alignment pins 570. A first plunger 530 is reciprocally mounted to chassis 540. Second plunger 532 and third plunger 534 are also reciprocally mounted to chassis 540. Plungers 530, 532, 534 are similarly configured and operated. FIG. 20 shows second plunger 532 in greater detail. A seal 580 seals an end of second plunger 532. A spring 582 biases second plunger 532 to the position shown in FIGS. 19-20. A bezel 584 traps spring 582 in position as shown. A flange 586 limits second plunger 532 from being pulled downwardly out of the position shown in FIGS. 19–20. During operation, a projection extending from the cassette engages end 588 and causes upward movement of second plunger 532 such that end 590 of second plunger 532 moves into a new position relative to slotted optical sensor 536, which causes a signal to be sent to the processor of control module 102 that a projection has been sensed.

First plunger 530 and third plunger 534 are provided for sensing additional projections. In particular, first plunger 530 engages projection 592 extending from the main surface 594 of base plate 542 of first cassette 104. Second plunger 532 engages second projection 596 extending from main surface 636 of base plate 552 of second cassette 550. Third plunger 534 engages projection 598 extending from base plate 552 of third cassette 554. In this manner, control module 102 can identify at least three different cassettes 102, 550, 554.

Referring in particular to FIGS. 21, 24, 25 and 27, base plate 542, and base 544 are shown. Extending from main surface 594 are a pair of hooks 600 adjacent to a first transverse end 602. A loop 538 extends from the main surface 594 adjacent to a second transverse end 604. A plurality of tube guide pairs 606, 608, 610, 612 extend from main surface 594 and are spaced apart to receive a flexible tube, in a general direction parallel to first and second longitudinal sides 614, 616 of main surface 594. In FIG. 24, background portions have been removed behind the cross-sectional portion for clarity. In FIG. 25, a tube 618 is shown in dashed lines.

Referring now to FIGS. 22 and 23, base plate 556, and base 544 are shown in greater detail. Extending from main surface 636 are a pair of hooks 638 adjacent to a first transverse end 640. A loop 642 extends from main surface 636 adjacent to a second transverse end 644. A plurality of tube guide pairs 645, 646, 647, 648 extend from main surface 636 and are spaced apart to receive a flexible tube, in a general direction parallel to first and second longitudinal sides 641, 643 of second cassette 550. In FIG. 23, a tube 649 is shown in dashed lines.

As shown by a comparison of FIGS. 22 and 23 with FIGS. 24 and 25, projection 592 is in a different relative location to projection 596 in a direction parallel to longitudinal sides 641, 643. It should also be noted that FIGS. 22 and 23 illustrate the integral construction between base plate 556 and base 544. Cassette 550 also includes features for more accurate centering of tube 649 which is larger than tube 618, such as the V-shaped passages provided in connection with guide pairs 645, 646, 647, 648.

Also, cassette 550 includes clip features for releasably gripping tube 649 to provide a mechanical hold down during adhesive attachment of tube 649 to cassette 550. In particular, first clip 650 and second clip 652 provide hold down of tube 649 to cassette 550. First clip 650 and second clip 652 hold the tube in place during assembly, allowing the adhesive to set up without the need for special clamps or external fixtures.

Referring now to FIG. 26, third cassette 554 is shown. With respect to FIG. 26, a base plate 552 is illustrated. Base 544 shown in FIG. 27 is useable with base plate 552 shown in FIG. 26. Projection 598 is in a different relative location on base plate 552 than projection 592 of base plate 542 and projection 596 of base plate 556. Projection 598 can be indicative of a different cassette property to differentiate cassette 554 from cassettes 550, 104. For example, cassette 554 may include an indication that an air filter is present to identify to the control module when the cassette is utilized with a reservoir including an in-line air filter.

The cassette identification system of FIGS. 19–27 may be advantageous over mechanical switches, such as microswitches, since little or no emphasis need be placed on overtravel, individual adjustment, arcing problems, and mechanical wearing of the switch. Inductive, magnetic, or reflective systems may require the placement of an additional element on the cassette during manufacture. A projection as in FIGS. 19–27 can be integrally formed on the cassette during manufacture, possibly simplifying manufacture. Force sensitive resistors may be prone to problems due to typical range of necessary movement and the typical tolerances of the disposable cassettes. Also, the plastics associated with the FSR or its spring may be subject to creep problems over time, possibly further complicating the range of motion and tolerance problems. Make or break switches where the contacts are mounted to a moveable plunger, for example, may be prone to failure due to the failure of the contact points, such as due to pitting or corrosion, or due to the components getting stuck open or closed.

Reciprocally mounted plungers and slotted optical sensors are useful to solve some of the above possible problems and other problems with cassette identification systems. However, it is to appreciated that in some instances the use of microswitches, FSR's, inductive switches, magnetic switches, reflective elements, moving contacts, or other systems noted above may be desirable.

AUTOMATED TESTING SYSTEMS AND METHODS

This aspect of the present invention concerns a system for automated testing of a pump, which includes a computer electrically connected to both a testing device and a pump. The pump is connected to the testing device by the pump's fluid tube so that a closed loop configuration is obtained. The medical device is programmed to conduct a variety of tests upon receiving commands from the computer. The testing device provides for measurement of various parameters during the performance of these tests, such as flow rate and pressure. The medical device and/or computer may be programmed to store the test results. By providing a central place for storing such information, not only can each pump be tracked as it moves from location to location, information relating to that pump can be automatically updated. With such a configuration, the testing of the pump is substantially automated.

Figure 28:
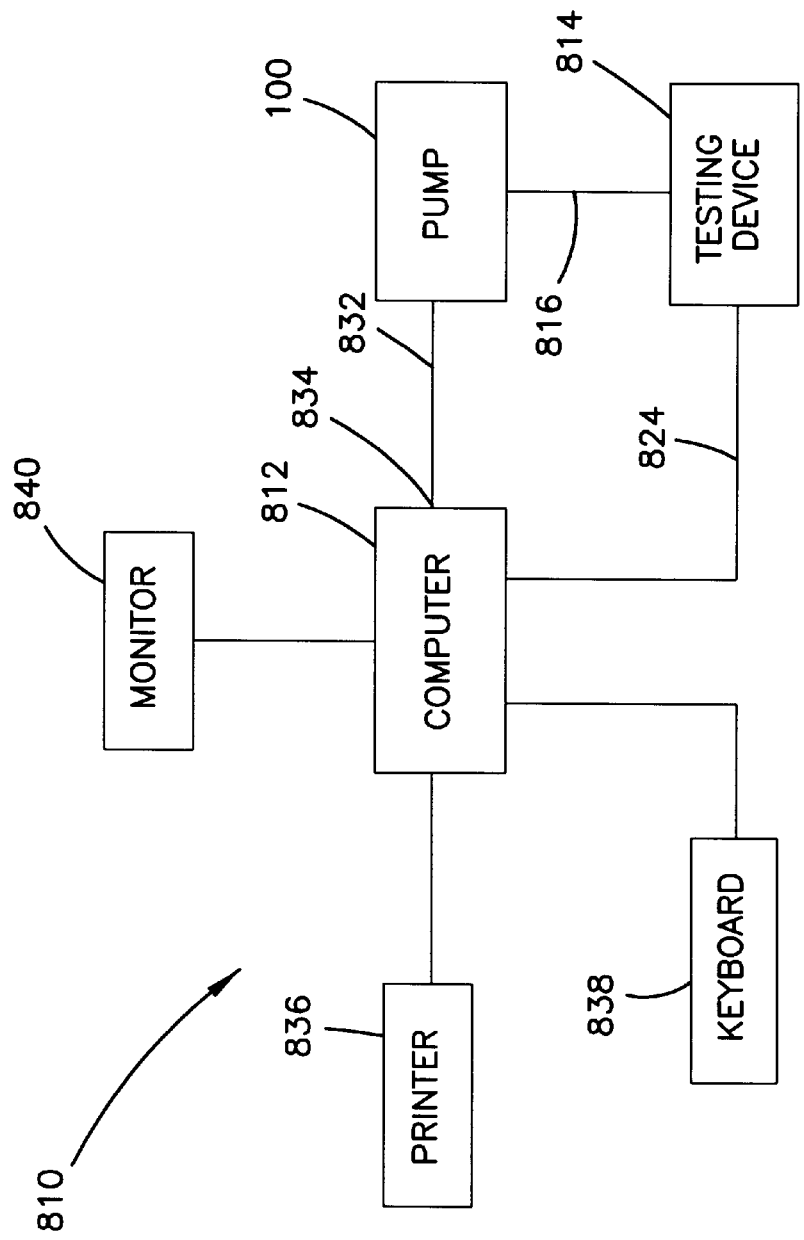
FIG. 28 is a schematic drawing of an automated testing system according to one embodiment of the present invention for testing the pump of FIG. 1.

Referring now to FIG. 28, a system 810 for testing pump 100 is shown. The system 810 includes three major components: a computer 812, a pump 100, and a testing device 814.

As shown in FIG. 28, pump 100 is connected to testing device 814 via tube 816, such as a flexible, compressible tube made of polymeric material. In the case of a peristaltic pump, tube engaging members of drug delivery mechanism engage tube 816 to pump fluid during use.

Figure 29:
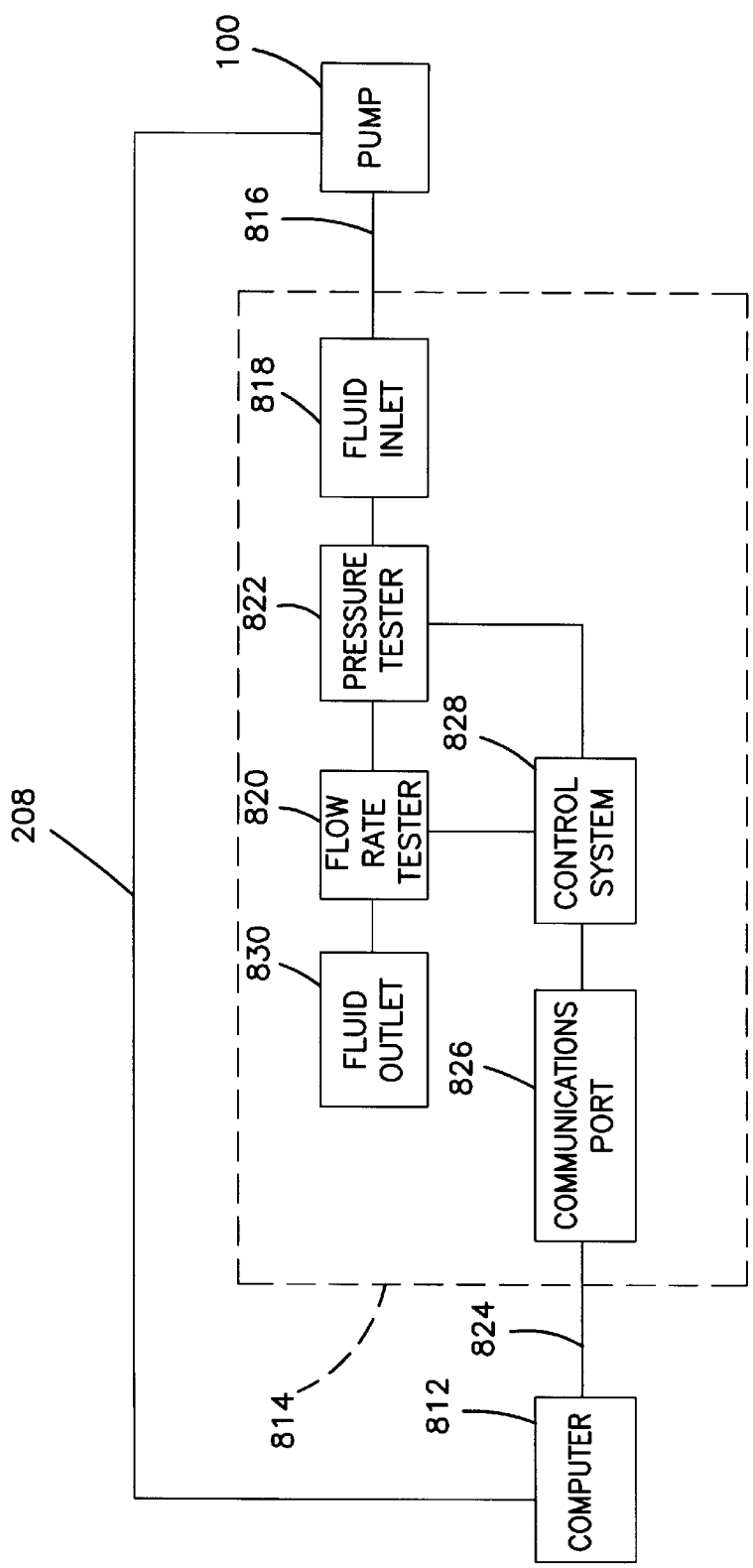
FIG. 29 shows a schematic drawing of one embodiment of the testing device shown in FIG. 28.

Major components of testing device 814 are illustrated in FIG. 29. Testing device 814 is connected to tube 816 of pump 100 via fluid inlet 818. Testing device 814 includes a flow rate tester 820 and a pressure tester 822. Flow rate tester 820 tests the accuracy of the flow rate of a drug being delivered by pump 100. Pressure tester 822 tests the accuracy of medical device's occlusion detector 186 and/or alarms 194 in response to an occlusion in tube 816. Pressure tester 822 measures the pressure generated over time until pump 100 stops, alarm 194 sounds, or pump 100 reaches a certain predetermined test pressure set by computer 812. Computer 812 then compares the pressure measured by testing device 814 to the pressure of pump 100 once alarm 194 sounds or the predetermined test pressure has been reached to determine pressure accuracy. In a preferred embodiment, pressure tester 822 can test at multiple test pressures, such as a range from a low pressure to a high pressure. Testing device 814 is equipped with a fluid outlet 830 for releasing the fluid which runs through testing device 814 during or after the flow rate and pressure tests.

Access to testing device 814 is provided through communications port 826. Preferably, communications port 826 is a standard RS232 communications port. This feature allows information being received via communications port 826 from computer 812 to control testing device 814.

A control system 828 is provided for controlling operation of flow rate tester 820 and pressure tester 822, as well as for controlling communication between testing device 814 and computer 812. Control system 828 includes a microprocessor and associated memory for controlling operation of testing device 814. Testing device 814 may also include an optional display, for displaying information, such as that related to the tests conducted by flow rate tester 820 and pressure tester 822.

One preferred testing device which may be used in system 810 is an Infusion Device Analyzer (IDA) made by Ultramedic, Ltd. of Liverpool, England, and distributed by Bio-Tek Instrument, Inc. of Winooski, Vt. The IDA tests a variety of drug delivery devices, such as infusion pumps.

As is further shown in FIG. 28, both pump 100 and testing device 814 are interconnected to computer 812 via communications links 832 and 824 to form a closed loop testing system. Preferably, computer 812 is a personal computer and communications links 832 and 824 are RS232 cables. Communication links 832 and 824 connect to computer 812 via communications ports 834 and 826, respectively.

Computer 812 further includes a monitor 840 for displaying information related to the operation of system 10, such as test instructions, test results, etc. Such information may also be delivered via hard copy printout to printer 836 attached to computer 812. Computer 812 may also include a keyboard 838 for inputting information into computer 812. Data may also be input into computer 812 via disk, tape, or card reader.

Computer 812 preferably includes a control system for controlling operation of the computer. The control system includes at least a microprocessor and an associated memory with selected functions for controlling operation of the computer. In particular, the memory stores various programs and data needed to run the tests performed on pump 100, such as those performed by flow rate tester 820 and pressure tester 822. Such programs and data may also be stored via disks which may be inserted into computer 112.

Information programmed into computer 112 permits an operator to communicate over communications links 832 and 824 with both pump 100 and testing device 814, respectively. Via communications link 824, computer 812 instructs testing device 814 to measure the flow rate and/or pressure and requests the results of such measurements. With the addition of communications link 832, however, many of the steps performed on pump 100 by flow rate tester 820 and pressure tester 822, which would otherwise have to be performed manually, are now automated.

Communications link 832 also allows for the automation of tests other than the flow rate and pressure tests previously mentioned herein. In particular, via communications link 832, computer 812 can instruct pump 100 to pump fluid for a flow rate test or a pressure test, or to perform internal tests, such as a self-test 898 (see FIG. 45) and a maintenance test 866 (see FIGS. 48A and 48B). Self-test 898 tests the diagnostics of the medical device, such as memory 184 and motor control circuitry (not shown). Maintenance test 866 tests whether operator input structure, sensors, and/or alarms 194 of pump 100 is operating properly. It also tests the structural integrity of pump 100 via operator feedback, including such items as the frame of the device, any power cord, the cassette latch/lock, and any knobs or buttons. As a result of this closed loop configuration, the testing of pump 100 is substantially automated.

Figure 30:
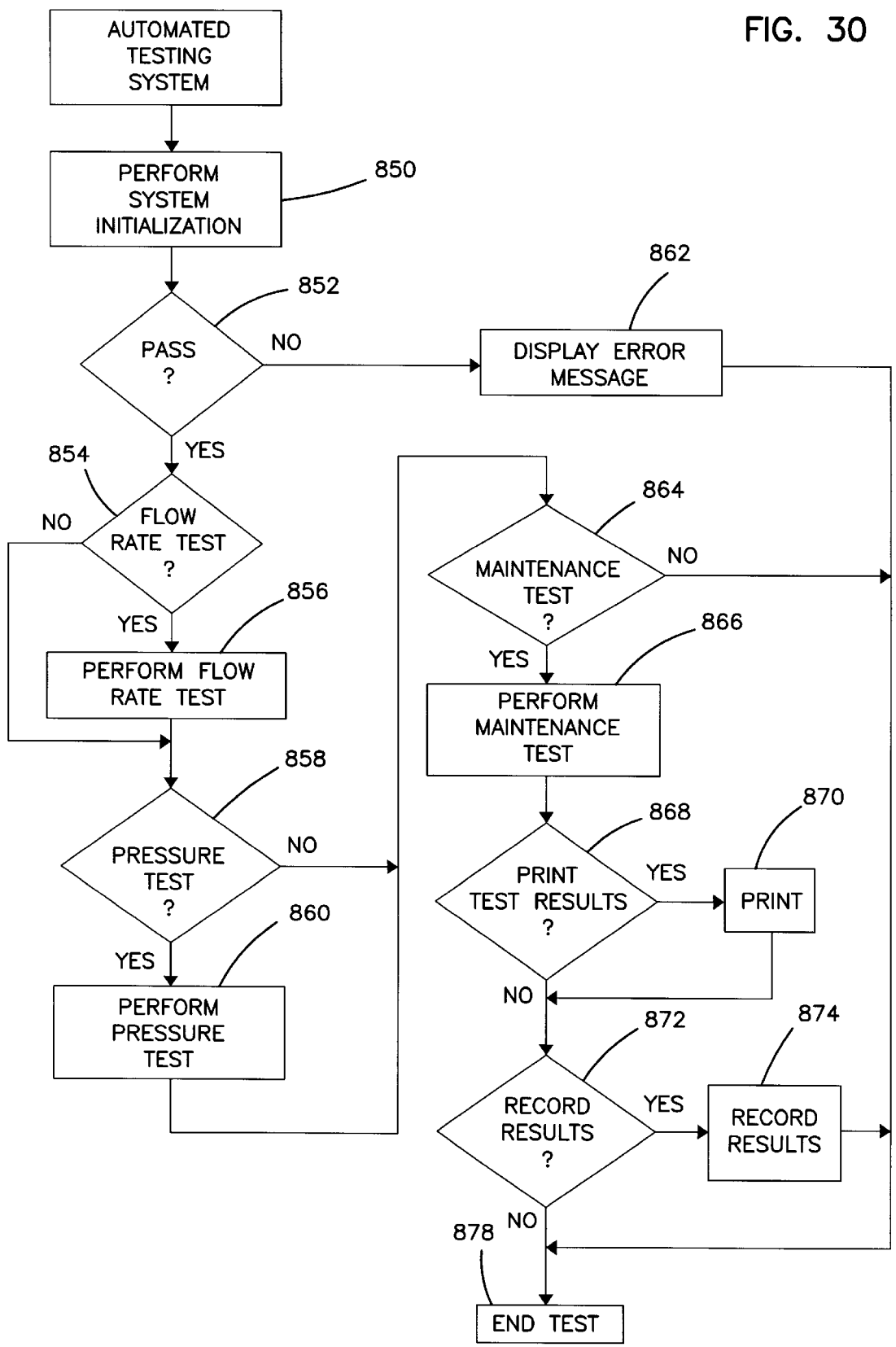
FIG. 30 is a flow chart representation of the preferred steps taken during the testing of the system shown in FIG. 28.

Referring now to FIG. 30, a flow chart is shown illustrating one preferred operational sequence of testing system 810 as shown in FIG. 28 for pump 100. The sequence assumes that all components are connected. Alternatively, computer 812 could instruct the user via monitor 840 to verify the connections between components before beginning the testing process. Once all the components of system 110 are properly connected, system 810 may begin testing.

Specifically, at 850, the system is initialized. At 852, a check is made whether pump 100 successfully completed system initialization 850. If not, at 862, a message is displayed on monitor 840 of computer 812 detailing the error and requesting service, and at 878, the testing procedures are ended. If system initialization 850 is successful, system 810 then conducts a series of tests, such as those performed by flow rate tester 820 and pressure tester 822, as well as maintenance test 864. The list of tests mentioned above, however, is not exclusive. Depending on the medical device being tested, cost constraints, and/or the testing history of the device, more or fewer tests may be performed. Moreover, as those skilled in the art can appreciate, the order in which the tests are performed is not critical.

At 854, a check is made to determine whether the flow rate of pump 100 should be tested. If so, at 856, flow rate tester 820 performs a flow rate test. If not, at 858, a check is made to determine whether the pressure of pump 100 should be tested. If so, at 860, pressure tester 822 performs a pressure test. If not, at 822, a check is made to determine whether a maintenance test should be performed. If so, at 866, a maintenance test is performed. If not, at 868, after all desired tests have been performed, a check is made whether test results should be printed. If so, at 870, a signal is sent to printer 836 to start printing the test results. If not, at 872, a check is made whether the test results should be recorded. If so, at 874, computer 112 records the results. If not, at 700, the testing process is ended.

The flow charts of FIGS. 31 through 34 show more specific operational sequences of each of the tests identified in FIG. 30. The flow charts represent the communication between computer 812 and both pump 100 and testing device 814, as well as any operator interaction with computer 812, pump 100 and testing device 814.

Referring now to FIG. 31 which illustrates a flow chart representation of the steps in a preferred system initialization 850, at 880, computer 112 sends a signal to pump 100 requesting pump specific information from pump 100. Such information may include the device type (syringe, peristaltic, volumetric, etc.), the device's serial number, the manufacturer of the device, and the date of the last test. In the case where pump 100 is dedicated to a patient for extended periods of time, such information may also include the patient's name and address, as well as the name and address of the referring physician. At 882, pump 100 downloads the requested information to computer 812. Such information is useful for device tracking with computer 112.

At 884, a check is made to determine whether computer 812 received the information from the pump. If not, at 140, a further check is made to determine whether pump 100 and computer 812 are in fact connected. If so, at 890, a message is displayed on monitor 840 detailing the error and requesting service, and at 878, the testing process is ended. If not, at 888, computer 812 instructs the operator to connect pump 100 to computer 812, and then repeats steps 880 through 884.

If the information is received by computer 812, at 892, the operator has the option of including additional information, such as the operator's name, and the date and location of the test. If the operator chooses to add information, at 180, he or she may input the information into computer 812 via keyboard 838. If no additional information is added, at 898, computer 812 sends a signal to pump 100 to begin self-test 898. At 900, pump 100 sends a signal back to computer 812 representative of the results of self-test 898. At 902, system initialization 850 is complete.

Figure 32A:
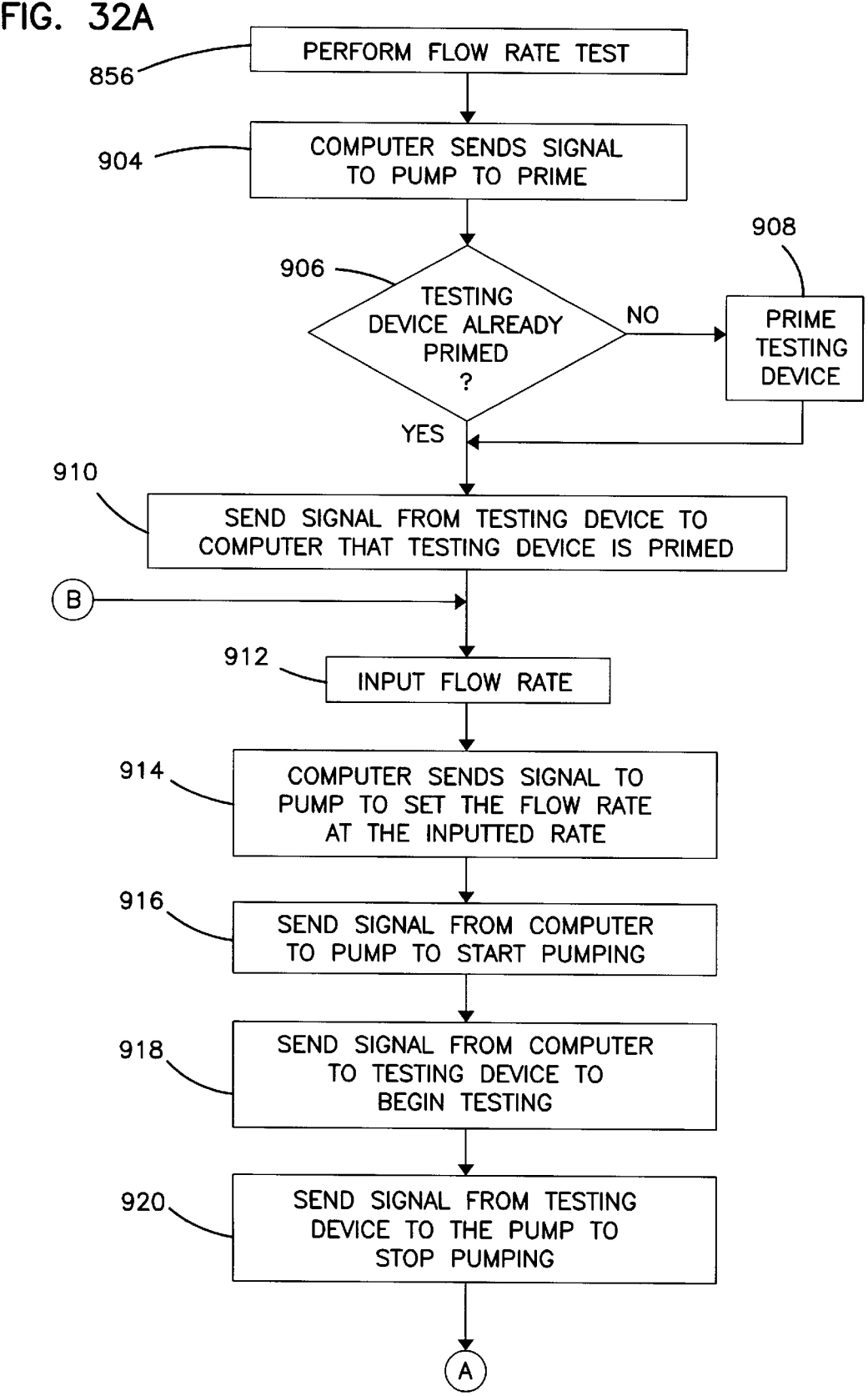
FIGS. 32A and 32B are flow chart representations of the preferred steps taken during the flow test identified in the flow chart of FIG. 30.
Figure 32B:
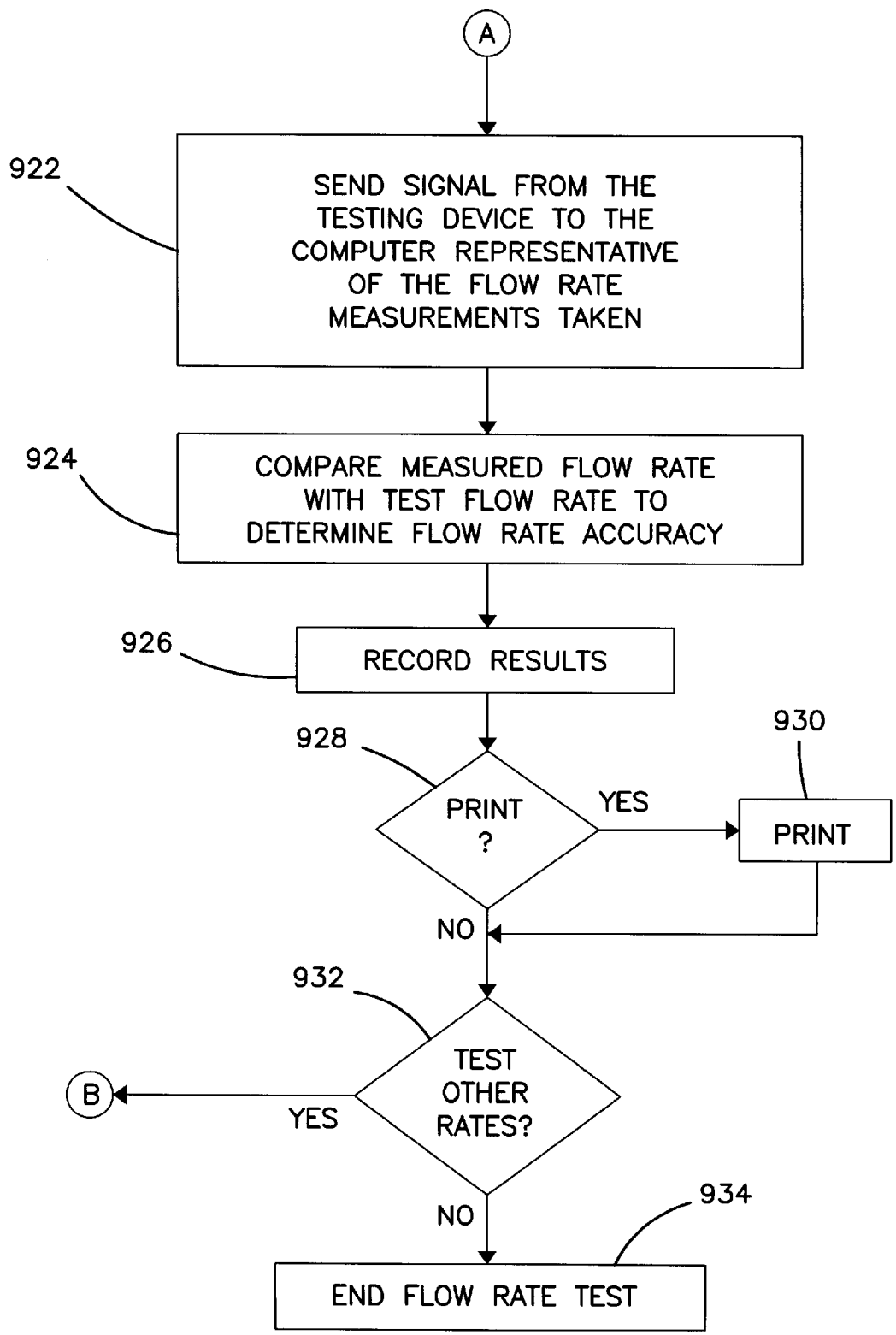

FIGS. 32A and 32B illustrate a flow chart representation of steps in a preferred flow rate test. In order to perform this test, system 810 must be primed. Accordingly, at 904, computer 812 sends a signal to pump 100 instructing it to start priming the system. At 906, a check is made to determine whether testing device 814 is already primed. If not, at 908, computer 812 sends a signal to pump 100 to prime the testing device. If so, at 910, testing device 814 sends a signal back to computer 112 indicating that the testing device is primed.

At 912, computer 812 instructs the operator to input a test flow rate. Computer 812 may be programmed to provide the operator with a menu listing a variety of commonly tested flow rates from which to choose. In a preferred embodiment, computer 812 may automatically command pump 100 to test the flow rate at a single test flow rate or at several test flow rates, such as in a range from a low flow rate to a high flow rate. At 914, computer 812 sends a signal to pump 100 setting the pump at the flow rate chosen by the operator. At 916, computer 812 sends a signal to pump 100 to start pumping. At 918, computer 812 sends a signal to flow rate tester 820 of testing device 814 to begin the flow rate test. After a predetermined period of time, at 920, testing device 814 sends a signal via computer 112 to pump 100 to stop pumping. If the flow rate is automatically selected, steps 912, 914, and 916 are not necessary.

At 922, testing device 814 sends a signal to computer 112 representative of the flow rate measurements taken by the testing device. Such measurements may include the duration of the test, instantaneous and average flow rate, and cumulative volume. It should be appreciated that signals representing real time test data can be sent to computer 812 anytime throughout the duration of the test, provided the infusion is continuous.

At 924, computer 812 compares the measured flow rate with the test flow rate to determine flow rate accuracy. At 926, computer 812 records the test results. At 928, a check is made whether to print the test results. If so, at 930 the results are printed to printer 836. If not, at 932, a check is made whether other flow rates should be tested. If so, computer 812 repeats steps 912 through 930 until all desired testing is complete. Alternatively, the flow rate test results can be printed at the conclusion of all the test procedures (see FIG. 44). Once all flow rate testing is complete, at 934, the flow rate test is ended.

Figure 33:
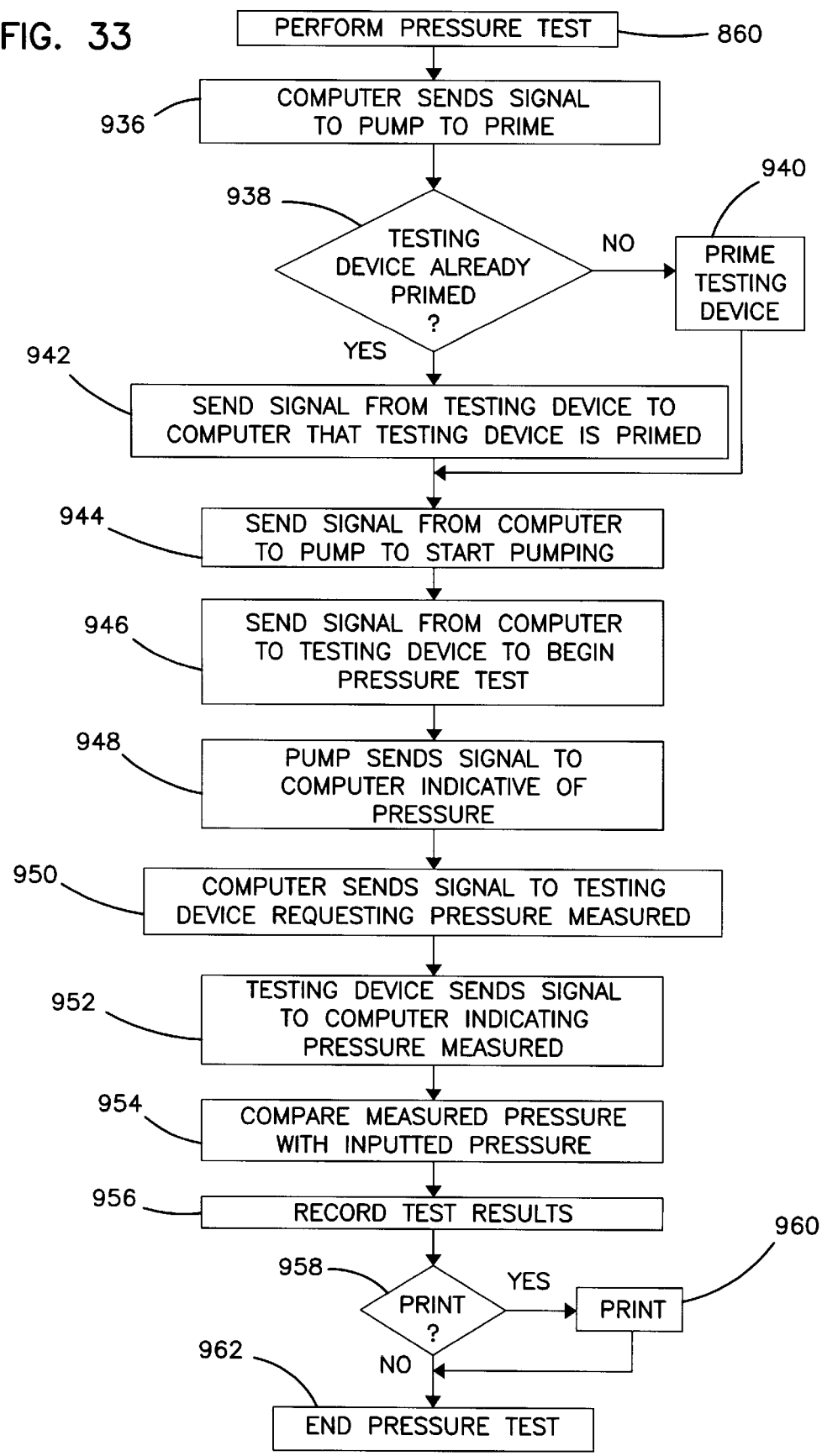
FIG. 33 is a flow chart representation of the preferred steps taken during the pressure test identified in the flow chart of FIG. 30.

FIG. 33 illustrates a flow chart representation of steps taken in a preferred pressure test. As with flow rate tester 820, system 810 must be primed in order to perform this test. Accordingly, at 936, computer 812 sends a signal to pump 100 instructing it to start priming. At 938, a check is made to determine whether testing device 814 is already primed. If not, at 940, computer 812 sends a signal to testing device 814 to prime the testing device. If so, at 942, testing device 814 sends a signal back to computer 112 indicating that the testing device is primed.

At 944, computer 812 sends a signal to pump 100 to start pumping. At 946, computer 812 sends a signal to pressure tester 822 of testing device 814 to begin the pressure test. Pump 100 is set to stop pumping due to an occlusion in tube when the pressure of pump 100 reaches a predetermined level due to the activation of occlusion detector 186 at a predetermined pressure sensed by occlusion detector 186. As previously mentioned, pump 100 may also be set to pump to test one or more pre-selected test pressure settings below the predetermined level where pumping will cease.

At 948, once pump 100 has stopped pumping or has reached the predetermined pressure or pre-selected test pressure, pump 100 sends a signal to computer 812 representative of the pressure sensed by occlusion detector 186. At 950, computer 812 sends a signal to testing device 814 requesting the pressure measured by the testing device. At 952, testing device 814 sends a signal to computer 812 representative of the pressure measured. It should be appreciated, however, that signals representing real time test data can be sent to computer 812 anytime throughout the duration of pressure tester 822.

At 954, computer 112 compares the pressure measured by testing device 814 with the pressure received from pump 100 to determine the accuracy of the response of pump 100 to the occlusion in tube and the accuracy of occlusion detector 186. In an alternate but less desirable mode of operation, the operator himself or herself can read the measured pressure and compare it to the pressure of pump 100 to determine pressure accuracy.

At 956, computer 812 records the tests results. At 958, a check is made whether to print the test results. Alternatively, the pressure test results can be printed at the conclusion of all test procedures (see FIG. 44). If so, at 960, the results are printed to printer 836. If not, at 962, pressure test 822 is ended.

Figure 34A:
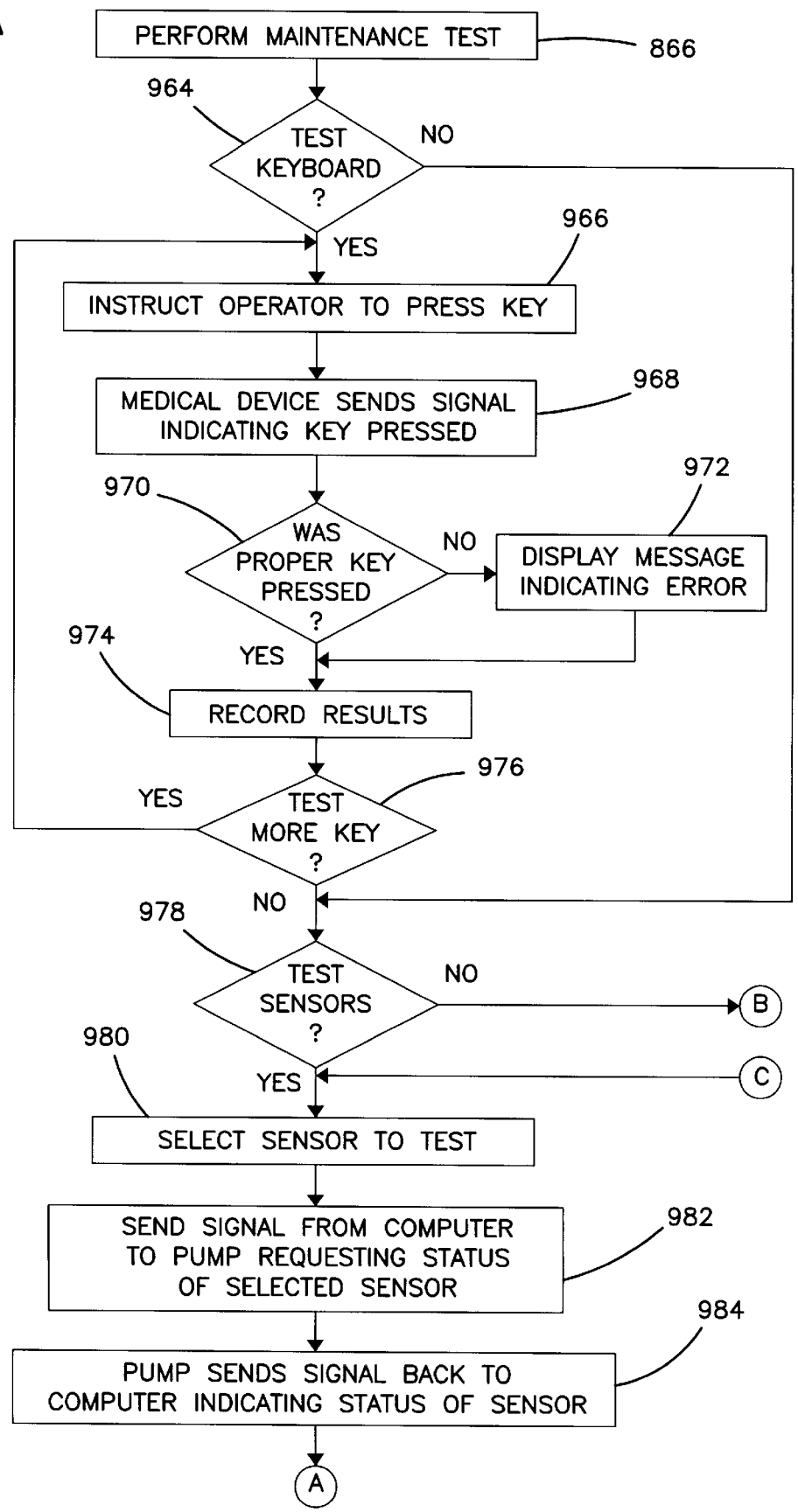
FIGS. 34A and 34B are flow chart representations of the preferred steps taken during the maintenance test identified in the flow chart of FIG. 30.
Figure 34B:
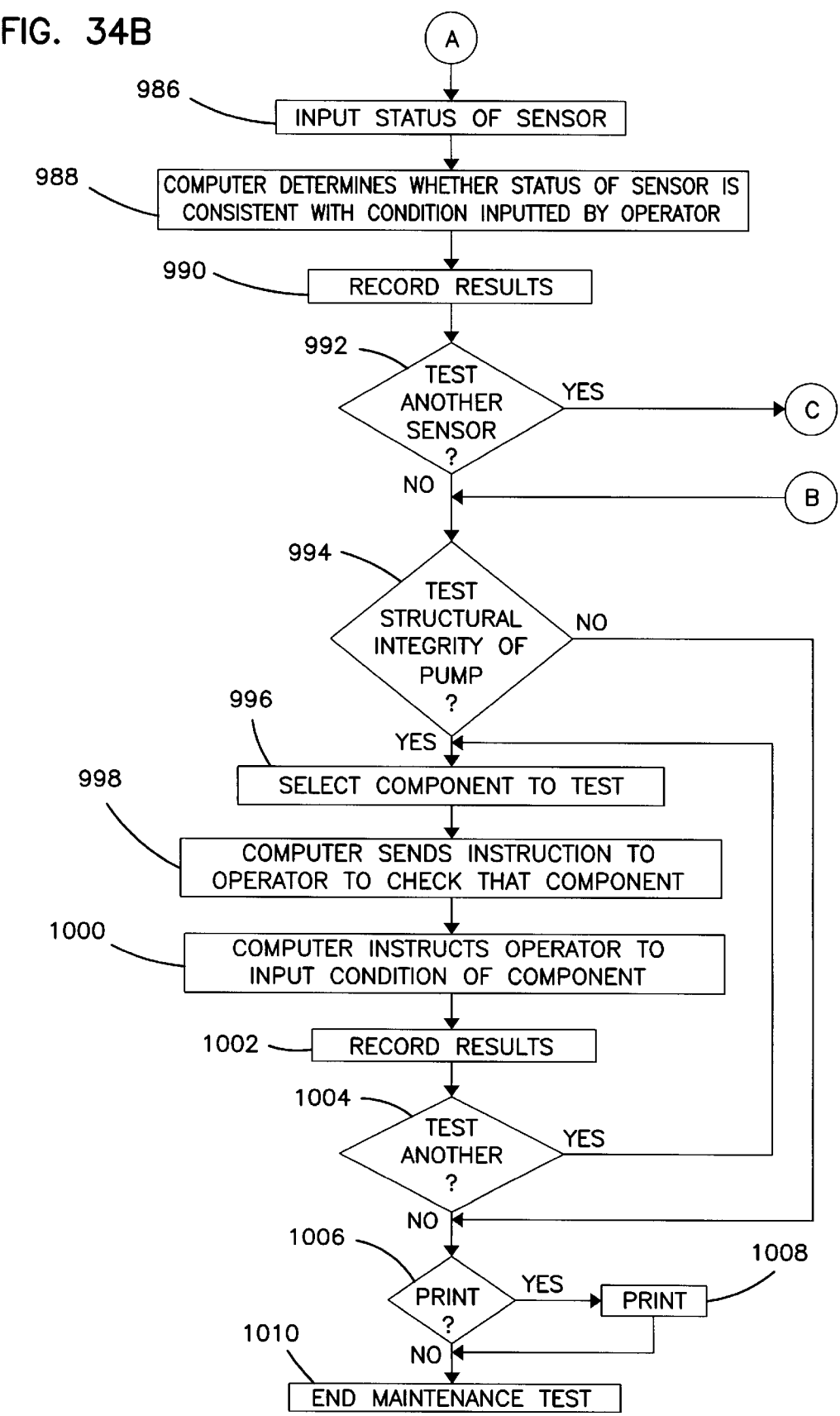

FIGS. 34A and 34B illustrate a flow chart representative of steps taken during a preferred maintenance test 866. At 964, a check is made to determine whether the keyboard (input structure) of pump 100 should be tested. If so, at 966, computer 112 sends a signal to the operator to press a key. At 968, pump 100 sends a signal back to computer 112 indicating which key was pressed. At 970, a check is made to determine whether the key pressed is the same as the key being tested. If not, at 972, a message is displayed on monitor 840 of computer 112 indicating the error. At 974, computer 812 records the results. At 976, a check is made to determine whether to test more keys. If so, steps 966 through 974 are repeated until all the desired keys have been tested.

If no more keys are to be tested, at 978, a check is made to determine whether to test any of the sensors of pump 100. If so, at 980, computer 812 instructs the operator to select the sensor to be tested. At 982, computer 112 sends a signal to pump 100 requesting the status of that sensor. At 984, pump 100 sends a signal back to computer 812 indicating the status of the sensor. At 986, computer 812 instructs the operator to input the status of the sensor being tested. At 988, computer 812 determines whether the status of the sensor is consistent with the condition inputted by the operator.

Computer 812 could instruct the operator to change the status of the sensor. For example, if the latch on the cassette door was closed, the operator could be instructed to unlatch the cassette door. Computer 812 could then determine whether the status of the sensor changed accordingly.

At 990, computer 812 records the results. At 992, a check is made to determine whether the operator wishes to test another sensor. If so, steps 980 through 990 are repeated until all the desired sensors have been tested.

If no more sensors are to be tested, at 994, a check is made to determine whether to test the structural integrity of pump 100. If so, at 996, computer 812 instructs the operator to input the name of the component to be tested. Alternatively, computer 812 could be programmed to provide the operator with a menu from which to chose which components to test. At 998, computer 812 instructs the operator to inspect the component selected. This inspection may be visual and/or physical. At 1000, computer 112 instructs the operator to input the condition of the component. Alternatively, computer 812 could be programmed to provide the user with a rating system from which to rate the component's condition. Such ratings, for example, could include: broken, damaged but operable, fair, etc. At 1002, computer 812 records the result. At 1004, a check is made to determine whether another component should be tested. If so, steps 996 through 1002 are repeated until all desired components are tested. At 1006, a check is made to determine whether to print the test results. Alternatively, the maintenance test results can be printed at the conclusion of all test procedures. If so, at 1008, the results are printed to printer 836. If not, at 1010 maintenance test 866 is ended.

In a preferred embodiment, computer 812 is also preferably programmed to provide the operator with other instructions relating to the particular component being tested, such as how to clean it, how to repair it, if possible, and other related instructions.

While the present invention has been described in connection with the preferred embodiments thereof, it will be understood many modifications will be readily apparent to those skilled in the art, and this application is intended to cover any adaptations or variations thereof. It is manifestly intended this invention be limited only by the claims and equivalents thereof.

What is claimed is:

1. A drug pump for dispensing fluid to a patient comprising:
   a pump mechanism for pumping fluid;
   a processor electrically connected to the pump mechanism;
   a flash memory electrically connected to the processor for storing pump application information for control and operation of the pump mechanism;
   a communication port electrically connected to the processor to permit transfer of pump application information to the flash memory from an exterior of the pump;
   a communications cable sensor associated with the communications port, the communications cable sensor electrically connected with the processor, the communications cable sensor sending a signal to the processor indicative of the presence of a cable plugged into the communication port;
   a reprogrammable memory electrically connected to the processor and separate from the flash memory for storing patient specific settings;
   a keyboard electrically connected to the processor usable to enter the patient specific settings; and
   a display electrically connected to the processor.

2. The drug pump of claim 1, further comprising a boot program stored within the flash memory to permit the initialization and loading of pump application information to the drug pump via the communications port.

3. The drug pump of claim 1, further comprising:
   a pump program stored within the flash memory to control operation of the pump mechanism; and
   a plurality of patient specific settings stored in the reprogrammable memory, the pump application program accessing the patient specific settings to control operation of the pump mechanism.

4. The drug pump of claim 3, further comprising a plurality of pump application programs stored within the flash memory.

5. The drug pump of claim 4, wherein one of the pump application programs is a closed loop testing application program for closed loop testing of the pumping mechanism.

6. The drug pump of claim 4, wherein one of the pump application programs is a master application program for pump to pump communication.

7. The drug pump of claim 6, wherein one of the pump application programs is a closed loop testing application program for closed loop testing of the pumping mechanism and further comprising:
   a cassette identification sensor electrically connected to the processor for identifying a predetermined cassette mounted to the pump mechanism;
   an occlusion sensor electrically connected to the processor for detecting an occlusion in a tubing of a cassette mounted to pump mechanism;
   a latch for latching a cassette to the pump mechanism;
   a lock for locking the latch in the latched state;
   a latch sensor electrically connected to the processor for sensing when the latch is in the latched state; and
   a lock sensor electrically connected to the processor for sensing when the lock is in the locked state.

8. The drug pump of claim 1, further comprising a cassette identification sensor electrically connected to the processor for identifying a predetermined cassette mounted to the pump mechanism.

9. The drug pump of claim 1, further comprising an occlusion sensor electrically connected to the processor for detecting an occlusion in a tubing of a cassette mounted to pump mechanism.

10. The drug pump of claim 1, further comprising:
a latch for latching a cassette to the pump mechanism;
a lock for locking the latch in the latched state;
a latch sensor electrically connected to the processor for sensing when the latch is in the latched state; and
a lock sensor electrically connected to the processor for sensing when the lock is in the locked state.

11. The drug pump of claim 1, further comprising a cassette mounted to the pump mechanism, the cassette including a tubing, and a pressure plate, the tubing positioned between the pressure plate and the pump mechanism.

12. The drug pump of claim 11, further comprising a fluid reservoir connected to the tubing for fluid communication.

13. The drug pump of claim 1, further comprising a cable and a digital simultaneous voice and data modem connected to the communications port by the cable.

14. The drug pump of claim 1, further comprising autolock program means for automatically locking access to the processor following a reprogramming operation of the drug pump.

15. The drug pump of claim 1 wherein the drug pump has a stop mode and a start mode, further wherein the processor has a first state wherein the processor is responsive to a predetermined key stroke and a second state wherein the processor is unresponsive to the predetermined key stroke, the drug pump further comprising circuitry configured to automatically change the processor from the first state to the second state when the drug pump changes from the stop mode to the start mode.

16. A drug pump for dispensing fluid to a patient, the drug pump comprising:
a pump mechanism;
an external communication port;
a processor being in electrical communication with the pump mechanism and in electrical communication with the external communication port, the processor being programmed to communicate with an external processor via the external communications port; and
a sensor in electrical communication with the processor, the sensor configured to detect when a communication cable is connected to the external communication port and to send an electrical signal to the processor in response to detection of the communication cable.

17. The drug pump of claim 16 wherein the processor and the external communication port are configured to provide data communication according to the RS232 standard.

18. The drug pump of claim 17 wherein the external processor is in a remote drug pump.

19. The drug pump of claim 17 wherein the external processor is in a computer.

20. The drug pump of claim 16 further wherein the signal generated by the sensor is an interrupt signal that interrupts operation of the processor.

21. A drug pump for dispensing fluid to a patient, the pump system comprising:
a pump mechanism for pumping fluid;
a microprocessor configured to control the pump;
an external communications port electronically connected to the microprocessor;
a sensor in electrical communication with the microprocessor, the sensor configured to detect when a communication cable is connected to the external communication port and to send an electrical signal to the microprocessor in response to detection of the communication cable;
memory internal to the pump and electronically connected to the microprocessor, the memory storing a boot program and a plurality of application programs, one of the application programs being a predetermined application program; and
wherein the boot program is configured to launch the predetermined application program and the application programs are configured to control operation of the pump.

22. The drug pump of claim 21 wherein each application program implements a fluid delivery algorithm, the fluid delivery algorithm controlling the amount of fluid that is delivered and the time the fluid is delivered.

23. A method of operating a pump wherein the pump includes a microprocessor and memory in electrical communication with the microprocessor, the memory storing a boot program and a plurality of application programs, one of the application programs being a predetermined pump application program, another one of the application programs being a communication program, the pump further including an external communications port, and a cable sensor both in electrical communication with the microprocessor, the method comprising the steps of:
applying power to the microprocessor and the memory;
executing the boot program;
launching the predetermined pump application program;
executing the predetermined pump application program, wherein the predetermined pump application program controls operation of the pump;
sensing with the cable sensor whether a cable is connected to the external communications port; and
if the cable is sensed, launching and executing the communication program, wherein the microprocessor communicates with an external device through the cable.

24. A drug pump for dispensing fluid to a patient, the pump comprising:
a pump mechanism;
a control system electrically connected to the pump mechanism, the control system including a processor and a keyboard, the keyboard being electrically connected to the processor, the processor being programmed to respond to predetermined keystrokes, the processor being further programmed with a plurality of access locks; and
wherein each access lock, when activated, prevents the processor from responding to a set of predetermined keystrokes;
wherein the pump has a first state in which the pump mechanism does not dispense fluid to the patient and second state in which the pump mechanism does dispense fluid to the patient, one of the access locks being a predetermined access lock, the processor being further configured to automatically activate the predetermined access lock when the pump changes from the first state to the second state.

25. The drug pump of claim 24 wherein each set of predetermined key strokes corresponds to a unique function.

26. A method of operating a drug pump comprising the steps of:
   a) unlocking an access lock of a processor of a drug pump;
   b) reprogramming a memory of the drug pump connected to the processor after the access lock is unlocked; and
   c) after step b), automatically relocking the access lock.

27. A drug pump for dispensing fluid to a patient, the drug pump comprising:
   a pump mechanism, the pump mechanism including a motor and a motor controller;
   at least one sensor;
   a serial communication device electrically connected to a communication port;
   a processor; and
   a data bus, the data bus providing electrical communication between the processor and the motor controller, the at least one sensor, and the serial communication device, wherein the at least one sensor is an external communication sensor, the external communication sensor configured to generate a signal when a communication cable is connected to the communication port.

28. The drug pump of claim 27 wherein the at least one sensor is an air detector configured to generate a signal when air is detected in the fluid being dispensed to the patient.

29. The drug pump of claim 28 wherein the at least one sensor is a temperature sensor configured to generate a signal indicative of the ambient air temperature.

30. The drug pump of claim 29 wherein the at least one sensor is a motor position sensor configured to generate a signal indicating the position of the motor.

31. A drug pump for dispensing fluid to a patient, the drug pump comprising:
   a control module, a cassette, the cassette including a pressure plate including two hooks at one end and a loop at an opposite end, a fluid reservoir and a fluid line in fluid communication with the reservoir, the pressure plate having indicia, the control module having two pins and a latch to attach the hooks and the loop, respectively, of the pressure plate to the control module, the fluid line positioned between the pressure plate and the control module;
   a pump mechanism on the control module configured to pump fluid from the reservoir and through the fluid line, the pump mechanism engaging the fluid line against the pressure plate;
   an occlusion detector on the control module configured to detect a pressure level in the fluid line;
   a latch sensor on the control module and configured to detect the latch in the latched state;
   a cassette identification sensor on the control module and configured to detect the indicia on the pressure plate; and
   a processor within the control module electrically connected to the pump mechanism, the occlusion detector, the latch sensor, and the cassette identification sensor, the processor configured to disable the pump mechanism upon detection of, a pressure level in the fluid line above or below a predetermined operating range, a failure to detect the latch in the latched state, or a failure to detect the indicia.

32. The drug pump of claim 31, further comprising a lock for locking the cassette to the control module, and a lock sensor configured to detect the lock, the processor configured to disable the pump mechanism upon a failure to detect the lock.

33. A method of operating a drug pump comprising the steps of:
   a) selecting a pump operating program from a plurality of different pump operating programs stored on the drug pump;
   b) inputting patient specific settings to the drug pump;
   c) pumping fluid to a patient with the drug pump;
   d) linking the drug pump to a remote caregiver drug pump over a modem connection; and
   e) inputting a further patient specific setting to the drug pump from the caregiver drug pump over the modem connection.

34. The method of claim 33, further comprising the steps of:
   a) connecting the drug pump to a personal computer and to a fluid analyzer including a flow rate accuracy testing mechanism and a pressure testing mechanism;
   b) operating the drug pump through control signals sent from the personal computer; and
   c) collecting fluid at the fluid analyzer from the drug pump.

35. The method of claim 33, further comprising the steps of:
   a) sending status report data from the drug pump to the caregiver drug pump before step e); and
   b) sending status report data from the drug pump to the caregiver drug pump after step e).

* * * * *

UNITED STATES PATENT AND TRADEMARK OFFICE
CERTIFICATE OF CORRECTION

PATENT NO.    : 5,935,099
DATED         : August 10, 1999
INVENTOR(S)   : Peterson et al.

It is certified that error appears in the above-identified patent and that said Letters Patent is hereby corrected as shown below:

Title page,
Item [63], Related U.S. Application Data, delete "application No. 08/618,574, Mar. 20, 1996, Pat. No. 5,647,854, and application No. 08/281,179, Jul. 27, 1994, Pat. No. 5,695,473", insert -- application 08/276,025, July 15, 1994, Pat. No. 5,485,408, application 07/942,288, September 9, 1992, Pat. No. 5,338,157 --

Column 1,
Lines 15-19, delete "; 08/618,574, filed Mar. 20, 1996, now U.S. Pat. No. 5,647,854, which is a continuation of 08/228,408, filed Apr. 15, 1994, now U.S. Pat. No. 5,531,697, and 08/281,179, filed Jul. 27, 1994, now U.S. Pat. No. 5,695,473"
Line 15, insert -- , now issued as U.S. Pat. No. 5,788,669 -- after "Oct. 11, 1995"

Column 49, line 32 to Column 50, line 18,
Delete claims 31 and 32 in their entirety Signed and Sealed this Twentieth Day of August, 2002

Attest:

Attesting Officer

JAMES E. ROGAN
*Director of the United States Patent and Trademark Office*